United States Patent
Shimizu et al.

(10) Patent No.: US 7,119,256 B2
(45) Date of Patent: Oct. 10, 2006

(54) GENE ENCODING ACETOLACTATE SYNTHASE

(75) Inventors: Tsutomu Shimizu, Shizuoka (JP); Ishizue Nakayama, Shizuoka (JP); Kozo Nagayama, Shizuoka (JP); Atsunori Fukuda, Ibaraki (JP); Yoshiyuki Tanaka, Ibaraki (JP); Koichiro Kaku, Shizuoka (JP)

(73) Assignees: Kumiai Chemical Industry Co., Ltd., Tokyo JPX; National Institute of Agrobiological Sciences, Tsukuba (JP)

( * ) Notice: Subject to any disclaimer, the term of this patent is extended or adjusted under 35 U.S.C. 154(b) by 96 days.

(21) Appl. No.: 10/432,962

(22) PCT Filed: Nov. 16, 2001

(86) PCT No.: PCT/JP01/10014

§ 371 (c)(1),
(2), (4) Date: May 29, 2003

(87) PCT Pub. No.: WO02/44385

PCT Pub. Date: Jun. 6, 2002

(65) Prior Publication Data

US 2004/0088753 A1    May 6, 2004

(30) Foreign Application Priority Data

Nov. 29, 2000    (JP) .............................. 2000-362630

(51) Int. Cl.
*C12N 15/29* (2006.01)
*C12N 15/82* (2006.01)

(52) U.S. Cl. ...................... 800/300; 435/6; 435/320.1; 536/23.2

(58) Field of Classification Search ............... 536/23.2, 536/32.6; 435/320.1, 6; 800/278, 300
See application file for complete search history.

(56) References Cited

U.S. PATENT DOCUMENTS 5,633,437 A * 5/1997 Bernasconi et al. ........ 800/278
2003/0217381 A1* 11/2003 Croughan .................... 800/278

FOREIGN PATENT DOCUMENTS

WO    WO 00/27182 A1    5/2000
WO    WO 01/85970 A2    11/2001

OTHER PUBLICATIONS

Duggleby 1997, Gene 190:245-249.*
Karl-Heinz Ott et al.; Journal of Molecular Biology; vol. 263; 1996; pp. 359-368; XP002118465.
Ronald Duggleby et al; Journal of Biochemistry and Molecular Bioligy; vol. 33; No. 1; Jan. 2000; pp. 1-36; XP001119823.
Bernasconi, P., et al. J. Biol. Chem., vol. 270, No. 29, pp. 17381-17385, 1995.
Mourad, G., et al. Mol. Gen. Genet., vol. 243, No. 2, pp. 178-184, 1994.
Lawrence, Y., et al. Plant Molecular Biology, vol. 18, No. 6, pp. 1185-1187, 1992.
Chipman, David, et al. Biochim. Biophys. Acta, vol. 1385, pp. 401-419, 1998.

* cited by examiner

*Primary Examiner*—David H Kruse
(74) *Attorney, Agent, or Firm*—Birch, Stewart, Kolasch & Birch, LLP

(57) ABSTRACT

The present invention provides a gene encoding ALS protein which shows a extremely high level of resistance to pyrimidinyl carboxy herbicides. The gene of the present invention encodes an acetolactate synthase protein, for instance, according to SEQ ID NO:1, where the acetolactate synthase protein has resistance to a pyrimidinyl carboxy herbicide and has acetolactate synthase activity.

9 Claims, 37 Drawing Sheets

Fig. 1

1st Amino Acid Sequence
  File Name       : Double-point mutant ALS amino acid sequence
2nd Amino Acid Sequence
  File Name       : Wild type ALS amino acid sequence

```
  1'  MATTAAAAAAALSAAATAKTGRKNHQRHHVLPARGRVGAAAVRCSAVSPVTPPSPAPPAT
      ************************************************************
  1"  MATTAAAAAAALSAAATAKTGRKNHQRHHVLPARGRVGAAAVRCSAVSPVTPPSPAPPAT

61'  PLRPWGPAEPRKGADILVEALERCGVSDVFAYPGGASMEIHQALTRSPVITNHLFRHEQG
      ************************************************************
 61"  PLRPWGPAEPRKGADILVEALERCGVSDVFAYPGGASMEIHQALTRSPVITNHLFRHEQG

121'  EAFAASGYARASGRVGVCVATSGPGATNLVSALADALLDSVPMVAITGQVPRRMIGTDAF
      ************************************************************
121"  EAFAASGYARASGRVGVCVATSGPGATNLVSALADALLDSVPMVAITGQVPRRMIGTDAF

181'  QETPIVEVTRSITKHNYLVLDVEDIPRVIQEAFFLASSGRPGPVLVDIPKDIQQQMAVPV
      ************************************************************
181"  QETPIVEVTRSITKHNYLVLDVEDIPRVIQEAFFLASSGRPGPVLVDIPKDIQQQMAVPV

241'  WDTSMNLPGYIARLPKPPATELLEQVLRLVGESRRPILYVGGGCSASGDELRWFVELTGI
      ************************************************************
241"  WDTSMNLPGYIARLPKPPATELLEQVLRLVGESRRPILYVGGGCSASGDELRWFVELTGI

301'  PVTTTLMGLGNFPSDDPLSLRMLGMHGTVYANYAVDKADLLLAFGVRFDDRVTGKIEAFA
      ************************************************************
301"  PVTTTLMGLGNFPSDDPLSLRMLGMHGTVYANYAVDKADLLLAFGVRFDDRVTGKIEAFA

361'  SRAKIVHIDIDPAEIGKNKQPHVSICADVKLALQGLNALLQQSTTKTSSDFSAWHNELDQ
      ************************************************************
361"  SRAKIVHIDIDPAEIGKNKQPHVSICADVKLALQGLNALLQQSTTKTSSDFSAWHNELDQ

421'  QKREFPLGYKTFGEEIPPQYAIQVLDELTKGEAIIATGVGQHQMWAAQYYTYKRPRQWLS
      ************************************************************
421"  QKREFPLGYKTFGEEIPPQYAIQVLDELTKGEAIIATGVGQHQMWAAQYYTYKRPRQWLS

481'  SAGLGAMGFGLPAAAGASVANPGVTVVDIDGDGSFLMNIQELALIRIENLPVKVMVLNNQ
      ************************************************************
481"  SAGLGAMGFGLPAAAGASVANPGVTVVDIDGDGSFLMNIQELALIRIENLPVKVMVLNNQ

541'  HLGMVVQLEDRFYKANRAHTYLGNPECESEIYPDFVTIAKGFNIPAVRVTKKSEVRAAIK
      ******* ****************************************************
541"  HLGMVVQWEDRFYKANRAHTYLGNPECESEIYPDFVTIAKGFNIPAVRVTKKSEVRAAIK

601'  KMLETPGPYLLDIIVPHQEHVLPMIPIGGAFKDMILDGDGRTVY
      ************************* ******************
601"  KMLETPGPYLLDIIVPHQEHVLPMIPSGGAFKDMILDGDGRTVY
```

548: tryptophan (W) → leucine (L)

627: serine (S) → isoleucine (I)

```
1st Nucleotide Sequence
  File Name       : Double-point mutant full length ALS cDNA
2nd Nucleotide Sequence
  File Name       : Wild type full length ALS cDNA 1'           CTCGCCGCCGCCGCCGCCGCCACCACCCACCATGGCTACGACCG
                 *******************************************
    1"  CCCAAACCCAGAAACCCTCGCCGCCGCCGCCGCCACCACCCACCATGGCTACGACCG 45'  CCGCGGCCGCGGCCGCCGCCCTGTCCGCCGCCGCGACGGCCAAGACCGGCCGTAAGAACC
        ************************************************************
   61"  CCGCGGCCGCGGCCGCCGCCCTGTCCGCCGCCGCGACGGCCAAGACCGGCCGTAAGAACC 105'  ACCAGCGACACCACGTCCTTCCCGCTCGAGGCCGGGTGGGGGCGGCGGCGGTCAGGTGCT
        ************************************************************
  121"  ACCAGCGACACCACGTCCTTCCCGCTCGAGGCCGGGTGGGGGCGGCGGCGGTCAGGTGCT 165'  CGGCGGTGTCCCCGGTCACCCCGCCGTCCCCGGCGCCGCCGGCCACGCCGCTCCGGCCGT
        ************************************************************
  181"  CGGCGGTGTCCCCGGTCACCCCGCCGTCCCCGGCGCCGCCGGCCACGCCGCTCCGGCCGT 225'  GGGGGCCGGCCGAGCCCCGCAAGGGCGCGGACATCCTCGTGGAGGCGCTGGAGCGGTGCG
        ************************************************************
  241"  GGGGGCCGGCCGAGCCCCGCAAGGGCGCGGACATCCTCGTGGAGGCGCTGGAGCGGTGCG 285'  GCGTCAGCGACGTGTTCGCCTACCCGGGCGGCGCGTCCATGGAGATCCACCAGGCGCTGA
        ************************************************************
  301"  GCGTCAGCGACGTGTTCGCCTACCCGGGCGGCGCGTCCATGGAGATCCACCAGGCGCTGA 345'  CGCGCTCCCCGGTCATCACCAACCACCTCTTCCGCCACGAGCAGGGCGAGGCGTTCGCGG
        ************************************************************
  361"  CGCGCTCCCCGGTCATCACCAACCACCTCTTCCGCCACGAGCAGGGCGAGGCGTTCGCGG 405'  CGTCCGGGTACGCGCGCGCGTCCGGCCGCGTCGGGGTCTGCGTCGCCACCTCCGGCCCCG
        ************************************************************
  421"  CGTCCGGGTACGCGCGCGCGTCCGGCCGCGTCGGGGTCTGCGTCGCCACCTCCGGCCCCG 465'  GGGCAACCAACCTCGTGTCCGCGCTCGCCGACGCGCTGCTCGACTCCGTCCCGATGGTCG
        ************************************************************
  481"  GGGCAACCAACCTCGTGTCCGCGCTCGCCGACGCGCTGCTCGACTCCGTCCCGATGGTCG 525'  CCATCACGGGCCAGGTCCCCCGCCGCATGATCGGCACCGACGCCTTCCAGGAGACGCCCA
        ************************************************************
  541"  CCATCACGGGCCAGGTCCCCCGCCGCATGATCGGCACCGACGCCTTCCAGGAGACGCCCA 585'  TAGTCGAGGTCACCCGCTCCATCACCAAGCACAATTACCTTGTCCTTGATGTGGAGGACA
        ************************************************************
  601"  TAGTCGAGGTCACCCGCTCCATCACCAAGCACAATTACCTTGTCCTTGATGTGGAGGACA 645'  TCCCCCGCGTCATACAGGAAGCCTTCTTCCTCGCGTCCTCGGGCCGTCCTGGCCCGGTGC
        ************************************************************
  661"  TCCCCCGCGTCATACAGGAAGCCTTCTTCCTCGCGTCCTCGGGCCGTCCTGGCCCGGTGC 705'  TGGTCGACATCCCCAAGGACATCCAGCAGCAGATGGCCGTGCCGGTCTGGGACACCTCGA
        ************************************************************
  721"  TGGTCGACATCCCCAAGGACATCCAGCAGCAGATGGCCGTGCCGGTCTGGGACACCTCGA
```

```
 765' TGAATCTACCAGGGTACATCGCACGCCTGCCCAAGCCACCCGCGACAGAATTGCTTGAGC
      ************************************************************
 781" TGAATCTACCAGGGTACATCGCACGCCTGCCCAAGCCACCCGCGACAGAATTGCTTGAGC

825' AGGTCTTGCGTCTGGTTGGCGAGTCACGGCGCCCGATTCTCTATGTCGGTGGTGGCTGCT
      ************************************************************
 841" AGGTCTTGCGTCTGGTTGGCGAGTCACGGCGCCCGATTCTCTATGTCGGTGGTGGCTGCT

885' CTGCATCTGGTGACGAATTGCGCTGGTTTGTTGAGCTGACTGGTATCCCAGTTACAACCA
      ************************************************************
 901" CTGCATCTGGTGACGAATTGCGCTGGTTTGTTGAGCTGACTGGTATCCCAGTTACAACCA

945' CTCTGATGGGCCTCGGCAATTTCCCCAGTGACGACCCGTTGTCCCTGCGCATGCTTGGGA
      ************************************************************
 961" CTCTGATGGGCCTCGGCAATTTCCCCAGTGACGACCCGTTGTCCCTGCGCATGCTTGGGA

1005' TGCATGGCACGGTGTACGCAAATTATGCCGTGGATAAGGCTGACCTGTTGCTTGCGTTTG
      ************************************************************
1021" TGCATGGCACGGTGTACGCAAATTATGCCGTGGATAAGGCTGACCTGTTGCTTGCGTTTG

1065' GTGTGCGGTTTGATGATCGTGTGACAGGGAAAATTGAGGCTTTTGCAAGCAGGGCCAAGA
      ************************************************************
1081" GTGTGCGGTTTGATGATCGTGTGACAGGGAAAATTGAGGCTTTTGCAAGCAGGGCCAAGA

1125' TTGTGCACATTGACATTGATCCAGCAGAGATTGGAAAGAACAAGCAACCACATGTGTCAA
      ************************************************************
1141" TTGTGCACATTGACATTGATCCAGCAGAGATTGGAAAGAACAAGCAACCACATGTGTCAA

1185' TTTGCGCAGATGTTAAGCTTGCTTTACAGGGCTTGAATGCTCTGCTACAACAGAGCACAA
      ************************************************************
1201" TTTGCGCAGATGTTAAGCTTGCTTTACAGGGCTTGAATGCTCTGCTACAACAGAGCACAA

1245' CAAAGACAAGTTCTGATTTTAGTGCATGGCACAATGAGTTGGACCAGCAGAAGAGGGAGT
      ************************************************************
1261" CAAAGACAAGTTCTGATTTTAGTGCATGGCACAATGAGTTGGACCAGCAGAAGAGGGAGT

1305' TTCCTCTGGGGTACAAAACTTTTTGGTGAAGAGATCCCACCGCAATATGCCATTCAGGTGC
      ************************************************************
1321" TTCCTCTGGGGTACAAAACTTTTTGGTGAAGAGATCCCACCGCAATATGCCATTCAGGTGC

1365' TGGATGAGCTGACGAAAGGTGAGGCAATCATCGCTACTGGTGTTGGGCAGCACCAGATGT
      ************************************************************
1381" TGGATGAGCTGACGAAAGGTGAGGCAATCATCGCTACTGGTGTTGGGCAGCACCAGATGT

1425' GGGCGGCACAATATTACACCTACAAGCGGCCACGGCAGTGGCTGTCTTCGGCTGGTCTGG
      ************************************************************
1441" GGGCGGCACAATATTACACCTACAAGCGGCCACGGCAGTGGCTGTCTTCGGCTGGTCTGG

1485' GCGCAATGGGATTTGGGCTGCCTGCTGCAGCTGGTGCTTCTGTGGCTAACCCAGGTGTCA
      ************************************************************
1501" GCGCAATGGGATTTGGGCTGCCTGCTGCAGCTGGTGCTTCTGTGGCTAACCCAGGTGTCA

1545' CAGTTGTTGATATTGATGGGGATGGTAGCTTCCTCATGAACATTCAGGAGCTGGCATTGA
      ************************************************************
1561" CAGTTGTTGATATTGATGGGGATGGTAGCTTCCTCATGAACATTCAGGAGCTGGCATTGA

1605' TCCGCATTGAGAACCTCCCTGTGAAGGTGATGGTGTTGAACAACCAACATTTGGGTATGG
      ************************************************************
1621" TCCGCATTGAGAACCTCCCTGTGAAGGTGATGGTGTTGAACAACCAACATTTGGGTATGG
```

Fig. 2 (continued)

```
1665'  TGGTGCAATTGGAGGATAGGTTTTACAAGGCGAATAGGGCGCATACATACTTGGGCAACC
       ********  **************************************************
1681"  TGGTGCAATGGGAGGATAGGTTTTACAAGGCGAATAGGGCGCATACATACTTGGGCAACC

1725'  CGGAATGTGAGAGCGAGATATATCCAGATTTTGTGACTATTGCTAAGGGGTTCAATATTC
       ************************************************************
1741"  CGGAATGTGAGAGCGAGATATATCCAGATTTTGTGACTATTGCTAAGGGGTTCAATATTC

1785'  CTGCAGTCCGTGTAACAAAGAAGAGTGAAGTCCGTGCCGCCATCAAGAAGATGCTCGAGA
       ************************************************************
1801"  CTGCAGTCCGTGTAACAAAGAAGAGTGAAGTCCGTGCCGCCATCAAGAAGATGCTCGAGA

1845'  CTCCAGGGCCATACTTGTTGGATATCATCGTCCCGCACCAGGAGCATGTGCTGCCTATGA
       ************************************************************
1861"  CTCCAGGGCCATACTTGTTGGATATCATCGTCCCGCACCAGGAGCATGTGCTGCCTATGA

1905'  TCCCAATTGGGGGCGCATTCAAGGACATGATCCTGGATGGTGATGGCAGGACTGTGTATT
       ******  ****************************************************
1921"  TCCCAAGTGGGGGCGCATTCAAGGACATGATCCTGGATGGTGATGGCAGGACTGTGTATT

1965'  AATCTATAATCTGTATGTTGGCAAAGCACCAGCCCGGCCTATGTTTGACCTGAATGACCC
       ************************************************************
1981"  AATCTATAATCTGTATGTTGGCAAAGCACCAGCCCGGCCTATGTTTGACCTGAATGACCC

2025'  ATAAAGAGTGGTATGCCTATGATGTTTGTATGTGCTCTATCAATAACTAAGGTGTCAACT
       ************************************************************
2041"  ATAAAGAGTGGTATGCCTATGATGTTTGTATGTGCTCTATCAATAACTAAGGTGTCAACT

2085'  ATGAACCATATGCTCTTCTGTTTTACTTGTTTGATGTGCTTGGCATGGTAATCCTAATTA
       ************************************************************
2101"  ATGAACCATATGCTCTTCTGTTTTACTTGTTTGATGTGCTTGGCATGGTAATCCTAATTA

2145'  GCTTCCTGCTGTCTAGGTTTGTAGTGTGTTGTTTTCTGTAGGCATATGCATCACAAGATA
       ************************************************************
2161"  GCTTCCTGCTGTCTAGGTTTGTAGTGTGTTGTTTTCTGTAGGCATATGCATCACAAGATA

2205'  TCATGTAAGTTTCTTGTCCTACATATCAATAATAAGAGAATAAAGTACTTCTATGTAAAA
       ********************************************************  **
2221"  TCATGTAAGTTTCTTGTCCTACATATCAATAATAAGAGAATAAAGTACTTCTATGCAAAA

2265'  AAAAAAAAAAAAAAA
       ***************
2281"  AAAAAAAAAAAAAAAAAAAAAAA
```

Chlorsulfuron concentration

Chlorsulfuron concentration

—□— Acetoin generation activity after 60 min of reaction (stopped with sulfuric acid)

—♦— Acetoin generation activity after 0 min of reaction (stopped with sulfuric acid)

Fig. 11

1st Nucleotide Sequence
  File Name      : Nipponbare ALS partial cDNA
  Sequence Size  : 1505

2nd Nucleotide Sequence
  File Name      : X63554 maize ALS 1
  Sequence Size  : 2544

```
      1'                                         ACCCACGCGTCCGATGTGGAGGA
                                                 *** ** ** ** **
   1141" CATCGTCGAGGTCACCCGCTCCATCACCAAGCACAACTACCTGGTCCTCGACGTCGACGA

24' CATCCCCCGCGTCATACAGGAAGCCTTCTTCCTCGCGTCCTCGGGCCGTCCTGGCCCGGT
         ************* * ***** ************** ***** ** ** ** ** *****
   1201" CATCCCCCGCGTCGTGCAGGAGGCCTTCTTCCTCGCATCCTCTGGTCGCCCGGGGCCGGT

84' GCTGGTCGACATCCCCAAGGACATCCAGCAGCAGATGGCCGTGCCGGTCTGGGACACCTC
         *** ** ************************************ ******* ********** *
   1261" GCTTGTTGACATCCCCAAGGACATCCAGCAGCAGATGGCGGTGCCGGCCTGGGACACGCC

144' GATGAATCTACCAGGGTACATCGCACGCCTGCCCAAGCCACCCGCGACAGAATTGCTTGA
         ****  ***  ** ************ ***** ********* ****** ****** *****
   1321" CATGAGTCTGCCTGGGTACATCGCGCGCCTTCCCAAGCCTCCCGCGACTGAATTTCTTGA

204' GCAGGTCTTGCGTCTGGTTGGCGAGTCACGGCGCCCGATTCTCTATGTCGGTGGTGGCTG
         ******  ********* ***** ** ************* **** ***** ** ***********
   1381" GCAGGTGCTGCGTCTTGTTGGTGAATCACGGCGCCCTGTTCTTTATGTTGGCGGTGGCTG

264' CTCTGCATCTGGTGACGAATTGCGCTGGTTTGTTGAGCTGACTGGTATCCCAGTTACAAC
         *  ***** ***** ** *** ** * ***** *** ************ ************ *****
   1441" TGCAGCATCAGGTGAGGAGTTGTGCCGCTTTGTGGAGTTGACTGGAATCCCAGTCACAAC

324' CACTCTGATGGGCCTCGGCAATTTCCCCAGTGACGACCCGTTGTCCCTGCGCATGCTTGG
         ****** ********* ***** ******** ********* **** ****************
   1501" TACTCTTATGGGCCTTGGCAACTTCCCCAGCGACGACCCACTGTCACTGCGCATGCTTGG

384' GATGCATGGCACGGTGTACGCAAATTATGCCGTGGATAAGGCTGACCTGTTGCTTGCGTT
         *************  ***** ************* ************ ** ************* **
   1561" TATGCATGGCACAGTGTATGCAAATTATGCAGTGGATAAGGCCGATCTGTTGCTTGCATT

444' TGGTGTGCGGTTTGATGATCGTGTGACAGGGAAAATTGAGGCTTTTGCAAGCAGGGCCAA
         ****************************************************** **** ** **
   1621" TGGTGTGCGGTTTGATGATCGTGTGACAGGGAAAATTGAGGCTTTTGCAGGCAGAGCTAA

504' GATTGTGCACATTGACATTGATCCAGCAGAGATTGGAAAGAACAAGCAACCACATGTGTC
         *************** ******** ** ******** ************* **********
   1681" GATTGTGCACATTGATATTGATCCTGCTGAGATTGGCAAGAACAAGCAGCCACATGTGTC

564' AATTTGCGCAGATGTTAAGCTTGCTTTACAGGGCTTGAATGCTCTGCTACAACAGAGCAC
         ** ** ****************** ****** ***** **** ** **  *****
   1741" CATCTGTGCAGATGTTAAGCTTGCTTTGCAGGGCATGAATACTCTTCTGGAAGGAAGCAC
```

Fig. 11 (continued)

```
 624' AACAAAGACAAGTTCTGATTTTAGTGCATGGCACAATGAGTTGGACCAGCAGAAGAGGGA
      * ******  ** * *** **   *  *******  ****  *****  *****  ********
1801" ATCAAAGAAGAGCTTTGACTTCGGCTCATGGCATGATGAATTGGATCAGCAAAAGAGGGA

684' GTTTCCTCTGGGGTACAAAACTTTTTGGTGAAGAGATCCCACCGCAATATGCCATTCAGGT
      ******  ** ** **** **    *** ** ****  ** ********  ********
1861" GTTTCCCCTTGGATATAAAATCTTCAATGAGGAAATCCAGCCACAATATGCTATTCAGGT

744' GCTGGATGAGCTGACGAAAGGTGAGGCAATCATCGCTACTGGTGTTGGGCAGCACCAGAT
      ** ****** ******* ** ***** *****  ** **  *********************
1921" TCTTGATGAGTTGACGAAGGGGGAGGCCATCATTGCCACAGGTGTTGGGCAGCACCAGAT

804' GTGGGCGGCACAATATTACACCTACAAGCGGCCACGGCAGTGGCTGTCTTCGGCTGGTCT
      ************  ********  *************  *****************  ********
1981" GTGGGCGGCACAGTATTACACTTACAAGCGGCCAAGGCAGTGGCTGTCTTCAGCTGGTCT

864' GGGCGCAATGGGATTTGGGCTGCCTGCTGCAGCTGGTGCTTCTGTGGCTAACCCAGGTGT
      **  **  *************  ****  *****  *******  ********  ************
2041" TGGGGCTATGGGATTTGGTTTGCCGGCTGCTGCTGGTGCTGCTGTGGCCAACCCAGGTGT

924' CACAGTTGTTGATATTGATGGGGATGGTAGCTTCCTCATGAACATTCAGGAGCTGGCATT
      *** *********  ** ** **************************************  *  *
2101" CACTGTTGTTGACATCGACGGAGATGGTAGCTTCCTCATGAACATTCAGGAGCTAGCTAT

984' GATCCGCATTGAGAACCTCCCTGTGAAGGTGATGGTGTTGAACAACCAACATTTGGGTAT
      ******  ************** ***** *   * ***  * ********  **  * ** **
2161" GATCCGTATTGAGAACCTCCCAGTCAAGGTCTTTGTGCTAAACAACCAGCACCTCGGGAT

1044' GGTGGTGCAATGGGAGGATAGGTTTTACAAGGCGAATAGGGCGCATACATACTTGGGCAA
      *********  ***********  *****  *****  ** ** ****  ******  **
2221" GGTGGTGCAGTGGGAGGACAGGTTCTATAAGGCCAATAGAGCACACACATTCTTGGGAAA

1104' CCCGGAATGTGAGAGCGAGATATATCCAGATTTTGTGACCTATTGCTAAGGGGTTCAATA
      ***  **  ** **  *******************  *   ********  ******** *
2281" CCCAGAGAACGAAAGTGAGATATATCCAGATTTTGTG-GCAATTGCTAAAGGGTTCAACA

1164' TTCCTGCAGTCCGTGTAACAAAGAAGAGTGAAGTCCGTGCCGCCATCAAGAAGATGCTCG
      ****  *********** ************  *******  *** **  ************** *
2340" TTCCAGCAGTCCGTGTGACAAAGAAGAGCGAAGTCCATGCAGCAATCAAGAAGATGCTTG

1224' AGACTCCAGGGCCATACTTGTTGGATATCATCGTCCCGCACCAGGAGCATGTGCTGCCTA
      ** **********  *** * ******* *********************************  ******
2400" AGGCTCCAGGGCCGTACCTCTTGGATATAATCGTCCCGCACCAGGAGCATGTGTTGCCTA

1284' TGATCCCAAGTGGGGGCGCATTCAAGGACATGATCCTGGATGGTGATGGCAGGACTGTGT
      *******  *****  ** ** ****************************************
2460" TGATCCCTAGTGGTGGGGCTTTCAAGGATATGATCCTGGATGGTGATGGCAGGACTGTGT

1344' ATTAATCTATAATCTGTATGTTGGCAAAGCACCAGCCCGGCCTATGTTTGACCTGAATGA
      *** ***   *   *** * ** * *
2520" ATTGATCCGTTGACTGCAGGTCGAC
```

GENE ENCODING ACETOLACTATE SYNTHASE

This application is the national phase under 35 U.S.C. § 371 of PCT International Application No. PCT/JP01/10014 which has an International filing date of Nov. 16, 2001, which designated the United States of America.

FIELD OF THE INVENTION

The present invention relates to a gene encoding acetolactate synthase which is a rate-determining enzyme in the branched-chain amino acid biosynthetic pathway.

BACKGROUND OF THE INVENTION

Acetolactate synthase (hereinafter referred to as "ALS") is a rate-determining enzyme in the biosynthetic pathway of branched chain amino acids, such as leucine, valine and isoleucine, and is known as an essential enzyme for the growth of plants. ALS is also known to be present in a wide variety of higher plants. In addition, ALS is found in various microorganisms, such as yeast (*Saccharomyces cerevisiae*), *Escherichia coli*, and *Salmonella typhimurium*.

Three types of isoenzymes of ALS are known to be present in *Escherichia coli* and *Salmonella typhimurium*. Each of these isoenzymes is a hetero oligomer consisting of catalytic subunits with a large molecular weight that governs catalytic activity of the enzyme and regulatory subunits with a small molecular weight that functions as regulatory proteins by binding of branched-chain amino acids (Chipman et al., Biochim. Biophys. Acta. 1385, 401–419, 1998). Catalytic subunits are located at Ilv IH, Ilv GM and Ilv BN operons, respectively. On the other hand, ALS in yeast is a single enzyme, which comprises a catalytic subunit and a regulatory subunit, as is the case in bacteria (Pang et al., Biochemistry, 38, 5222–5231, 1999). The catalytic protein subunit is located at the locus ILV2.

In plants, ALS is known to comprise catalytic subunit(s) and regulatory subunit(s) as is the case in the above microorganisms (Hershey et al., Plant Molecular Biology. 40, 795–806, 1999). For example, the catalytic subunit of ALS in tobacco (dicotyledon) is encoded by two gene loci, SuRA and SuRB (Lee et al., EMBO J. 7, 1241–1248, 1988); that in maize is encoded by two gene loci, als 1 and als 2 (Burr et al., Trendsin Genetics 7, 55–61, 1991; Lawrence et al., Plant Mol. Biol. 18, 1185–1187, 1992). The nucleotide sequences of genes encoding a catalytic subunit have been completely determined for dicotyledonous plants including tobacco, Arabidopsis, rapeseed, cotton, Xanthium, Amaranthus and Kochia (See Chipman et al., Biochim. Biophys. Acta. 1385, 401–419, 1998 and domestic re-publication of PCT international publication for patent applications WO97/08327). However, maize is the only monocotyledonous plant whose nucleotide sequence has been completely determined.

Herbicides, for example, sulfonylurea herbicides, imidazolinon herbicides, triazolopyrimidine herbicides and pyrimidinyl carboxy herbicides (hereinafter referred to as "PC herbicides") are known to suppress the growth of a plant by inhibiting ALS (Ray, Plant Physiol. 75, 827–831, 1984; Shaner et al., Plant Physiol.76, 545–546, 1984; Subramanian et al., Plant Physiol. 96, 310–313, 1991; Shimizu et al., J. Pestic. Sci.19, 59–67, 1994).

Known plants having resistance to these herbicides contain a gene encoding ALS that includes substitution of one or two nucleotides which induces substitution of one or two amino acids in a region conserved among different species. Examples of such a gene include a gene encoding ALS having resistance specific to sulfonylurea herbicides (see Kathleen et al., EMBO J. 7,1241–1248, 1988; Mourad et al., Planta, 188, 491–497, 1992; Guttieri et al., Weed Sci. 43,175–178, 1995; Bernasconi et al., J. Biol. Chem. 270, 17381–17385, 1995 and Japanese Patent Application Laying-Open (kokai) No. 63-71184); a gene encoding ALS having resistance specific to imidazolinon herbicides (Mourad et al., Planta, 188, 491–497, 1992; Lee et al., FEBS Lett. 452,341–345, 1999 Japanese Patent Application Laying-Open (kokai) No. 5-227964); and a gene encoding ALS having resistance to both sulfonylurea and imidazolinon herbicides (see Kathleen et al., EMBO J. 7,1241–1248, 1988; Bernasconi et al., J. Biol. Chem. 270, 17381–17385, 1995; Hattori et al., Mol. Gen. Genet. 246,419–425, 1995; Alison et al., Plant Physiol. 111, 1353, 1996; Rajasekarau et al., Plant Sci. 119, 115–124, 1996, Japanese Patent Application Laying-Open (kokai) No.63-71184, Japanese Patent Application Laying-Open (kokai) No.4-311392 and Bernasconi et al., U.S. Pat. No. 5,633,437, 1997). ALS showing resistance to both sulfonylurea and imidazolinon herbicides is also known to show cross resistance to PC herbicides and triazolopyrimidine herbicides (Bernasconi et al., J. Biol. Chem. 270, 17381–17385, 1995). Further, the production of a plant body showing resistant to both sulfonylurea and imidazolinon herbicides has been attempted by crossing a plant having ALS showing resistance specific to sulfonylurea herbicides with a plant having ALS showing resistance specific to imidazolinon herbicides (Mourad et al., Mol. Gen. Genet, 243, 178–184, 1994). Furthermore, artificial alteration of a gene encoding ALS into a herbicide resistance gene has been attempted (Ott et al., J. Mol. Biol. 263, 359–368, 1996, Japanese Patent Application Laying-Open (kokai) No. 63-71184, Japanese Patent Application Laying-Open (kokai) No. 5-227964, Japanese Patent Application Laying-Open (kohyo) No. 11-504213) so that it has been found that a single amino acid deletion causes ALS to show resistance to both sulfonylurea and imidazolinon herbicides (see Japanese Patent Application Laying-Open (kokai) No. 5-227964).

As described above, ALSs having resistance to herbicides and genes encoding ALS have been aggressively studied. However, there has been no report directed toward resistance to PC herbicides and concerning a mutant ALS gene having resistance specific to a PC herbicide.

SUMMARY OF THE INVENTION

The purpose of the present invention is to provide a gene encoding an ALS protein showing extremely high resistance to PC herbicides, the ALS protein encoded by the gene, a recombinant vector having the gene, a transformant having the recombinant vector, a plant having the gene, a method for rearing the plant, and a method for selecting a transformant cell using the gene as a selection marker.

As a result of thorough studies to achieve the above purpose, we have completed the present invention by finding that a mutant ALS, which is derived from the wild type ALS by substituting a certain amino acid residue of the wild type ALS with a certain amino acid, shows extremely high resistance to PC herbicides.

(1) The present invention is a gene which encodes the following protein (a) or (b):

(a) a protein comprising an amino acid sequence of SEQ ID NO: 1;

(b) a protein comprising an amino acid sequence derived from the amino acid sequence of SEQ ID NO: 1 by substitution, deletion or addition of at least one or more amino acids, which has resistance to pyrimidinyl carboxy herbicides and has acetolactate synthase activity.

(2) Further, the present invention is an acetolactate synthase protein which is encoded by the gene of (1).

(3) Furthermore, the present invention is a recombinant vector which has the gene of (1).

(4) Further, the present invention is a transformant which has the recombinant vector of (3).

(5) Moreover, the present invention is a plant which has the gene of (1) and has resistance to pyrimidinyl carboxy herbicides.

(6) The present invention is a method for rearing the plant of (5) which comprises rearing the plant in the presence of a pyrimidinyl carboxy herbicide.

(7) The present invention is a method for selecting a transformant cell having the gene of (1) using this gene as a selection marker.

BRIEF DESCRIPTION OF THE DRAWINGS

FIG. 1 shows a comparison between the amino acid sequence of a mutant ALS protein and that of a wild type ALS protein. (SEQ ID NO:12).

FIG. 2 shows a comparison between the nucleotide sequence of a mutant ALS gene and that of a wild type ALS gene.

FIG. 11 shows a comparison of nucleotide sequences between Nippon-bare EST and maize ALS gene.

DETAILED DESCRIPTION OF THE INVENTION

Figure 3:
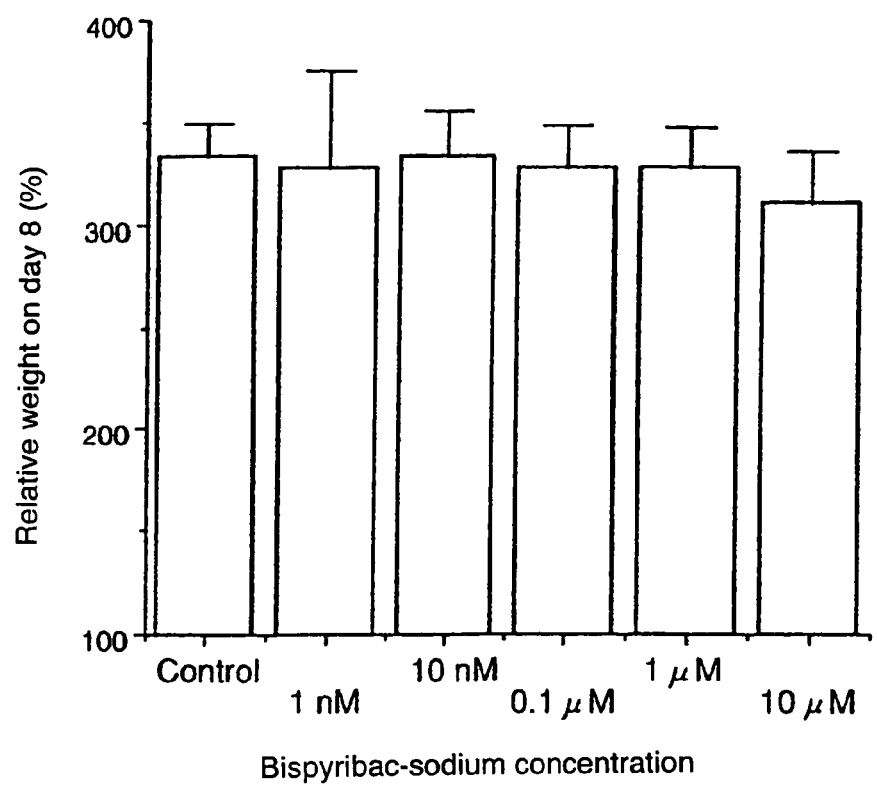
FIG. 3 is a characteristic figure showing sensitivity of the resistant mutant to bispyribac-sodium.

A more detailed explanation will be given of the present invention.

The acetolactate synthase protein of the present invention (hereinafter referred to as "mutant ALS protein") can be obtained by mutating a certain site in a wild type ALS protein expressed in a rice plant. The amino acid sequence of the mutant ALS protein of the present invention is represented by SEQ ID NO: 1. The nucleotide sequence of the gene encoding the ALS protein of the present invention is represented by SEQ ID NO: 2.

The mutant ALS protein is derived from a wild type ALS protein by substituting tryptophan 548 with leucine and substituting serine 627 with isoleucine. FIG. 1 shows the result of comparison of the amino acid sequence of the mutant ALS protein and that of the wild type ALS protein. In FIG. 1, the amino acid sequence in the first row shows the mutant ALS protein and that in the second row shows the wild type ALS protein.

Compared to a gene encoding the wild type ALS protein, a gene (SEQ ID NO: 2) encoding the mutant ALS protein contains substitution of a codon encoding tryptophan 548 with a codon encoding leucine and substitution of a codon encoding a serine 627 with a codon encoding isoleucine. FIG. 2 shows the result of comparison of the nucleotide sequence of the gene encoding the mutant ALS protein and that encoding the wild type ALS protein. In FIG. 2, the nucleotide sequence in the first row shows the mutant ALS protein and that in the second row shows the wild type ALS protein.

A gene encoding the mutant ALS protein can be obtained by introducing a mutation as described above into a gene encoding a wild type ALS protein which is present in the genome DNA of japonica type rice variety, Kinmaze. To introduce mutations, known standard techniques can be employed. For example, site-directed mutagenesis can be used. Site-directed mutagenesis can be performed using a commercial kit, e.g. Mutan-K (Takara Shuzo), Gene Editor (Promega) or Exsite (Stratagene).

In addition, a gene encoding the mutant ALS protein can be obtained by culturing wild type culture cells sensitive to PC herbicides in the presence of a PC herbicide and then selecting mutant culture cells that emerge and show resistance to the PC herbicide.

First, mRNAs is prepared from mutant culture cells resistant to a PC herbicide, cDNAs are synthesized, and then a cDNA library (which is thought to have heterozygosity for resistance property), of λgt 11 phage is produced. Then, the library is screened using a nucleic acid probe [EST (Expression Sequence Tag, Genbank, DDBJ and EMBL Accession No. C72411) obtained from japonica type rice variety, Nippon-bare] containing part of a gene encoding the wild type ALS protein. Next, the insert DNA of the resulting positive clone is subcloned into pBluescript II SK+, to determine the nucleotide sequence. Selection of a clone having the insert DNA which encodes the amino acid sequence of SEQ ID NO: 1 enables a gene encoding a mutant ALS protein to be obtained. In addition, a plasmid comprising pBluescript II SK+ into which a gene encoding mutant ALS protein had been incorporated was deposited to Patent and Bio-Resource Center, National Institute of Advanced Industrial Science and Technology (Chuo-6, 1-1-1, Higashi, Tsukuba-shi, Ibaraki, JAPAN) as Mutant ALS cDNA in pBluescript II SK+ (FERM BP-7348) on Nov. 2, 2000 under the Budapest Treaty.

Compared to the wild type ALS protein, the mutant ALS protein possesses good resistance not only to PC herbicides, but also to sulfonylurea and imidazolinon herbicides. Particularly, the mutant ALS protein possesses a high level of resistance to a PC herbicide. It can be determined by incorporating a gene encoding the mutant ALS protein into an expression vector of e.g. E. coli, and examining sensitivity to the herbicide of E. coli transformed with the expression vector.

Examples of a PC herbicide include bispyribac-sodium, pyrithiobac-sodium and pyriminobac as represented by the following chemical formula 1.

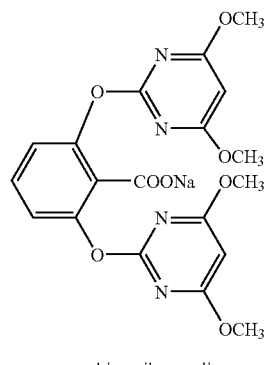

bispyribac-sodium

-continued

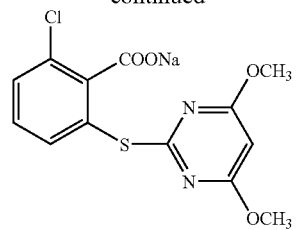

pyrithiobac-sodium

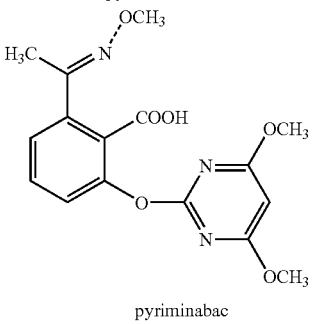

pyriminabac

Examples of a sulfonylurea herbicide include chlorsulfuron, bensulfuron-methyl, pyrazosulfuron-ethyl, and imazosulfuron as represented by the following chemical formula 2.

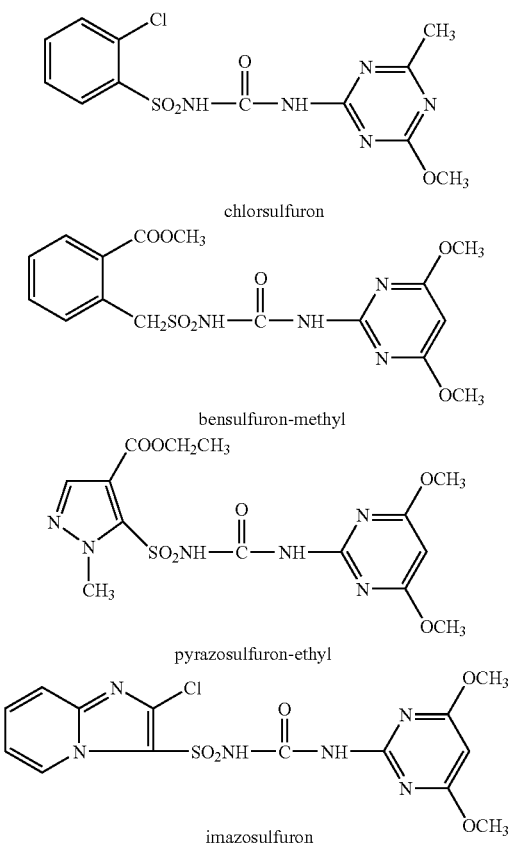

Examples of an imidazolinon herbicide include imazaquin and imazapyr as represented by the following chemical formula 3.

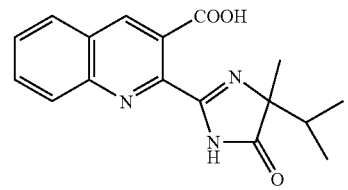

imazaquin

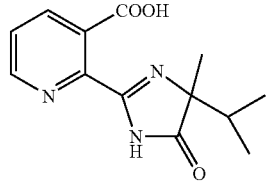

imazapyr

Transformation of a target plant using a gene encoding the mutant ALS protein can impart resistance to PC herbicides to the plant. Known standard techniques can be used for transformation of a plant. For example, a foreign gene can be introduced into a target plant cell using *Agrobacterium tumefaciens*.

More specifically, a gene encoding the mutant ALS protein is inserted into a binary vector containing T-DNA sequence of a Ti plasmid of Agrobacterium. The Ti plasmid is transformed into *E. coli* and the like. Then, the binary vectors containing the gene encoding the mutant ALS protein replicated by e.g. *E. coli* are transformed into Agrobacteria which contain helper plasmids. Target plants are infected with the Agrobacteria, and then the transformed plants are identified. When the identified transformed plant is a culture cell, the plant cell can be regenerated into a complete plant by known standard techniques.

To transform a target plant with a gene encoding the mutant ALS protein, the gene can be directly introduced using known standard techniques. Examples of a method which transforms an expression vector containing a gene encoding the mutant ALS protein include the polyethylene glycol method, electroporation, and particle gun method.

A gene encoding the mutant ALS protein may be transformed into any type of plants, such as monocotyledonous and dicotyledonous plants. Examples of a target crop into which a gene encoding the mutant ALS protein is transformed include rice, maize, wheat, barley, soybean, cotton, rapeseeds, sugar beet and tobacco. In addition, turf grass, trees and the like can be transformed by introducing a gene encoding the mutant ALS protein.

In any of the above cases, transformation of a plant using a gene encoding the mutant ALS protein can impart resistance to PC herbicides, sulfonylurea herbicides, and imidazolinon herbicides to the plant.

Moreover, a gene encoding the mutant ALS protein can also be used as a selection marker in an experiment for transformation of a plant. For example to transform a plant cell using a gene of interest, a vector which contains a gene encoding the mutant ALS protein and a gene of interest is introduced into the plant cell, followed by culturing of the plant cell under the presence of a PC herbicide. Therefore, a plant cell which survives in the presence of a PC herbicide indicates that it contains a gene encoding the mutant ALS protein and the gene of interest introduced therein. Further, whether a gene of interest and a gene encoding the mutant ALS protein are incorporated into the chromosome of a plant cell can be confirmed by observing the phenotype of the plant and then examining the presence of these genes on the genome by genome southern hybridization or PCR.

EXAMPLES

Now, the present invention will be further described by the following examples, but the technical scope of the invention is not limited by these examples.

Example 1

Production of Rice (Kinmaze) Culture Cells Resistant to a PC Herbicide

Chaff was removed from rice seeds (variety; Kinmaze, scientific name: *Oryza sativa* var. Kinmaze). The seeds were immersed in 70% ethanol for 5 min, and then immersed in about 5% antiformin for 20 min, followed by washing several times with sterile distilled water. Then, the seeds were static-cultured on a medium with a composition as shown in Table 1.

TABLE 1

| | |
|---|---|
| Inorganic salt (mixed saline for Murashige-Skoog medium) | 1 pack |
| Thiamin · HCl (0.1 g/l) | 1 ml |
| Nicotinic acid (0.5 g/l) | 1 ml |
| Pyridoxine · HCl (0.5 g/l) | 1 ml |
| Glycine (2 g/l) | 1 ml |
| Myo-inositol (50 g/l) | 2 ml |
| 2,4-D (200 ppm) | 10 ml |
| Sucrose | 30 g |

In the above medium composition, 2,4-D is synthesized auxin. To prepare the medium, first, a medium with the above composition was placed in a 1 l beaker, and distilled water was added to the beaker to 1000 ml. Next, the solution was adjusted to pH 5.7, and supplemented with 3 g of Gelrite. The Gelrite was dissolved well by heating with a microwave oven, and then the mixture was added 30 ml at a time to culture flasks using a pipetter. Next, three sheets of aluminum foil were laid over the culture flask, followed by heating for sterilization in an autoclave at 121° C. for 15 to 20 min. Finally the solution was cooled to room temperature so that the media for static culture of the above seeds were prepared.

Next, endosperm portions were removed from the callus induced on the medium, and then subculture was performed. Then, part of the obtained calli was sub-cultured, that is, cultured successively once per two weeks in a liquid medium (the composition is the same as in that shown in Table 1, but not supplemented with Gelrite) supplemented with 1 µM bispyribac-sodium (one of PC herbicides). Two to 6 weeks later, the culture cells started to wither. About 2 months later, a plurality of non-discolored cell masses that were thought to be conducting cell division were obtained from among culture cell populations most of which had died and became discolored brown. These cell masses were isolated and cultured, so that a plurality of cell lines that can proliferate in the presence of 2 µM bispyribac-sodium were obtained.

Subsequently, the resulting plurality of cell lines were cultured while elevating the concentration of bispyribac-sodium in an orderly manner. As a result, cell lines that can proliferate in the presence of 100 µM bispyribac-sodium were obtained. The bispyribac-sodium resistant culture cells (hereinafter referred to as resistant mutant) were sub-cultured on MS-2,4-D solid media supplemented with 100 µM bispyribac-sodium. Part of the sub-cultured resistant mutant was sampled, added into MS-2,4-D liquid media not supplemented with bispyribac-sodium, and then subjected to suspended cell culture at a cycle of 8 to 10 days.

Figure 4:
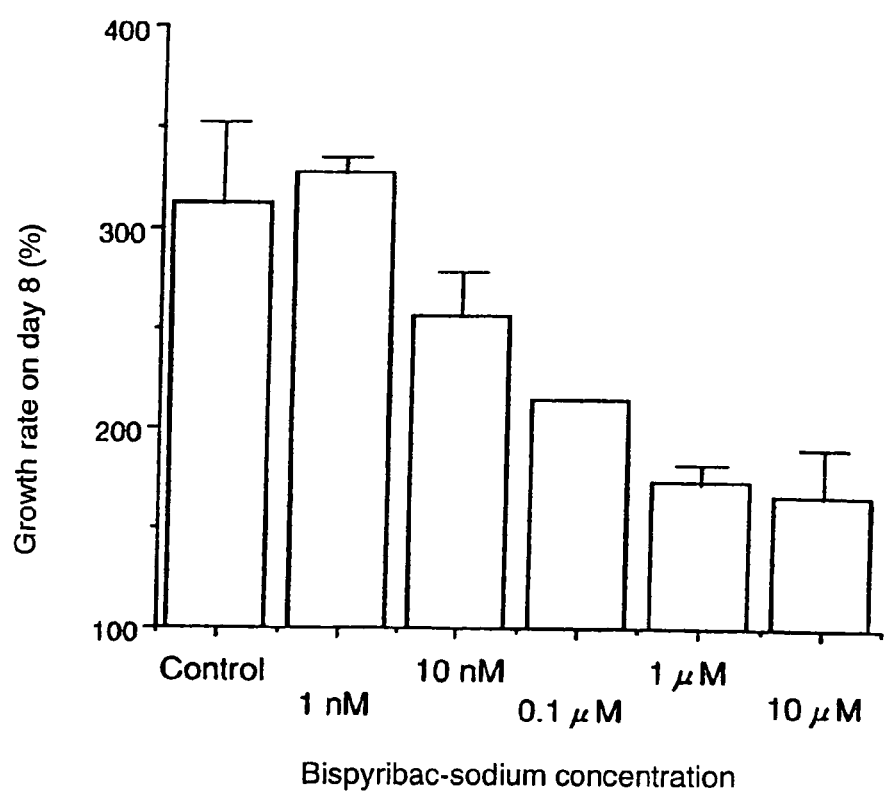
FIG. 4 is a characteristic figure showing sensitivity of the wild type to bispyribac-sodium.

Approximately 1.5 g (wet weight) of the resistant mutant was transplanted in 200 ml of a Erlenmeyer flask supplemented with 50 ml of a MS-2,4-D liquid medium and bispyribac-sodium at an appropriate concentration, followed by culturing at approximately 27° C. for an appropriate period. The wet weight of the callus was measured periodically. The relative amount of increase was determined based on the wet weight of the transplanted resistant mutant. In addition, the experiment was performed three times with different bispyribac-sodium concentrations, and the standard error was calculated. FIG. 3 shows the relation of changes in bispyribac-sodium concentration and the relative weight on day 8 in the resistant mutant. As a control, a similar experiment was conducted using the wild type (Kinmaze). FIG. 4 shows the result of measuring the relation of bispyribac-sodium concentration and relative weight on day 8.

As shown in FIG. 4, the growth of the wild type was not inhibited in a group supplemented with 1 nM bispyribac-sodium, but was inhibited in a group supplemented with 10 nM or more bispyribac-sodium. However as shown in FIG. 3, almost none of the growth of the resistant mutant was affected even in a group supplemented with 10 µM bispyribac-sodium.

Figure 5:
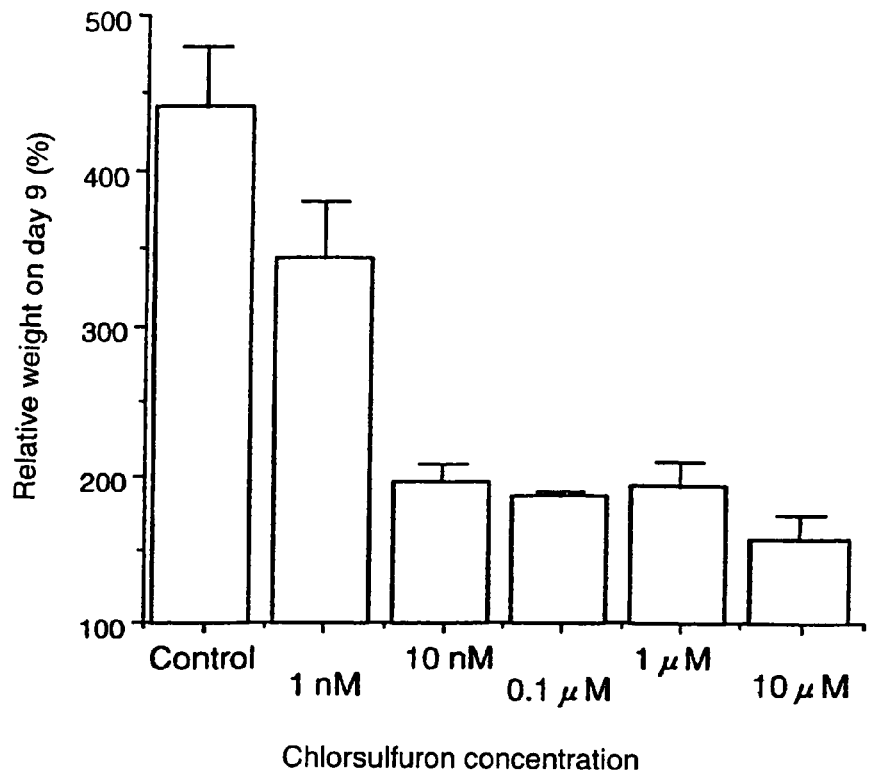
FIG. 5 is a characteristic figure showing sensitivity of the wild type to chlorsulfuron.
Figure 6:
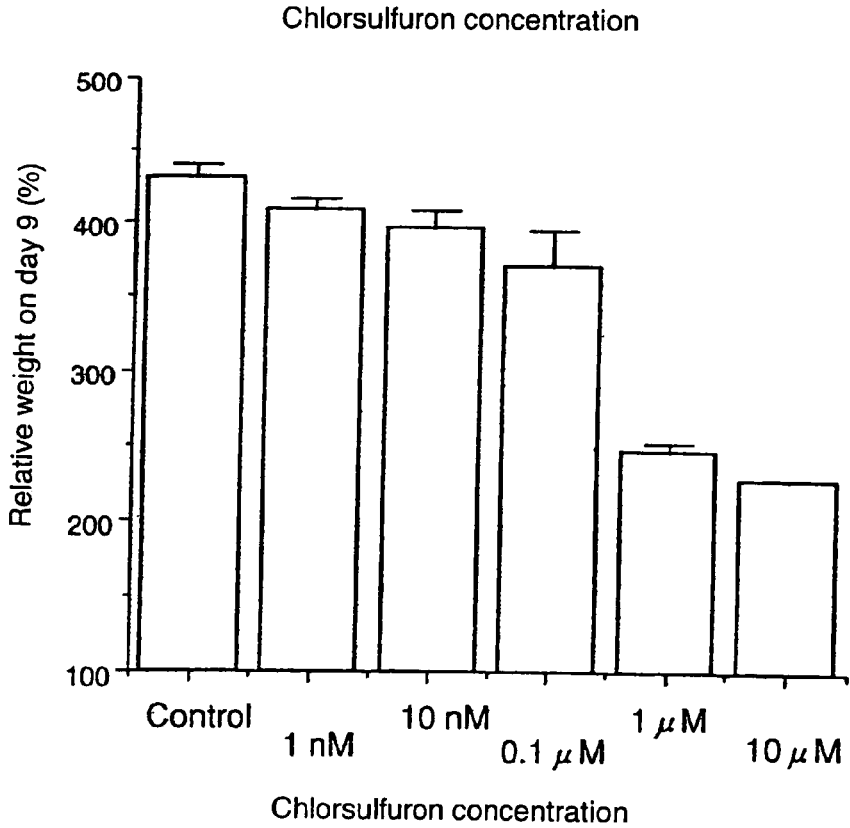
FIG. 6 is a characteristic figure showing sensitivity of the resistant mutant to chlorsulfuron.

The growth rates of the wild type and the resistant mutant were measured as described above except for the use of chlorsulfuron instead of bispyribac-sodium. FIG. 5 shows the relation of changes in chlorsulfuron concentration and relative weight on day 9 in the wild type. FIG. 6 shows the relation of changes in chlorsulfuron concentration and relative weight on day 9 in the resistant mutant.

As shown in FIG. 5, the growth of the wild type was inhibited by addition of 1 nM chlorsulfuron, showing that the wild type has higher sensitivity to chlorsulfuron than to bispyribac-sodium. However, as shown in FIG. 6, the growth of the resistant mutant was strongly inhibited by addition of 1 µM chlorsulfuron. Sensitivity to bispyribac-sodium and chlorsulfuron remained almost unchanged in both the wild type and the resistant mutant, even with longer culture duration. The growth rate was almost the same in the wild type and the resistant mutant.

These results revealed that the resistant mutant possesses resistance specific to bispyribac-sodium. Moreover, the resistant mutant was shown to have improved resistance to chlorsulfuron compared to the wild type.

Example 2

Herbicide Sensitivity of ALS Enzyme Partially Purified From the Resistant Mutant In this example, mutant ALS protein was partially purified from the resistant mutant obtained in Example 1, and then herbicide sensitivity of the obtained mutant ALS protein was examined. The mutant ALS protein was partially purified as follows.

First, 200 g or more of resistant mutant was prepared by a liquid culture method (no supplementation with bispyribac-sodium), the culture having a composition as shown in Table 1 but without Gelrite. Then, about 150 g of the resistant mutant was homogenized using Hiscotron in a volume of buffer-1 [100 mM potassium phosphate buffer (pH 7.5) containing 20% (v/v) glycerol, 0.5 mM thiamin pyrophosphate (TPP), 10 µM flavin adenine dinucleotide (FAD), 0.5 mM MgCl$_2$, and a volume of polyvinyl polypyrrolidone one-tenth that of tissue volume] 3-fold greater than tissue volume. The homogenate was filtered through nylon gauze, and then centrifuged at 15,000×g for 20 min. Ammonium sulfate was added to the centrifuged supernatant to 50% saturation, and then allowed to stand in ice for approximately 1 hour. The mixture was again centrifuged at 15,000×g for 20 min, and then the precipitated fraction was dissolved in about 30 ml of buffer-2 [10 mM Tris hydrochloric acid buffer (pH 7.5) containing 20% (v/v) glycerol, 0.5 mM TPP and 0.5 mM MgCl$_2$]. The mixture was again centrifuged at 15,000×g for 20 min, and then the supernatant fraction was applied to a Sephadex G-25 (Amersham Pharmacia Biotec). About 40 ml of the fraction that had passed through the column was collected as a crude enzyme solution.

Next, the protein concentration of the crude enzyme solution was measured by the Bradford method according to the manual of Bio-Rad Protein Assay. The crude enzyme solution was then filtered through a Whatman filter (Whatman), and then the crude enzyme solution in an appropriate protein amount (10 to 15 ml) was applied to three vertically-connected HiTrap Q columns (Amersham Pharmacia Biotec) using a FPLC device (Amersham Pharmacia Biotec). After protein component was adsorbed using HiTrap Q, unadsorbed fractions were washed out using buffer-2 having a volume 3 to 5 fold greater than the bed volume. Then, the adsorbed protein component was eluted using an eluate having a volume 10 fold greater than the bed volume (150 ml). Here, the eluate was prepared by dissolving KCl with a linear concentration gradient (0 to 0.4 M) into buffer-2. The eluate containing the eluted protein component was apportioned, 5 ml each, into a plurality of test tubes for apportion. Further, to stabilize ALS enzyme contained in the eluted protein component, 0.5 ml of buffer-2 containing 20 mM sodium pyruvate had been previously added to each test tube for apportion.

ALS activity resulting from the mutant ALS protein contained in the eluted fractions apportioned into each test tube for apportion was measured as follows. A reaction solution to be used in a measurement reaction was prepared by mixing an eluted fraction to be measured with a solution comprising 20 mM sodium pyruvate, 0.5 mM TPP, 0.5 mM MgCl$_2$, 10 µM FAD and 20 mM potassium phosphate buffer (pH 7.5). One ml of this reaction solution was used. After the eluted fraction to be measured was added, the measurement reaction was performed at 30° C. for 40 to 60 min. Then, the reaction was stopped by addition of 0.1 ml of 6N sulfuric acid (or 0.25 N sodium hydroxide).

After the reaction was stopped, the reaction solution was incubated at 60° C. for 10 min, thereby converting acetolactate contained in the reaction solution to acetoin.

Then, to quantify acetoin contained in the reaction solution, 1 ml of 0.5% (w/v) creatine and 1 ml of 5% (w/v) α-naphthol dissolved in 2.5 N sodium hydroxide was added to the reaction solution, followed by incubation at 37° C. for 10 min. Acetoin was then quantified by color comparison of the absorbance (at 525 nm) of the reaction solution, thereby evaluating ALS activity. In addition, since the reaction solution contained a small amount of sodium pyruvate, reaction time 0 was used as control.

Figure 7:
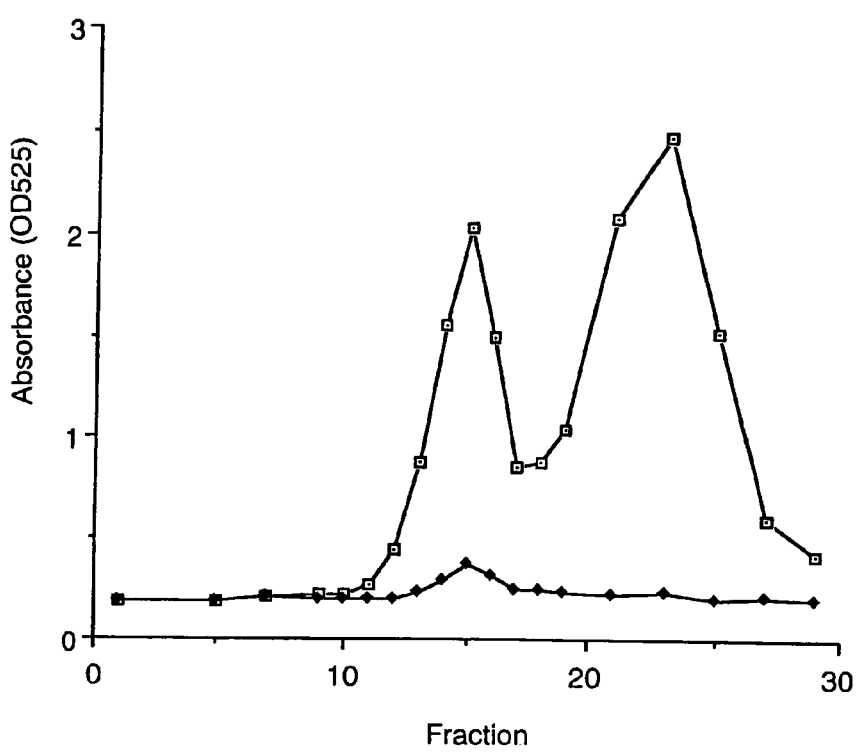
FIG. 7 is a characteristic figure showing negative ion exchange chromatogram of the crude ALS protein extracted from the wild type.

As a result, absorbance at OD525 nm was as high as approximately 7 per 0.2 ml of the reaction solution. However, when the above measurement reaction was ceased with sodium hydroxide, and acetoin generation activity due to activity other than ALS activity was examined, nearly 80% of the apparent ALS activity resulted from direct acetoin generation activity which was not due to activity of the mutant ALS protein. Accordingly, the mutant ALS protein and the other proteins were separated for acetoin generation activity by FPLC using negative ion exchange resin. As a result, two activity peaks were detected as shown in FIG. 7.

To determine which one of the two activity peaks corresponded to the mutant ALS protein, acetoin generation activity was examined for the two peaks. Thus it was found that a fraction shown by the earlier peak corresponded to the mutant ALS protein.

Using the enzyme solution containing the mutant ALS protein, sensitivity of the mutant ALS protein to bispyribac-sodium, chlorsulfuron and imazaquin was examined. Sensitivity to each of these herbicides was evaluated by measuring ALS activity in the same manner as in the above measurement reaction, except that a herbicide was added to a certain concentration before addition of the enzyme solution. For comparison, the wild type ALS protein was separated and purified in the same manner and used for the experiment. In addition, bispyribac-sodium was prepared as an aqueous solution, and chlorsulfuron and imazaquin were prepared as acetone solutions. The final concentration of acetone in the reaction mixture was 1%.

Figure 8:
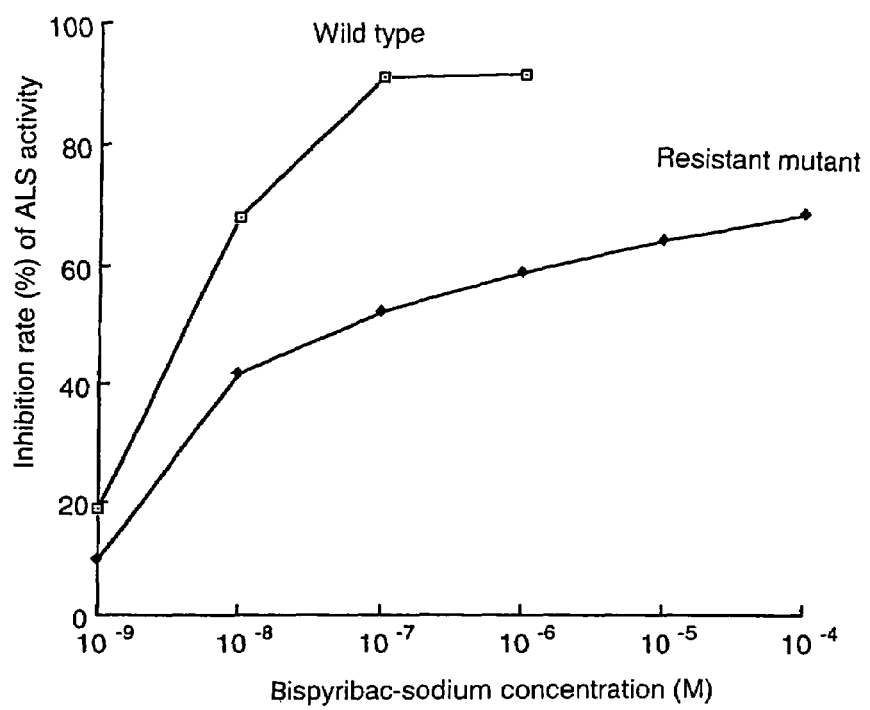
FIG. 8 is a characteristic figure showing sensitivity of the wild type ALS protein and the mutant protein to bispyribac-sodium.
Figure 9:
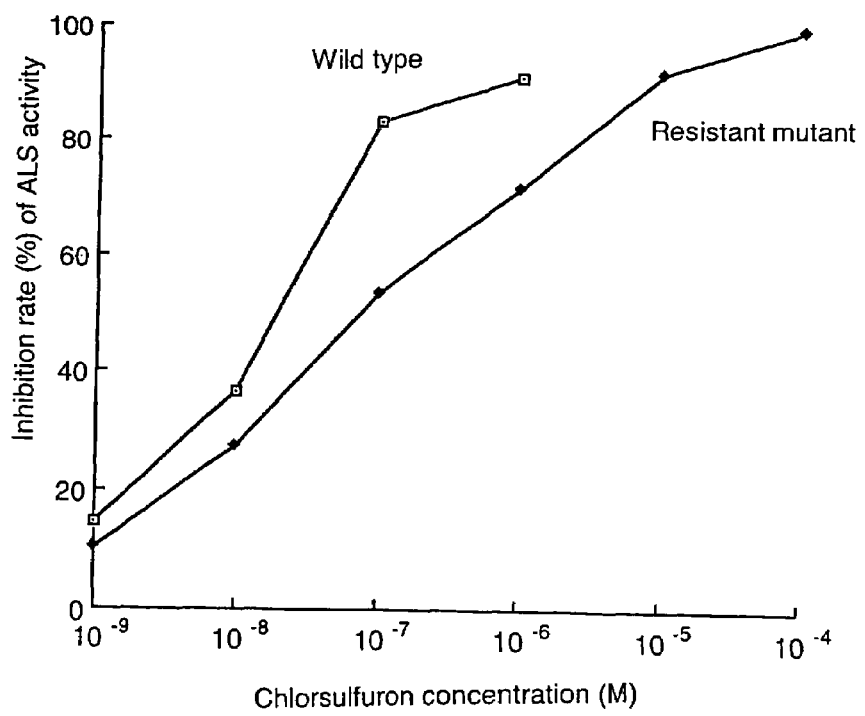
FIG. 9 is a characteristic figure showing sensitivity of the wild type ALS protein and the mutant protein to chlorsulfuron.
Figure 10:
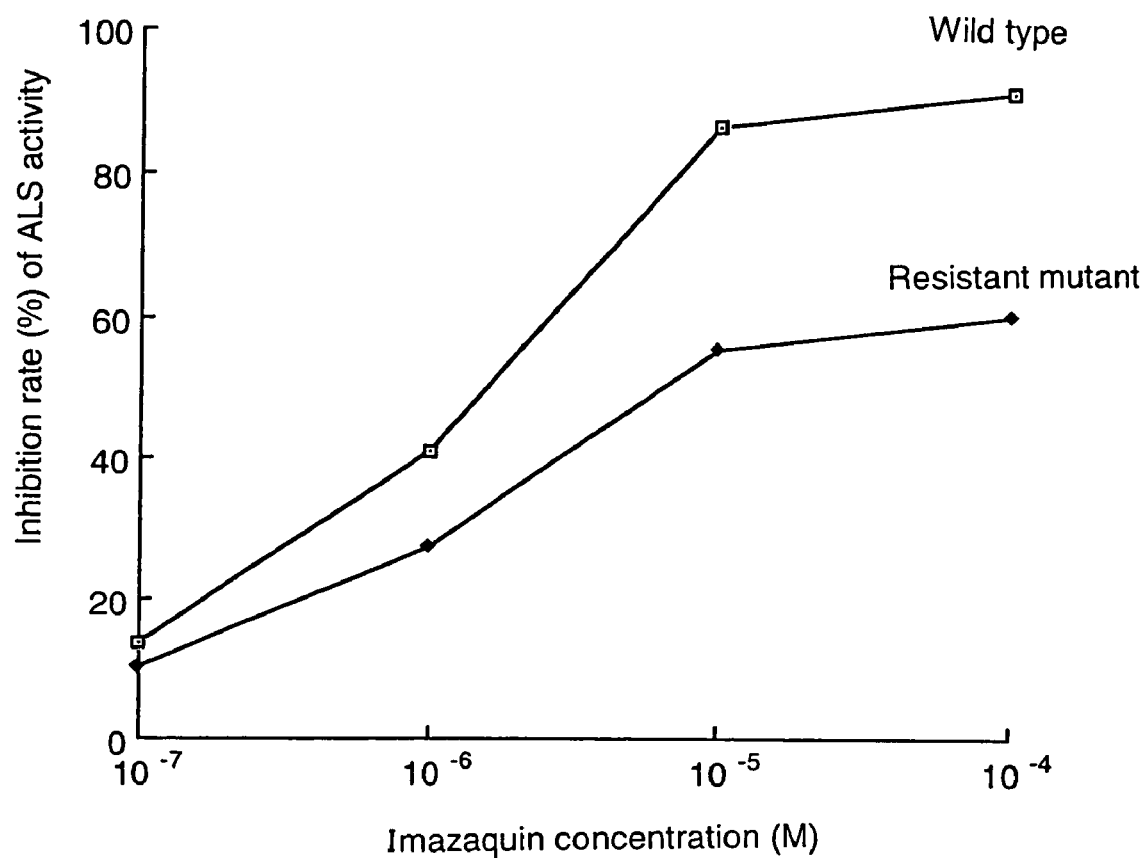
FIG. 10 is a characteristic figure showing sensitivity of the wild type ALS protein and the mutant protein to imazaquin.

FIG. 8 shows the relation of ALS activity inhibition rate and bispyribac-sodium concentration. FIG. 9 shows the relation of ALS activity inhibition rate and chlorsulfuron concentration. FIG. 10 shows the relation of ALS activity inhibition rate and imazaquin concentration. A line connecting white squares denotes the wild type ALS protein, a line connecting black squares denotes the mutant ALS protein in FIGS. 8 to 10.

A herbicide concentration which inhibits 50% of ALS activity (I50) was calculated according to probit analysis, thereby calculating the ratio of I50 for the mutant ALS protein vs. I50 for the wild type ALS protein. Table 2 shows the results.

| Chemical Compounds | I50 (nM)[a] Wild type | I50 (nM)[a] Resistant mutant | RS ratio[b] Resistant mutant |
|---|---|---|---|
| Bispyribac-sodium | 5.63 | 421 | 74.8 |
| Chlorsulfuron | 17.3 | 92.8 | 5.36 |
| Imazaquin | 1480 | 16700 | 11.3 |

[a] Concentration for 50% inhibition
[b] Calculated from the inhibition activity in Table 1: I50 (resistant mutant)/ I50 (wild type)

As shown in FIGS. 8 to 10 and Table 2, the mutant ALS protein showed a relatively high ALS activity even in the presence of the herbicide, when compared to the wild type ALS protein. In particular, the most significant difference between the mutant and the wild type ALS protein was sensitivity to bispyribac-sodium herbicide. That is, the mutant ALS protein possesses good resistance to bispyribac-sodium.

Example 3

Cloning of Mutant ALS Gene

Probes used for cloning a gene (mutant ALS gene) encoding the mutant ALS protein from the resistant mutant were prepared as follows. The partial cDNA used as a probe in this example was derived from rice (Nippon-bare) showing high homology with the ALS gene of maize.

(1) Determination of the Nucleotide Sequence of a Partial cDNA Derived From Rice (Nippon-Bare) Showing High Homology With the ALS Gene of Maize As a part of the Ine Genome Project conducted by the Society for Techno-innovation of Agriculture, Forestry and Fisheries, and National Institute of Agrobiological Sciences, partial nucleotide sequences of cDNAs of rice (Nippon-bare) had been determined and a partial nucleotide sequence database of cDNAs had already been established. A cDNA clone (Accession No. C7241 1) which is known as a nucleotide sequence of approximately 350 bp contained in this database showed high homology to the ALS gene of maize. The ALS gene of maize had been completely sequenced.

This cDNA clone (Accession No. C72411) was obtained from National Institute of Agrobiological Sciences, and the nucleotide sequence was determined as follows. Here, the cDNA clone comprised an ALS homolog gene inserted within pBluescript II SK+, and it was capable of autonomous replication in *E. coli*.

First, an ALS homolog-retaining plasmid vector was transformed into *E. coli* (DH5α). White colonies obtained from a plate were cultured in liquid, and then plasmids were extracted from the cells by standard techniques. Since the insert DNA had been inserted between SalI and NotI (restriction enzymes of multi-cloning sites in the plasmid vector), the vector was digested with the two enzymes. The insert was confirmed by agarose electrophoresis. Then, the obtained ALS homolog-retaining plasmid vector was purified by standard techniques using e.g. RNaseA, PEG and LiCl, followed by sequencing reaction using primers and an ABI BigDyeTerminator Cycle Sequencing Kit. Conditions for PCR reaction followed the manufacture's protocol. Primers used herein were M13 primers and synthesized primers designed from the determined nucleotide sequence. The resulting PCR product was purified by ethanol precipitation, and then the nucleotide sequence thereof was determined by an ABI PRISM 310 sequencer.

The ALS homolog-retaining plasmid vector is known to contain an insert DNA with a length of 1.6 kb. The obtained ALS homolog-retaining plasmid vector was digested with restriction enzymes Sa II and Not I, and then subjected to electrophoresis. Therefore, a band of about 3 kbp corresponding to pBluescript Il SK+ and a band of about 1.6 kbp corresponding to the insert DNA fragment were detected (not shown). The entire nucleotide sequence of the insert DNA portion was determined, and its homology to the nucleotide sequence of maize was searched. As shown in FIG. 11, 84.7% homology was found. Since the ALS homolog was determined to be a partial cDNA of the ALS gene of the var. Nippon-bare, the insert DNA digested with Sal I and Not I was used as a probe. Further in FIG. 11, the first row is a nucleotide sequence of the partial cDNA of the ALS gene of the var. Nippon-bare; the second row is that of the ALS gene of maize.

(2) Preparation of mRNA From Resistant Mutant

First, the resistant mutant frozen with liquid nitrogen was crushed with a mortar and pestle, and then finely crushed with a mixer for 30 sec. The crushed powder was suspended in an extraction buffer [(100 mM Tris-HCl pH 9.0, 100 mM NaCl, 1 wt % SDS, 5 mM EDTA): (β-mercaptoethanol): (Tris saturated phenol)=15:3:20], and then stirred thoroughly. This solution was centrifuged at 12,000×g for 15 min, and then the supernatant was collected. Two hundred ml of PCI [(Tris saturated phenol): (chloroform): (isoamylalcohol)=25:24:1] was added to the supernatant, shaken at 4° C. for 10 min, centrifuged at 12,000×g for 15 min, and then the supernatant was collected. The procedure was repeated twice. A 1/20 volume of 5 M NaCl and a 2.2-fold volume of ethanol were added to the obtained supernatant, and then the mixture was allowed to stand at −80° C. for 30 min. The precipitate was collected by centrifugation at 12,000×g for 5 min. The precipitate was washed with 70% ethanol, dried, and then dissolved in 10 mM β-mercaptoethanol solution. Next, the solution was centrifuged at 27,000×g for 10 min to remove insoluble fraction. A ¼ volume of 10 M LiCl was added to the solution, which was then allowed to stand on ice for 1 hour. Further, the solution was centrifuged at 27,000×g for 10 min to collect precipitate, dissolved in 4 ml of $H_2O$, and then absorbance at 260 nm was measured to find the concentration of RNA. A 1/20 volume of 5 M NaCl and a 2.2-fold volume of ethanol were added to the solution, which was then allowed to stand at −80° C. for 30 min. Subsequently the solution was centrifuged at 27,000×g for 10 min to collect the precipitate, followed by washing with 70% ethanol, and drying. The resulting product was dissolved in an appropriate amount of $H_2O$ to obtain a total RNA solution. Here, centrifugation was performed at 4° C.

mRNA was separated and purified from total RNA by the following method. A 2× binding buffer (20 mM Tris-HCl pH 7.5, 10 mM EDTA, 1 M NaCl) in a volume equivalent to that of the extracted total RNA solution was added to the extracted total RNA solution. A column filled with 0.1 g of oligo dT cellulose (Amersham Pharmacia Biotec) was washed with a 1× binding buffer, and then the total RNA solution was applied to the column. After the column was washed with a 1× binding buffer, an elution buffer (10 mM Tris-HCl pH 7.5, 5 mM EDTA) was applied, and the eluate collected 0.5 ml at a time. Fractions that had passed through the column were applied to another oligo dT cellulose (Amersham Pharmacia Biotec) column, and treated in the same manner. After the concentration of eluted mRNA was calculated based on the absorbance of each fraction, a 1/10 volume of 10 M LiCl and a 2.5-fold volume of ethanol were added to the products, and then the mixtures were allowed to stand at −80° C. for 30 min. Next, the mixtures were centrifuged and the precipitated fractions were dried, and dissolved in 100 μl of $H_2O$. The thus obtained mRNA was subjected to size fractionation by sucrose density gradient centrifugation.

The separated and purified mRNA was applied to a centrifuge tube with density gradient given by a 25% sucrose solution and 5% sucrose solution, and then ultra-centrifuged at 27,000 rpm for 15 hours at 4° C. using a swing rotor. After centrifugation, 0.5 ml of each fraction was collected in order of density gradient. Absorbance of each fraction was measured, the concentration of the collected mRNA was calculated, and the presence of ALS mRNA was confirmed by hybridization using an ECL kit (ECL direct nucleic acid labeling and detection system, Amersham Pharmacia Biotec). Hybridization was performed using a probe prepared in (1) above at 42° C. for 16 hours. After hybridization, washing at 42° C. for 5 min was performed twice using a primary washing buffer provided with the kit, and then washing at 42° C. for 5 min was performed once using 2×SSC solution. The washed film was wrapped with a transparent plastic film to keep it immersed in an attached luminous reagent provided with the kit, and then exposed to an X-ray film.

Approximately 35 mg of total RNA was extracted from the resistant mutant and approximately 4 mg of mRNA could be extracted by the above procedures. Further, in sucrose density gradient centrifugation, a hybridization-positive spot was found for a fraction expected to be positive.

When the wild type was used, approximately 95 mg of total RNA was extracted in addition to approximately 7 mg of mRNA. When mRNA was extracted from the wild type, the above method was applied except that the wild type was used instead of the resistant mutant.

(3) Construction of cDNA Library Derived From Resistant Mutant

Using 2 μg of mRNA purified in (2) above and a cDNA synthesis kit (Amersham Pharmacia Biotec), cDNA was synthesized, so that a cDNA library derived from the resistant mutant was constructed.

First, RTase provided with the kit was used for a reverse transcription reaction; T4 DNA polymerase provided with the kit was used for a subsequent complementary chain elongation reaction. Upon complementary chain elongation reaction, $^{32}$P-dCTP was added to calculate the yield of cDNA synthesis. After an adaptor was added, the synthesized cDNA was incorporated into λ phage by in vitro packaging method.

The adaptor added to cDNA was an Eco RI-Not I-Bam HI adaptor (Takara Shuzo). Adapters with a molar concentration 50-fold greater than that of cDNA were added to a solution containing cDNA. Then, T4 DNA Ligase (Pharmacia) was added to the mixture followed by ligation reaction at 4° C. overnight. The reaction solution was applied to HPLC using an AsahiPak GS 710 column (Asahi Chemical Industry Co., Ltd.), followed by monitoring the eluate with ultraviolet rays at a wavelength of 260 nm. The eluate was fractionated into 25 fractions of 0.5 ml each. Each fraction was measured with a Cerenkov counter, and 3 to 4 fractions with a high count were collected. The 5' terminus of the adaptor contained in the fraction was phosphorylated using T4 polynucleotide kinase (Takara Shuzo), and then λgt 11 Eco RI arm was added to perform ligation. GigaPack Gold III (Stratagene) was added to the solution, and then ligation reaction was performed at room temperature for 2 hours. After reaction, 200 μl of a SM buffer and 8 μl of chloroform were added to the reaction solution, thereby preparing a phage solution. This phage solution was diluted 10-fold. One μl of the diluted solution was infected with E. coli (Y-1088), to which 0.7% top agar was added, and then the solution was inoculated over a LB plate. The number of plaques that had emerged on the plate 4 to 8 hours later was counted, thereby measuring the titer.

Synthesis of approximately 74 ng of cDNA derived from the resistant mutant was confirmed by the result of DE 81 paper and Cerenkov counting. The result of Cerenkov counting after ligation of a vector with an adaptor added thereto revealed that approximately 22 ng of λDNA containing the insert inserted therein was obtained for the resistant mutant. The λDNA was packaged into the phage, thereby preparing a cDNA library derived from the cells of the resistant mutant. The titer of the library solution was 16,600 pfu/μl.

When a cDNA library was prepared using mRNA extracted from the wild type according to the above-mentioned method, approximately 38 ng of cDNA derived from the wild type was synthesized. Further, approximately 5 ng of λDNA containing the insert inserted therein was obtained for the wild type. Furthermore, the titer of the cDNA library solution derived from the wild type was 18,160 pfu/μl.

(4) Screening of cDNA Containing the ALS Gene

To form about 20,000 plaques on the plates, the library solution prepared in (3) above was diluted, and then thereon phages derived from the wild type and those derived from the resistant mutant were separately inoculated over 10 plates, respectively. Plaques were transferred to a nitrocellulose membrane (Schleicher & Schnell, PROTORAN BA85, pore size 0.45 mm). The nitrocellulose membrane was immersed in a denaturation solution (0.5 M NaOH, 1.5 M NaCl), and then in a neutralization solution (1.5 M NaCl, 0.5 M Tris-HCl pH 7.5, 1 mM EDTA) for approximately 20 sec. Excess water was removed using a filter paper from the nitrocellulose membrane, and then the nitrocellulose membrane was baked at 80° C. for 2 hours. In addition, the baking step was omitted when Hybond-N+ (Amersham Pharmacia Biotec) was used instead of a nitrocellulose membrane, and immobilization was performed with 0.4 M NaOH for 20 min.

The insert DNA prepared in (1) above was labeled by two types of method, RI and non-RI, and then used as a probe DNA. Labeling with RI and hybridization were performed by the following method. First, approximately 200 to 500 ng of probe DNA was thermally denatured, and then labeled using a BcaBEST DNA labeling kit (Takara Shuzo Co., Ltd). Upon this labeling reaction, a buffer, random primers and $^{32}$P-dCTP provided with the kit were added. Next, BcaBEST was added, followed by incubation at 65° C. for 30 min. Subsequently, EDTA was added to stop the reaction. The reaction solution was applied to nitrocellulose membranes, so that 8 sheets of the membrane contained approximately 100 ng of probes. Hybridization was performed at 42° C. overnight with weakly shaking. After hybridization, the membranes were washed three times with 2×SSC, 0.1% SDS solution, followed by exposure for about 1 hour to an imaging plate of a BAS 2000 imaging analyzer (Fuji Photo Film Co., Ltd.). Following exposure, positive clones were detected using the imaging analyzer.

Labeling with non-RI was performed by the following method. Following thermal denaturation of approximately 200 to 500 ng of probe DNA, DNA labeling reagent (peroxidase) and glutaraldehyde which are provided in an ECL direct DNA/RNA labeling and detection system (Amersham Pharmacia Biotech) were added, followed by incubation at 37° C. In this case, the labeled probe DNA was applied to nitrocellulose membrane, so that 8 sheets of the membrane contained approximately 100 ng of the labeled probe DNA. Hybridization was performed at 42° C. overnight with weakly shaking. After hybridization, the membrane was washed three times with a primary washing buffer at room temperature for 10 min, and then once with 2×SSC at room temperature for 10 min. The membrane was immersed in a luminous solution provided with the ECL kit, and then exposed to an X-ray film for 30 min to 3 hours.

Positive phages obtained by hybridization (primary screening) were scraped off together with top agar using a sterile toothpick, and then suspended in 200 μl of SM buffer, thereby obtaining a phage solution. Phage solutions of each clone were appropriately diluted, infected with E. coli strain Y-1088, and then inoculated over LB plates. Using these newly prepared plates, hybridization (secondary screening) was performed similarly. Positive phages were suspended in 200 μl of a SM buffer, thereby obtaining single phages. If no single phage was isolated by secondary screening, another dilution was performed, followed by inoculation over LB plates. Subsequently, hybridization (the third screening) was performed, so that single phages were obtained.

Next, λDNA was prepared from the single phages by the following methods. λ phages collected with a bamboo brochette or a toothpick from plaques of positive clones were inoculated in 200 μl of a 2×YT medium (containing 10 mM MgCl$_2$ and 0.2% maltose) containing 5 μl of a suspension of fresh host E. coli (Y1088). The product was allowed to stand and incubated at 42° C. overnight. Then, the medium was inoculated again in 1 ml of a 2×YT medium (containing 10 mM MgCl$_2$ and 0.2% maltose) containing 25 μl of a suspension of host E. coli (Y1088), and then shake-cultured overnight (these steps compose a pre-culturing process). The pre-cultured solution (10 to 50 μl) was inoculated in a 12 ml of 2×YT medium containing 10 mM MgCl$_2$ and 0.5 ml of E. coli Y1088 suspension. Then, incubation was performed at 42° C. overnight with relatively strong shaking, until turbidity increased after lysis. After culturing, 50 μl of chloroform and 1.2 ml of 5 M NaCl were added, and then incubation was performed at 42° C. for 10 min while shaking. The product was centrifuged at 27,000×g for 10 min, and then the supernatant was newly transferred to a centrifugation tube. Five ml of 50% PEG was added to the supernatant, and then incubated on ice for 1 hour or more. The product was centrifuged at 27,000×g for 10 min, and then the supernatant was discarded. Next, another centrifugation was performed at 27,000×g, and then the liquid portion was discarded. The precipitated fraction was suspended in 300 μl of a 30 mM Tris hydrochloric acid buffer (pH 7.5) containing 4 μg of DNase I, 20 μg of RNase A and 10 mM MgCl$_2$. The suspension was transferred to a 1.5 ml tube. After incubation of the suspension at 37° C. for 30 min, 7.5 μl of 20% SDS, 3 μl of proteinase K (10 mg/ml), and 12 μl of 0.5 M EDTA were added to the suspension, followed by further incubation at 55° C. for 15 min. Subsequently, 150 μl of phenol was added to the product, and then stirred vigorously. Then the mixture was centrifuged at 15,000 rpm for 3 min using a TOMY Microcentrifuge MR-150 (TOMY DIGITAL BIOLOGY CO., LTD.), and an aqueous layer collected. 800 μl of ethyl ether (to which distilled water had been added to remove peroxide) was added to the collected aqueous layer. The mixture was stirred vigorously, and then centrifuged at 15,000 rpm for 10 sec and the ether layer was discarded. After the ether extraction step was repeated, ether remaining in the aqueous layer was removed with nitrogen gas. Thirty μl of 5 M NaCl and 875 μl of ethanol were added to the aqueous layer, so that precipitated λDNA was rapidly collected. The collected λDNA was rinsed with approximately 1 ml of 70% ethanol, and then dried under reduced pressure for approximately 1 min, thereby removing ethanol. The product was dissolved in 20 μl to 50 μl of a TE buffer (pH 8.0), thereby preparing a λDNA solution.

Subcloning and sequencing of the insert DNA in the obtained λDNA were performed by the following method. The obtained λDNA solution (1 μl) was digested with Not I so as to excise the insert DNA. The composition of a reaction solution (for cleavage reaction) followed the Manual attached to the restriction enzyme. After reaction at 37° C. for approximately 2 hours, the insert size was confirmed by electrophoresis using 1% agarose gel. λDNA (10 μl to 20 μl) containing the insert DNA was digested with Not I, so as to excise the insert DNA. The insert DNA was separated using agarose gel for sampling, the corresponding band was cleaved from the gel, and then the insert DNA was purified by standard techniques. The insert DNA was mixed with a vector following BAP treatment (dephosphorylation using alkaline phosphatase derived from a shrimp) at molar ratio of 1:1, followed by ligation reaction with T4 DNA ligase at 16° C. for 2 hours or more. Here, since the insert DNA cleaved with Not I was used as material, BAP treatment was performed for vectors cleaved with Not I. Following ligation, part of the solution was mixed with competent cells (DH5α), and then allowed to stand on ice for 30 min. Next, the mixture was subjected to heat shock at 42° C. for 30 sec, and then allowed to stand on ice again for 2 min. Then, SOC was added to the mixture, incubated at 37° C. for 1 hour, inoculated over a LB medium plate on which a mixture of 100 μl of 2×YT (containing 50 μg/ml ampicillin), 30 μl of 3% X-Gal and 3 μl of 1 M IPTG had been previously added uniformly, and then cultured at 37° C. for 10 hours or more. The transformed white colonies were each inoculated on 2 ml of an LB medium containing ampicillin or a 2×YT medium, and then cultured at 37° C. overnight. From the culture solution, plasmids were prepared by standard techniques and dissolved in H$_2$O. The DNA concentration thereof was quantified, and then the plasmids were subjected to PCR reaction for sequencing. PCR reaction and sequencing were performed by methods described above.

Therefore, the ALS cDNA with an incomplete length of approximately 2.2 kb was obtained by the above experiment. Since an Sma I site was present at a position approximately 250 bp from the 5' side of the DNA, a new probe was prepared by the following method. pBluescript II SK+ containing the approximately 2.2 kbp was amplified with host E. coli JM109, and then plasmids were extracted using an automated isolation system (KURABO PI-100). The plasmid was directly digested with Sma I. The generated fragment of approximately 250 bp was separated and purified by 1% agarose electrophoresis, and then the concentration was calculated, thereby preparing a probe. Using the probe, the library was screened again by the above method employing RI. λDNA was prepared from the thus obtained single phages, the λDNA solution (1 μl) was digested with Eco RI, and then size was confirmed by electrophoresis, followed by immobilization onto a nitrocellulose membrane. Following electrophoresis, the gel was immersed in 0.5 M NaOH solution containing 1.5 M NaCl, and then shaken lightly for 15 min. The gel was then washed with water, immersed in 0.5 M Tris-HCl (pH 7.5) containing 3 M NaCl, and then neutralized while shaking for approximately 15 min. Approximately 5 thick, industrial filter papers were piled up to make a base. The base was placed in 20×SSC spread over a stainless bat. Subsequently, the neutralized gel, a membrane (which had been cut into a certain size, immersed in distilled water and then immersed in 20×SSC for another 10 min), and two-ply filter papers were placed in order on the seat, on which a paper towel with a thickness of 3 cm to 4 cm was further placed. A glass plate and then a light weight were placed on the product, followed by blotting for approximately 5 min. After confirmation of there being no bubble entrapped between the gel and the membrane, blotting was performed for approximately 10 min. Following blotting, the membrane was subjected to UV treatment with a trans-illuminator, and then baked at 80° C. for approximately 15 min to 30 min. After baking, hybridization (hybridization buffer composition: 5×SSPE, 0.5% SDS, 5× Denharlts, solum sperm DNA, 50% formamide) was performed with the above 250 bp probe DNA labeled with $^{32}$P. Radiation of the hybridized band was transferred to an imaging plate, and the result was analyzed with BAS-2000. Among inserts positive in hybridization, those showing a relatively large size were prepared in large quantity, and then sub-cloned (FERM BP-7348) into pBluescript II SK+ that had been digested with Eco RI and then treated with BAP by the above method. The product was transformed into *E. coli* (JM 105). The obtained transformants were subjected to liquid culture, and then plasmids were prepared by standard techniques. Thus, the nucleotide sequence was determined by the above methods.

As a result, the cDNA containing a full length mutant ALS gene could be obtained. The nucleotide sequence of the cDNA is shown in SEQ ID NO: 2. Further, one type of cDNA containing a full length ALS gene could be obtained from a cDNA library derived from the wild type. FIG. 1 shows the result of a homology comparison between the mutant ALS gene and the wild type ALS gene.

Example 4

Expression of Mutant ALS Protein

The plasmid obtained in Example 3 (4) was digested with Eco RI, the cDNA containing the wild type ALS gene and the cDNA containing the mutant ALS gene were cut out, and then they were separately incorporated into pGEX expression vector. The cDNA containing the wild type ALS gene had a 5' non-translation region which was 47 nucleotides longer than the initiation codon, and was incorporated into Eco RI site of pGEX-2T. Further, the cDNA containing the mutant ALS gene contained a 5' non-translation region which was 31 nucleotides longer than the initiation codon, and it was incorporated into Eco RI site of pGEX-4T-3.

These vectors were separately transformed into *E. coli* (JM 105). The colonies obtained by transformation were subjected to liquid culture, then plasmids were extracted, and then insertion orientation of the insert DNA was confirmed by the restriction enzyme cleavage pattern and sequencing. Clones where the orientation of the insert DNA was as expected, were each selected, and then shake-cultured in 2 ml of a LB medium containing ampicillin at 27°C. Using 1 ml of this pre-culture solution, culturing was performed in 50 ml or 250 ml of a LB medium containing ampicillin. After culturing overnight, 1 mM IPTG was added, and then expression of GST fusion protein was induced for 3 to 4 hours.

Table 3 shows the results of measuring ALS activity after addition of IPTG followed by culturing for 3 to 4 hours.

TABLE 3

| Sample | ALS activity (OD525/40 min/0.05 ml) | Protein mass (mg/ml) | Specific activity (OD525/40 min/mg protein) |
|---|---|---|---|
| Control group (no plasmid) | 1.41 | 17.6 | 1.60 |
| Wild type | 4.10 | 18.2 | 4.5 |
| Resistant mutant | 3.62 | 12.8 | 5.66 |

As shown in Table 3, *E. coli* having the wild type ALS gene and *E. coli* having the mutant ALS gene showed specific activity approximately 3 to 4-fold higher than that of the control group containing no plasmid. The transformant *E. coli* was cultured for 3 to 4 hours after addition of IPTG, and then stored at −80° C. Using the transformant *E. coli*, GST fusion ALS protein was purified.

Preparation and purification of ALS from *E. coli* were performed by the following method. First, a pellet of the transformant *E. coli* stored at −80° C. was suspended in ALS extraction buffer (potassium phosphate buffer (pH 7.5) containing 30% glycerol and 0.5 mM MgCl$_2$). Specifically, 2.5 ml of the buffer was added to the pellet obtained from 50 ml of the culture solution. The suspension was subjected to ultrasonication (Heat Systems-Ultrasonics, Sonicator W-225R, micro chip, output control 8, interval of approximately 1 sec, twice (40 sec each)), and subjected to centrifugation at 15000×g, 4° C. for 20 min, thereby obtaining the supernatant as a crude enzyme solution.

GST fusion ALS protein (hereinafter referred to as GST-ALS) was purified from the crude enzyme solution by the following method. The crude enzyme solution (12.5 ml) that had been prepared from the pellet (obtained from 250 ml of the culture solution) was applied to a glutathione sepharose 4B affinity column (Amersham Pharmacia Biotec, the bed volume, about 1 ml, that had been previously equilibrated with 10 ml of 1×PBS (0.14 M NaCl, 2.7 mM KCl, 10.1 mM Na$_2$HPO$_4$, 1.8 mM KH$_2$PO$_4$, pH 7.3)). The column was then washed with 10 ml of 1×PBS, and then the adsorbed GST-ALS was eluted (4 times) with 2 ml of 10 mM glutathione solution. GST activity and ALS activity of each of the fractions were measured, and then fractions with high activity were collected. In addition, since the adsorption rate to the above column was poor when the ALS extraction buffer was used, an experiment, which extracts enzyme with 1×PBS and allows it to be adsorbed to the above column, was also conducted. Measurement of ALS activity and quantification of protein were performed according to the above method. Measurement of GST activity was performed by a method using 1-chloro-2,4-dinitrobenzene (secondary name: abbreviated as 2,4-dichloronitrobenzen(CDNB)) as a substrate. Three ml of reaction solution, and a reaction composition (1 mM CDNB, 1 mM glutathione (reduced), enzyme solution, 100 mM potassium phosphate buffer (pH 6.5)) were used. After addition of enzyme solution, a rate assay was performed at 30° C. for increased absorbance at 340 nm. CDNB was prepared as an ethanol solution having 100-fold concentration, and then added to the reaction solution.

Activities (ALS activity and GST activity) that were not adsorbed to the above affinity column were greatly detected. However, most of the activity adsorbed to the affinity column was detected in fractions eluted with the first and the second glutathione elution. Those fractions from the first and the second elution were combined to prepare purified GST-ALS.

GST-ALS digested overnight at 4° C. with thrombin protease (25 unit) was determined as ALS freed from GST. Table 4 shows ALS activity, protein amount and specific activity after chromatography using crude enzyme solution and the above affinity column, and after thrombin protease treatment.

TABLE 4

| Sample | ALS activity (OD525/40 min/ 0.05 ml) | Protein (mg/ml) | Specific activity (OD525/40 min/mg protein) |
|---|---|---|---|
| Wild type crude enzyme | 4.6105 | 9.6 | 9.61 |
| After chromatography | 0.6083 | 0.189 | 64.4 |
| After thrombin treatment | 0.1089 | 0.189 | 11.5 |
| Resistant mutant crude enzyme | 3.1493 | 12 | 5.25 |
| After chromatography | 0.6025 | 0.045 | 268 |
| After thrombin treatment | 0.1203 | 0.045 | 53.5 |

The prepared ALS enzyme contains ALS activity derived from *E. coli*. However as shown in Table 5, since ALS activity derived from *E. coli* results from ALS isozyme I, it can be almost completely inhibited by addition of 1 mM valine.

TABLE 5

| Sample* | ALS activity (OD525/ 40 min/0.05 ml) | Inhibition rate (%) |
| --- | --- | --- |
| CK1 (without plasmid) | 1.2725 | |
| CK1 + 1 mM Valine | 0.1768 | 86 |
| CK2 (without plasmid) | 1.5508 | |
| CK2 + 1 mM Valine | 0.1831 | 88 |

*The experiment was performed twice.

Example 5

Herbicide Sensitivity of Mutant ALS Protein

Herbicide sensitivity of mutant ALS protein was examined using the crude enzyme solution obtained in Example 4. Herbicide sensitivity test was performed in the manner same as that in Example 2. In the herbicide sensitivity test, three herbicides, bispyribac-sodium, pyrithiobac-sodium, and pyriminobac were used as PC herbicides; four drugs, chlorsulfuron, bensulfuron-methyl, pyrazosulfuron-ethyl and imazosulfuron were used as sulfonylurea herbicides; and two drugs, imazaquin, and imazapyr were used as imidazolinon herbicides.

Solutions containing these herbicides at certain concentrations (bispyribac-sodium and pyrithiobac-sodium were aqueous solutions, others were acetone solutions) were added to reaction solutions before addition of the mutant ALS protein. The final concentration of acetone was 1%. In addition, since an ALS protein from the rice cDNA expressed within *E. coli* is insusceptible to valine (Kil et al., J. Biochem. Mol. Biol. 31 287–295, 1998), a herbicide sensitivity test was performed under conditions in which ALS activity derived from *E. coli* was inhibited with valine.

Figure 12:
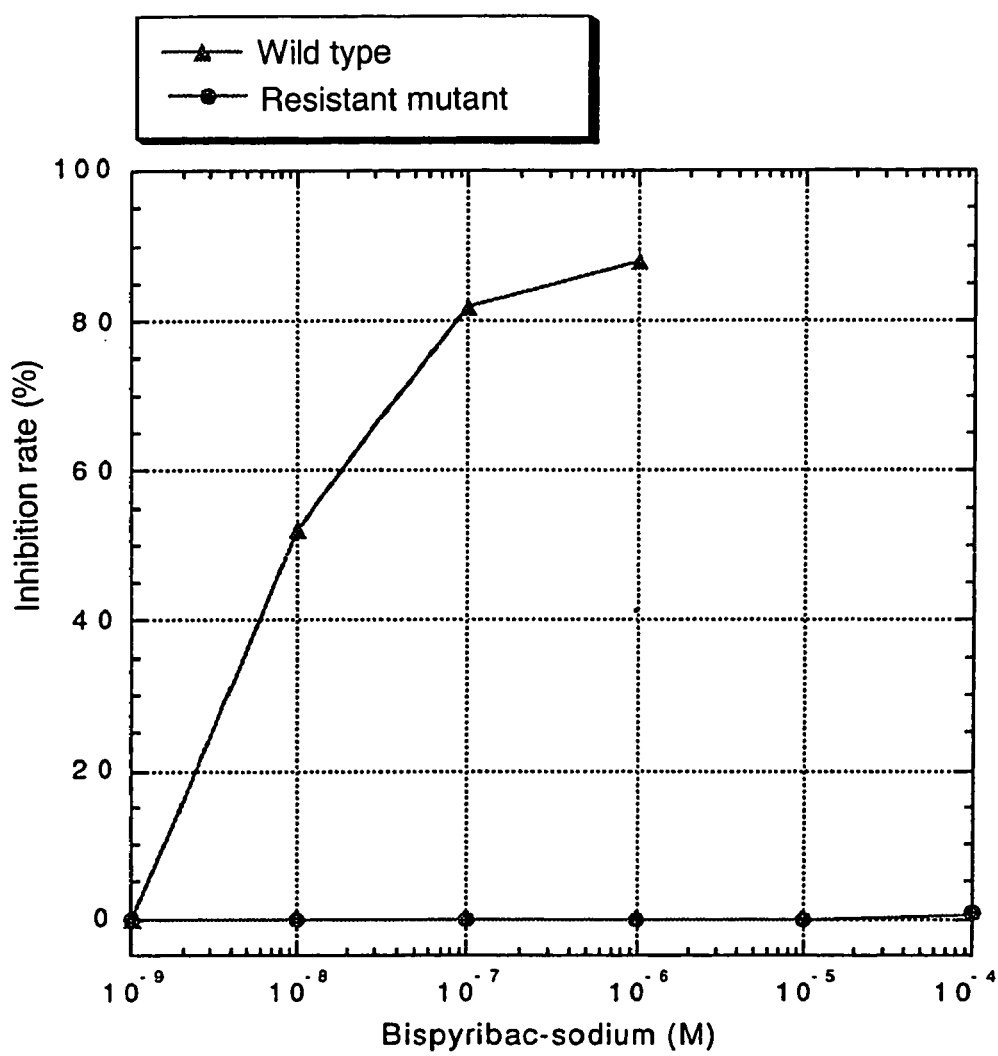
FIG. 12 is a characteristic figure showing sensitivity observed for the crude ALS obtained in Example 4 to bispyribac-sodium.
Figure 13:
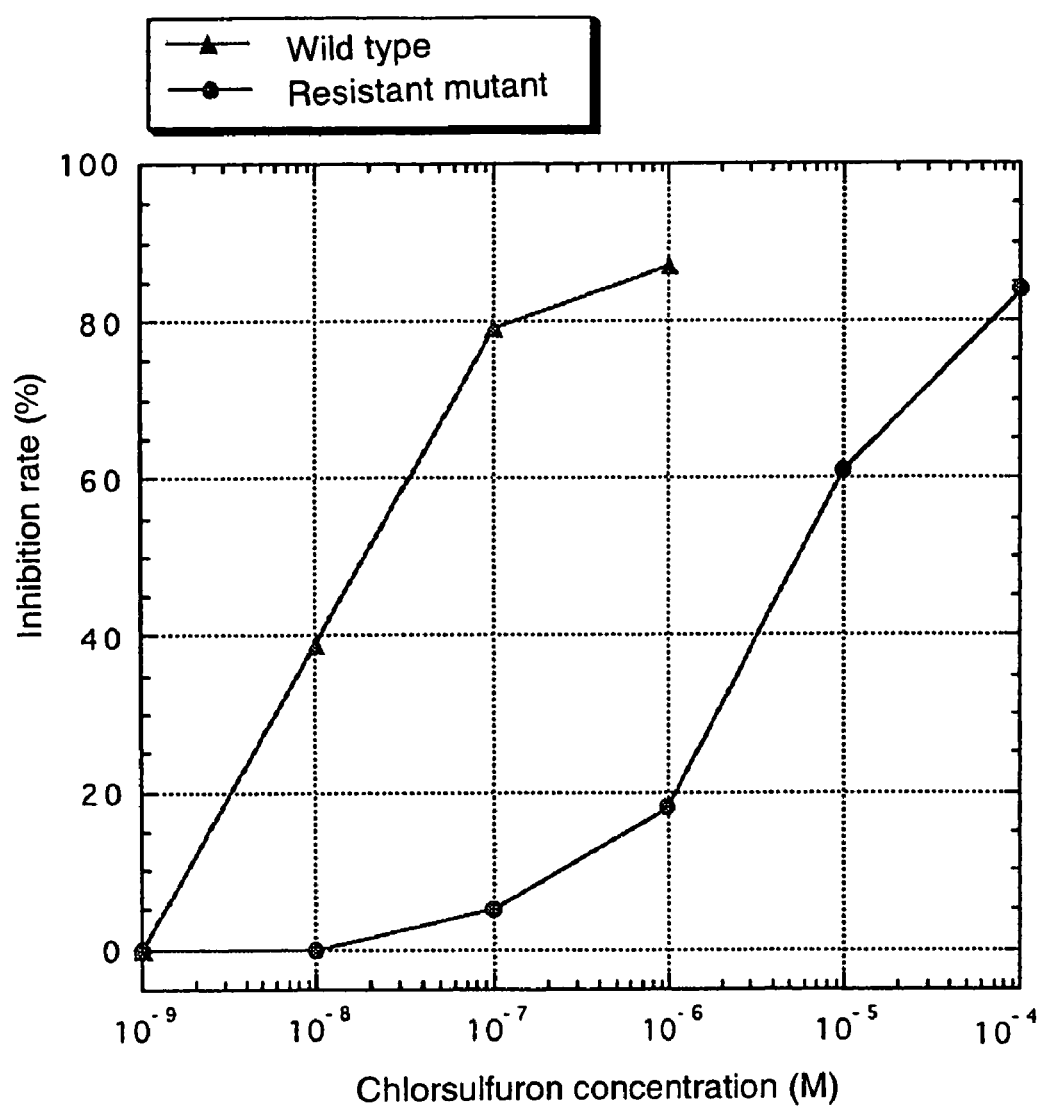
FIG. 13 is a characteristic figure showing sensitivity observed for the crude ALS obtained in Example 4 to chlorsulfuron.

FIG. 12 shows the resulting sensitivity when bispyribac-sodium was used. FIG. 13 shows the resulting sensitivity when chlorsulfuron was used. As shown in FIG. 12, wild type ALS activity was inhibited by bispyribac-sodium, while mutant ALS activity was not inhibited at all. For chlorsulfuron as shown in FIG. 13, the mutant ALS protein maintained its activity at a higher level to a certain concentration compared to the that of the wild type ALS protein, however when compared to the case of bispyribac-sodium, the resistance of the mutant ALS protein was moderate.

Figure 14:
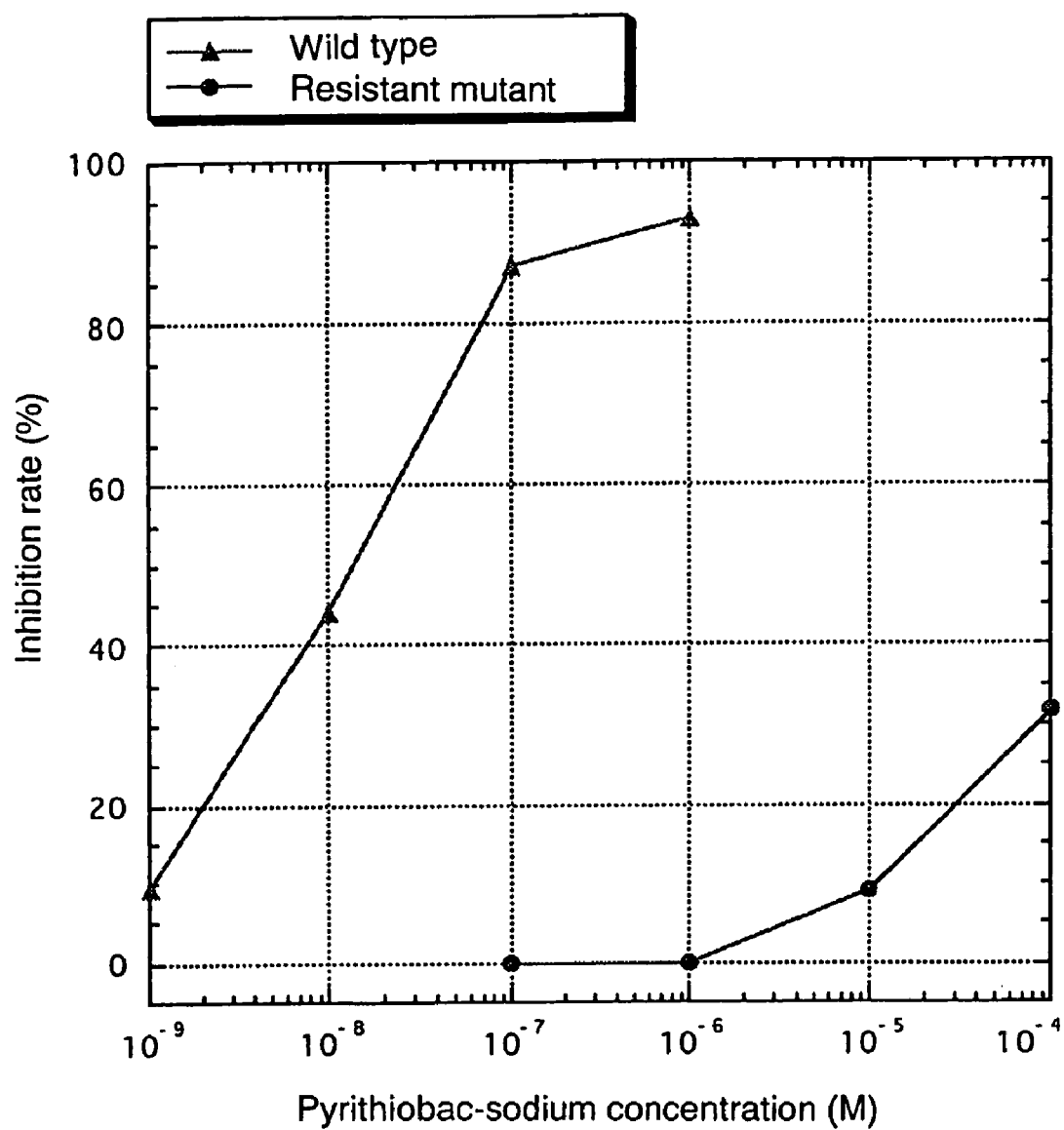
FIG. 14 is a characteristic figure showing sensitivity observed for the crude ALS obtained in Example 4 to pyrithiobac-sodium.
Figure 15:
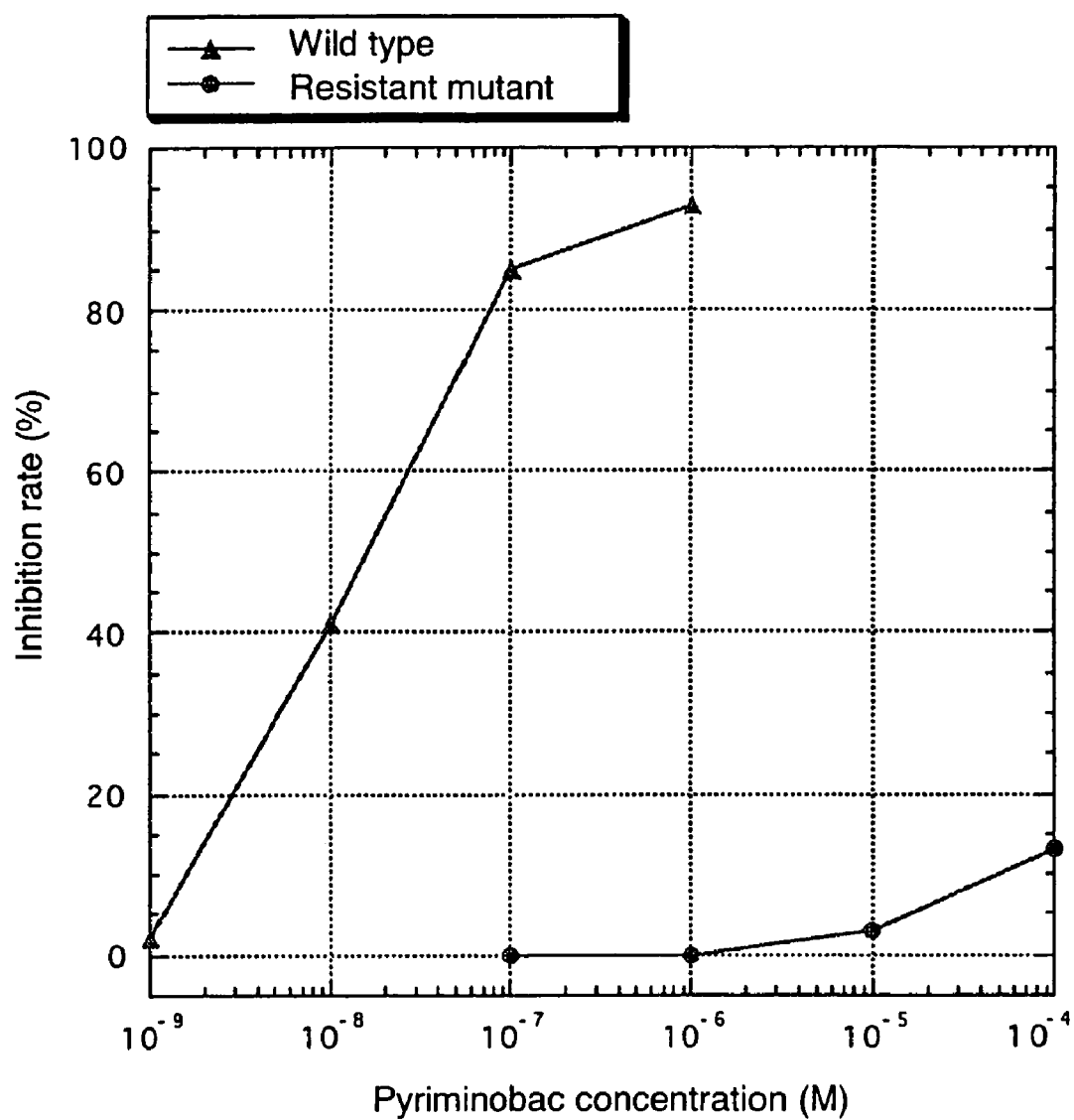
FIG. 15 is a characteristic figure showing sensitivity observed for the crude ALS obtained in Example 4 to pyriminobac.
Figure 16:
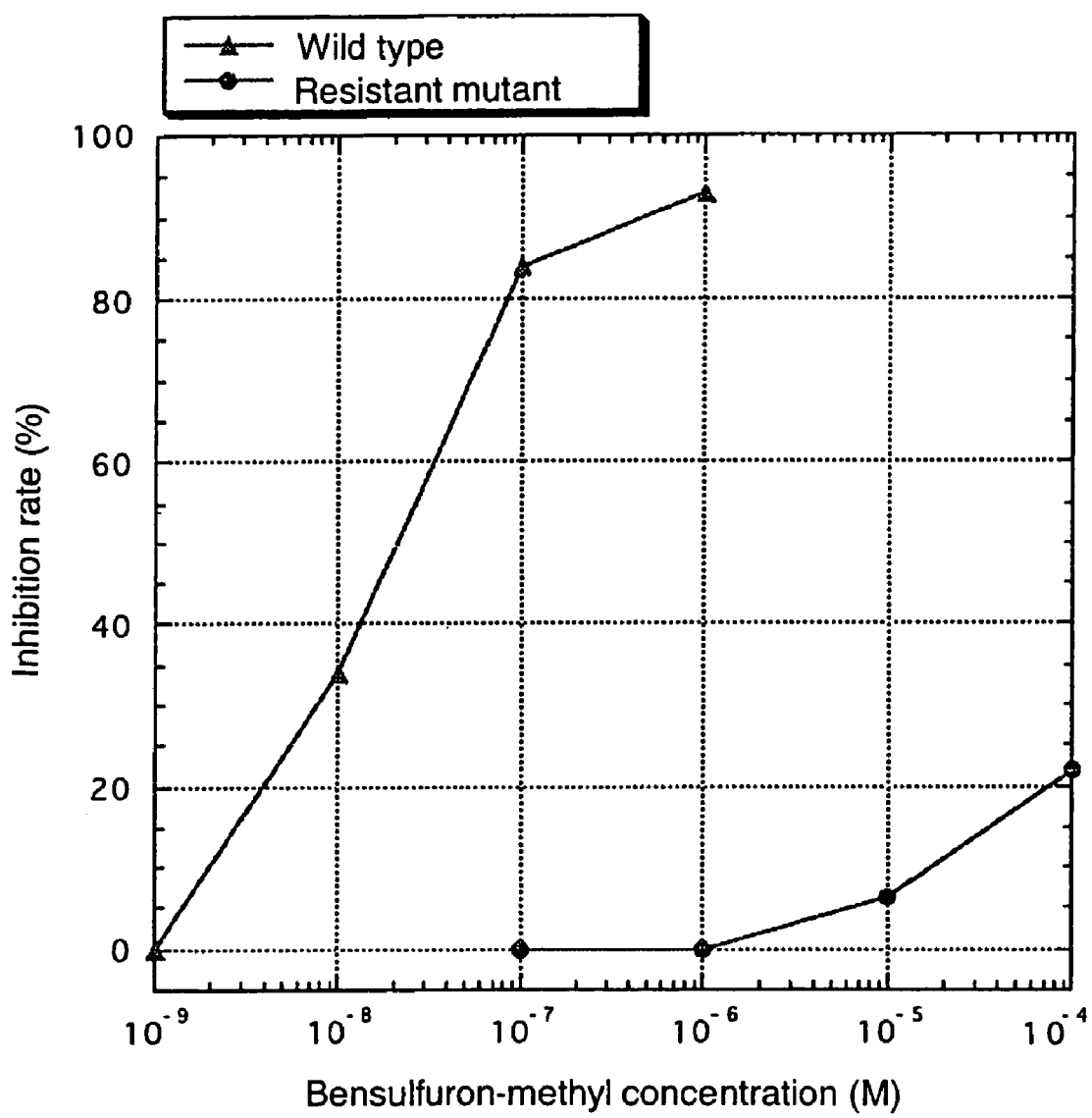
FIG. 16 is a characteristic figure showing sensitivity observed for the crude ALS obtained in Example 4 to bensulfuron-methyl.
Figure 17:
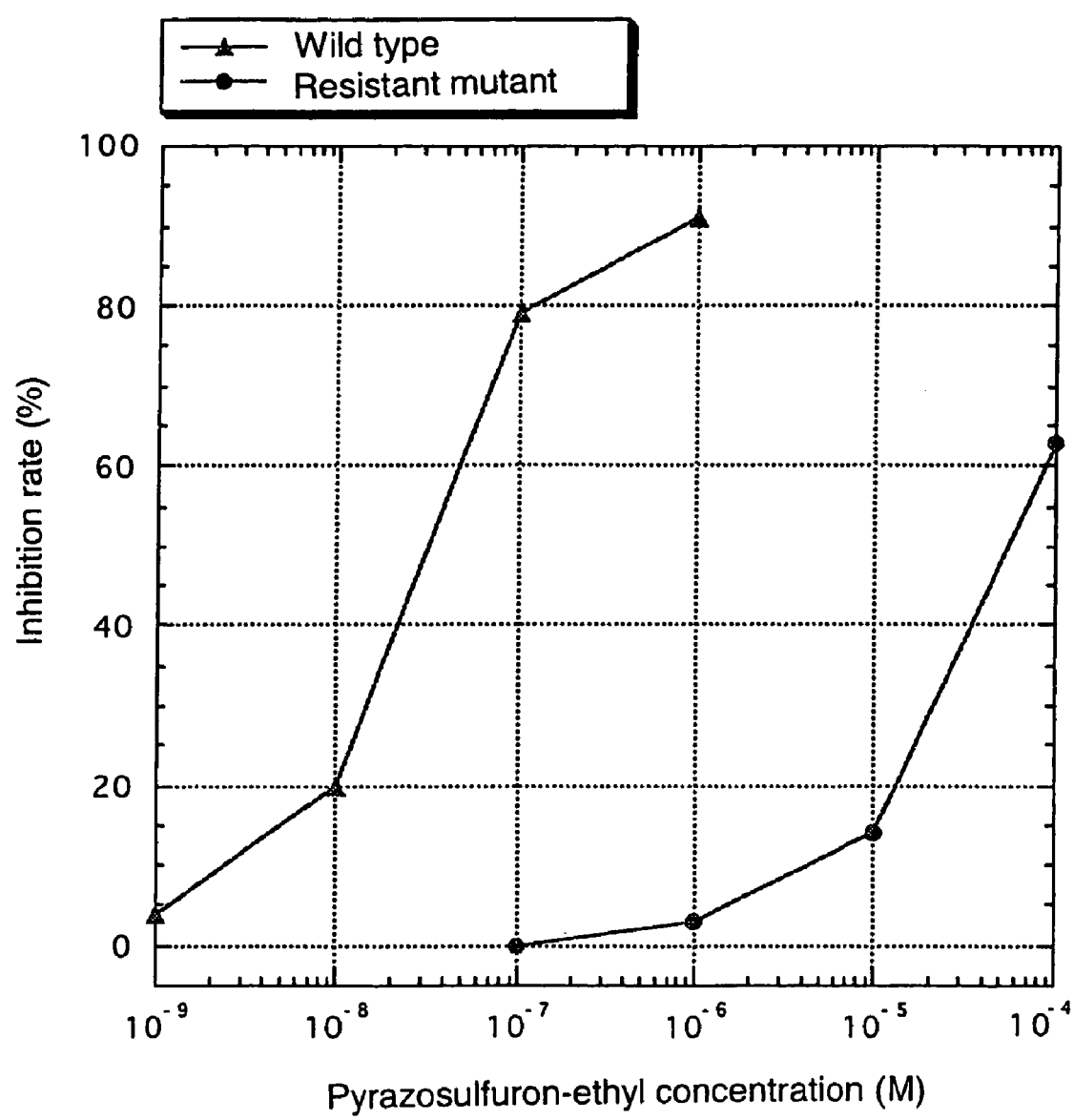
FIG. 17 is a characteristic figure showing sensitivity observed for the crude ALS obtained in Example 4 to pyrazosulfuron-ethyl.
Figure 18:
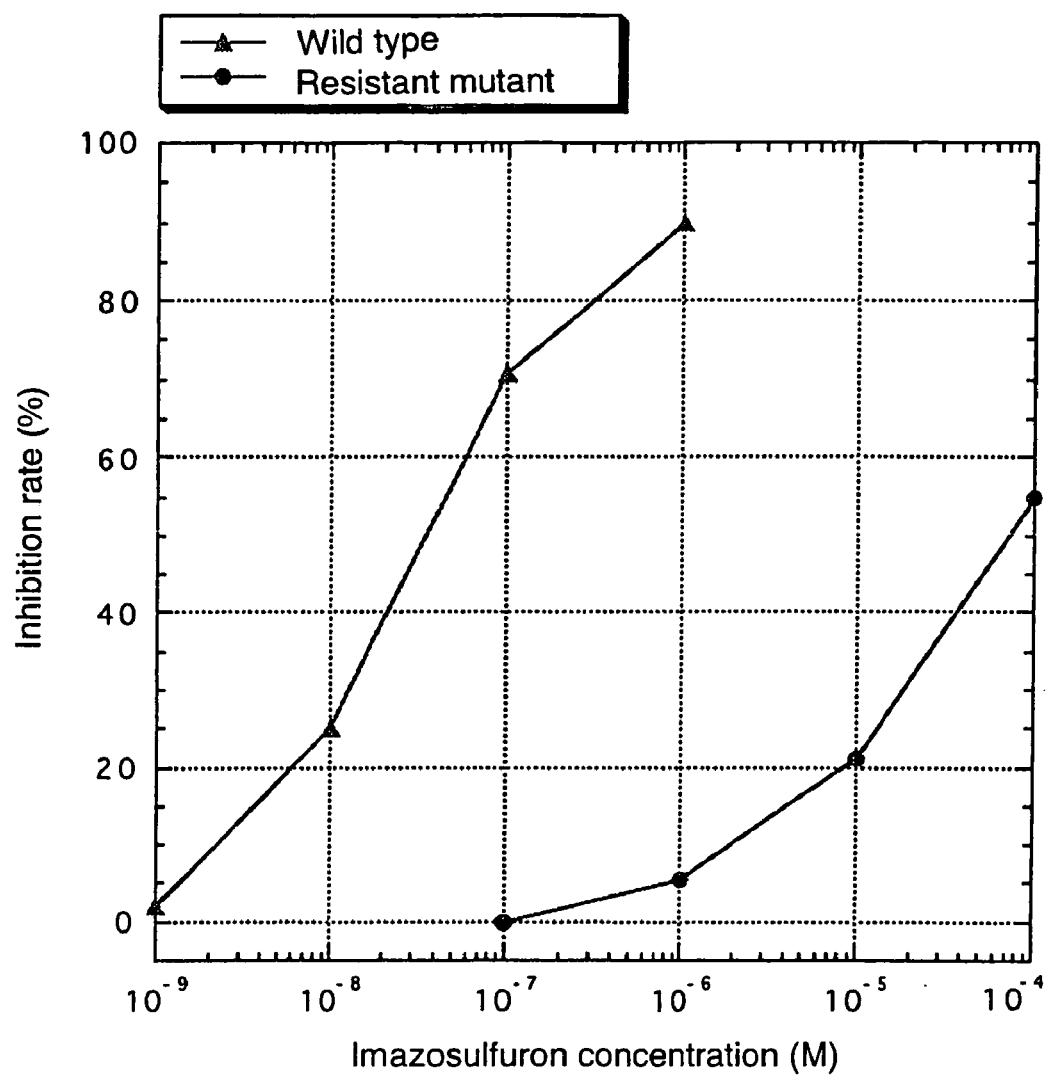
FIG. 18 is a characteristic figure showing sensitivity observed for the crude ALS obtained in Example 4 to imazosulfuron.
Figure 19:
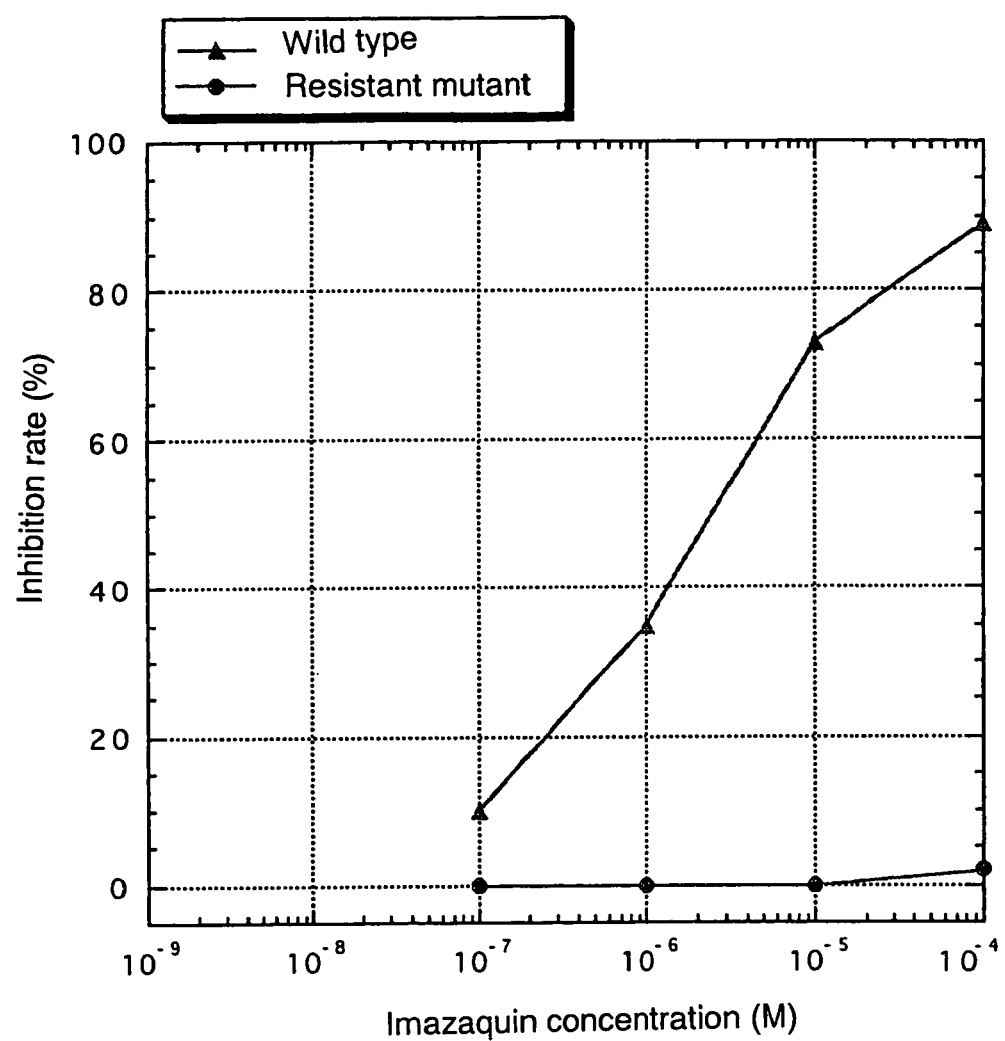
FIG. 19 is a characteristic figure showing sensitivity observed for the crude ALS obtained in Example 4 to imazaquin.
Figure 20:
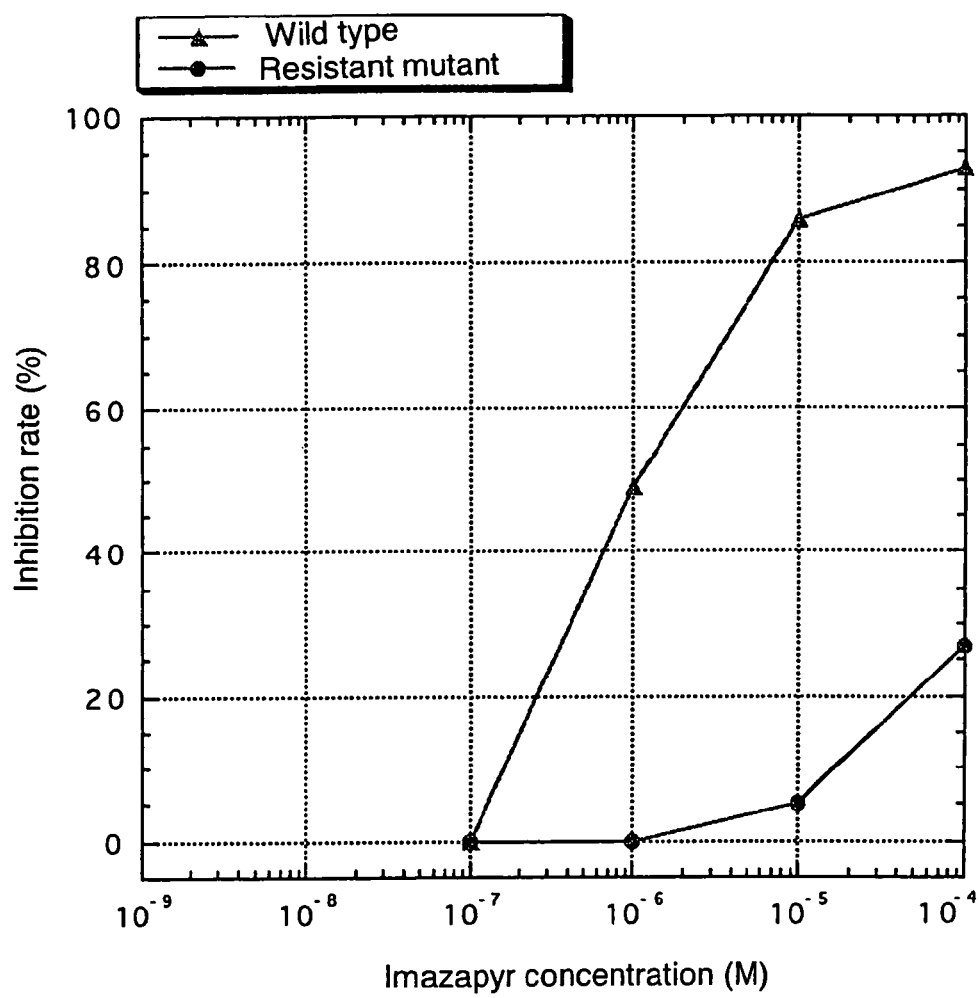
FIG. 20 is a characteristic figure showing sensitivity observed for the crude ALS obtained in Example 4 to imazapyr.

FIG. 14 shows the resulting sensitivity when pyrithiobac-sodium was used as a herbicide; FIG. 15 shows the resulting sensitivity when pyriminobac was used as a herbicide; FIG. 16 shows the resulting sensitivity when bensulfuron-methyl was used as a herbicide; FIG. 17 shows the resulting sensitivity when pyrazosulfuron-ethyl was used as a herbicide; FIG. 18 shows the resulting sensitivity when imazosulfuron was used as a herbicide; FIG. 19 shows the resulting sensitivity when imazaquin was used as a herbicide; and FIG. 20 shows the resulting sensitivity when imazapyr was used as a herbicide. In line graphs of FIGS. 12 to 20, the lines joining black triangles indicate the crude enzyme solution containing the wild type ALS protein, and those joining black squares indicate the crude enzyme solution containing the mutant ALS protein.

As shown in the FIGS. 14 to 20, the mutant ALS protein has good resistance to each of the herbicides, superior to that of the wild type ALS protein. Particularly, the mutant ALS protein has good resistance to PC herbicides. Further comparison of FIGS. 12, 14 and 15 indicates that the mutant ALS protein has the best resistance to bispyribac-sodium among PC herbicides.

Since these results can be thought to correlate with the result of Example 2, it was suggested that the factor which improved the resistance to PC-based herbicides in Example 2 is the mutant ALS gene.

Figure 21:
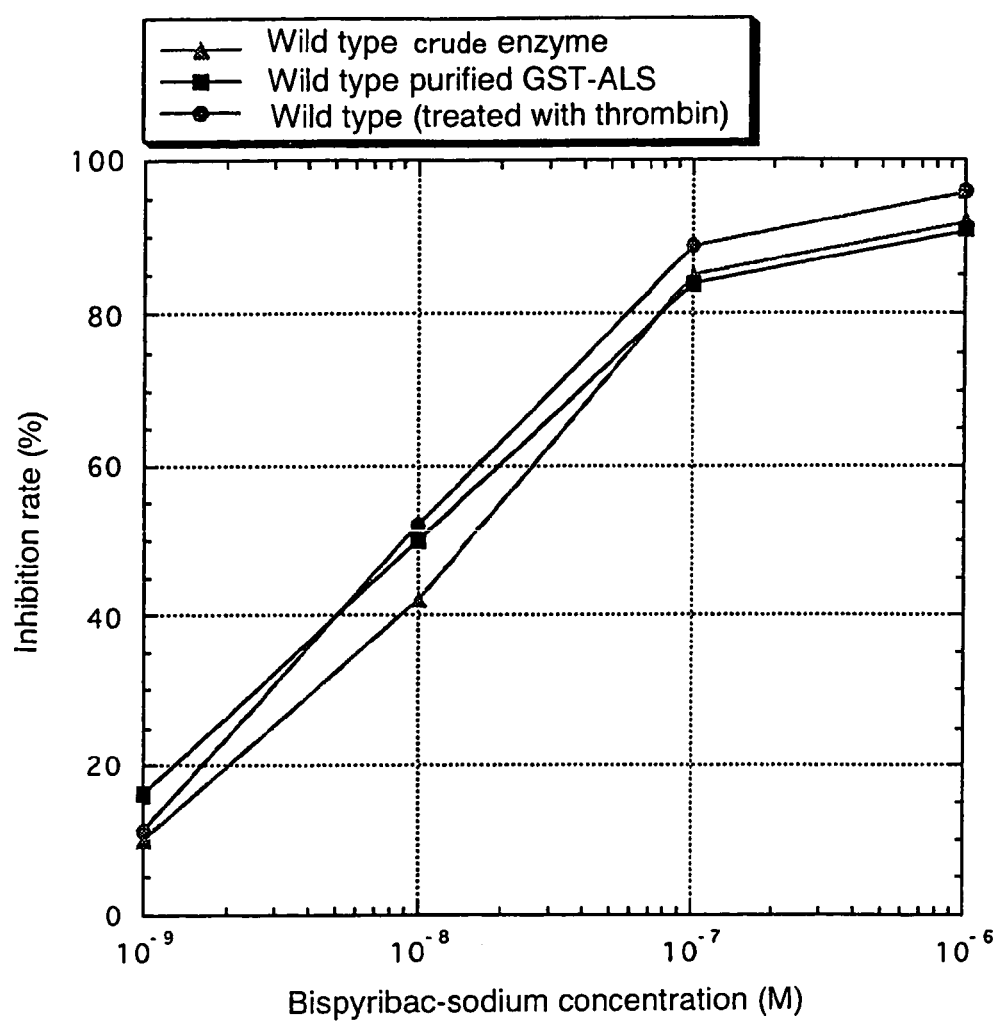
FIG. 21 is a characteristic figure showing sensitivity observed for the wild-type crude ALS, the wild-type purified GST-ALS and the wild-type GST-freed ALS obtained in Example 4 to bispyribac-sodium.
Figure 22:
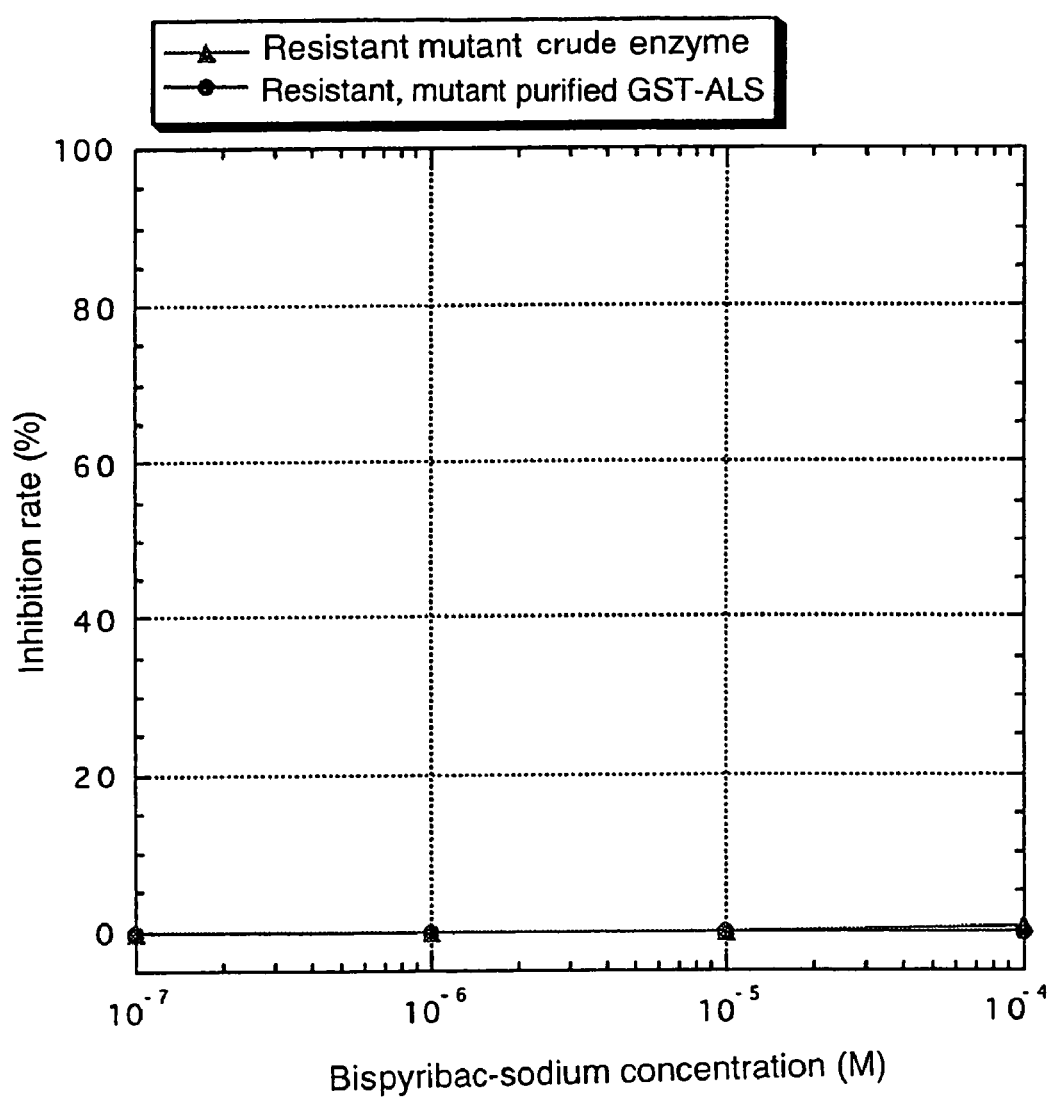
FIG. 22 is a characteristic figure showing sensitivity observed for the mutant crude ALS and the mutant purified GST-ALS obtained in Example 4, to bispyribac-sodium.
Figure 23:
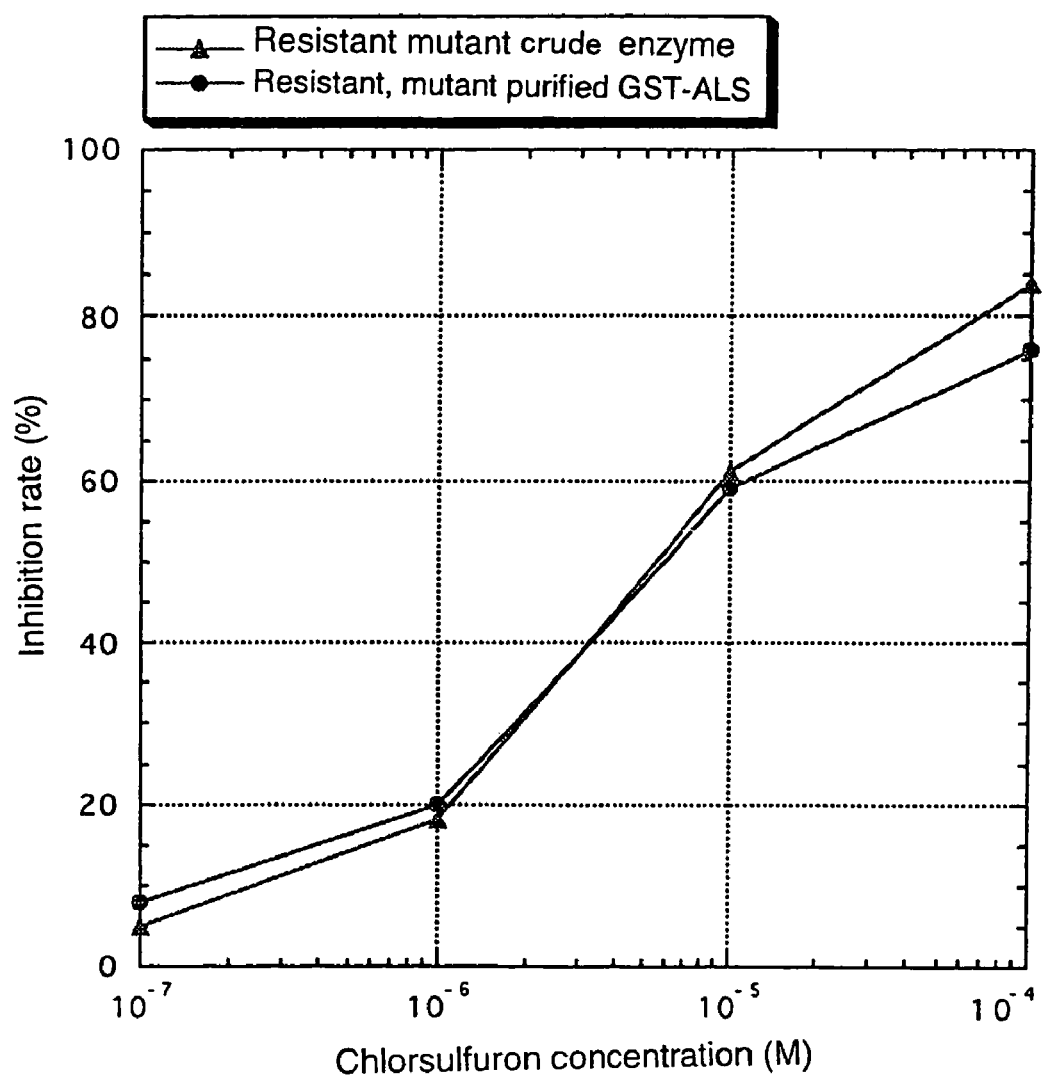
FIG. 23 is a characteristic figure showing sensitivity observed for the mutant crude ALS and the mutant purified GST-ALS obtained in Example 4, to chlorsulfuron.
Figure 24:
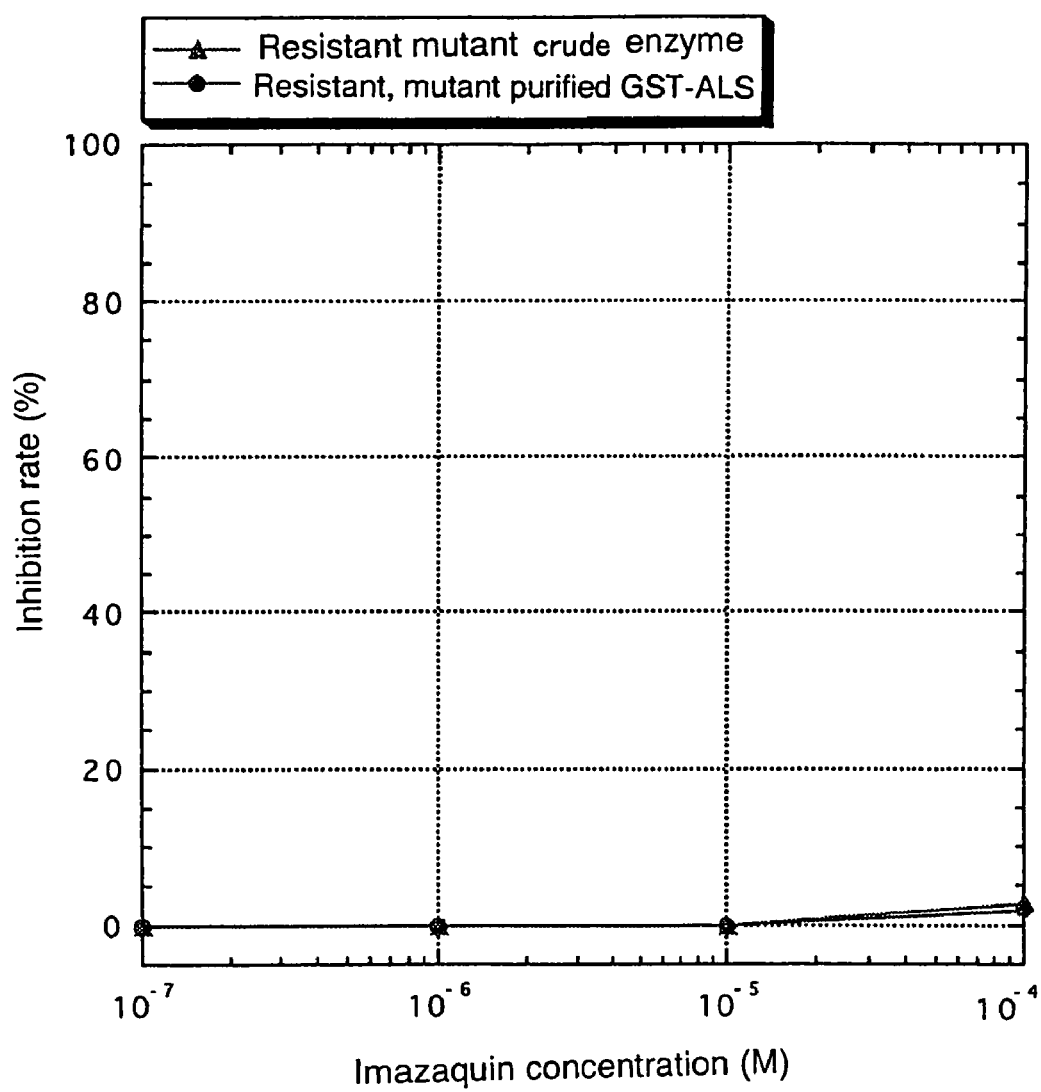
FIG. 24 is a characteristic figure showing sensitivity observed for the mutant crude ALS and the mutant purified GST-ALS obtained in Example 4, to imazaquin.

Furthermore, a herbicide sensitivity test was performed using the purified GST-ALS and the freed ALS prepared in Example 4. FIG. 21 shows a result indicating resistance of the wild type ALS protein to bispyribac-sodium. FIG. 22 shows a result indicating resistance of the mutant ALS protein to bispyribac-sodium. In addition, FIG. 23 shows a result indicating resistance of the mutant ALS protein to chlorsulfuron. FIG. 24 shows a result indicating resistance of the mutant ALS protein to imazaquin. Herbicide sensitivity tests whose results were shown in FIGS. 21 to 24 were performed without adding valine. Further in a line graph of FIG. 21, the line joining black triangles indicate the crude enzyme solution containing the wild type ALS protein; the line joining black squares indicates the wild type GST-ALS; and the line joining black circles indicates the freed ALS protein. In line graphs of FIGS. 22 to 24, the lines joining black triangles indicate the rough enzyme solution containing the mutant ALS protein, and the lines joining black squares indicate the mutant GST-ALS.

As shown in FIGS. 21 to 24, the purified GST-ALS also showed herbicide sensitivity similar to that in a case when the crude enzyme solution was used.

Example 6

Relation Between Mutated Portion in Mutant ALS Gene and Drug Sensitivity

The mutant portions in the mutant ALS gene determined in Example 3(4) were W548L mutation in which tryptophan (W) at position 548 of the wild type had been mutated to lysine (L) and S627I mutation in which serine (S) at position 627 of the wild type had been mutated to isoleucine (I) as shown in FIG. 1. To study the effect of these mutations on herbicide sensitivity, a mutant ALS gene containing only either one of the W548L or S627I mutations was prepared, and herbicide sensitivity of an ALS protein having either one of the mutations was examined.

(1) Preparation of Mutant Gene

Figure 25:
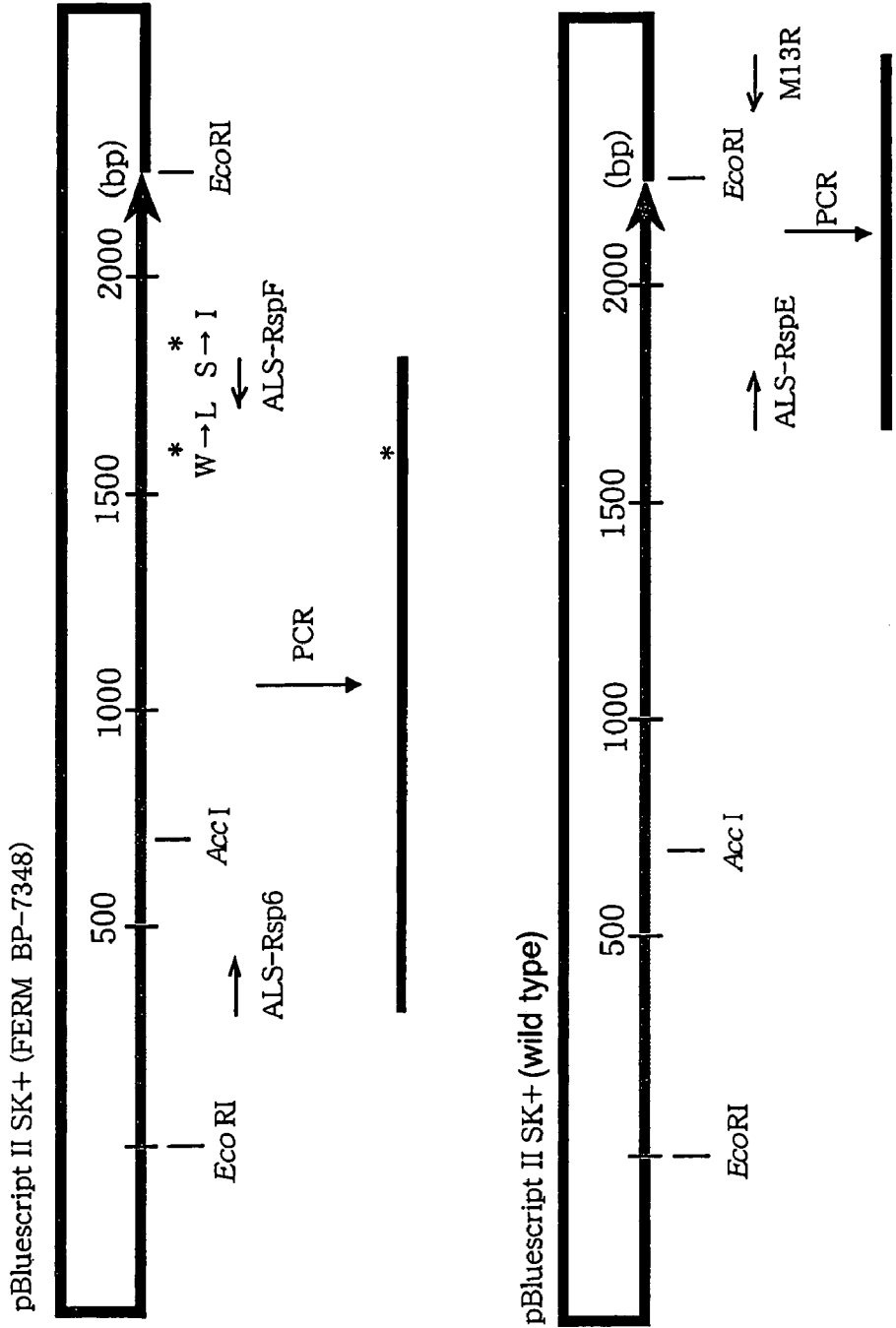
FIG. 25 shows the concept for generating the ALS gene having W548L mutation only.
Figure 26:
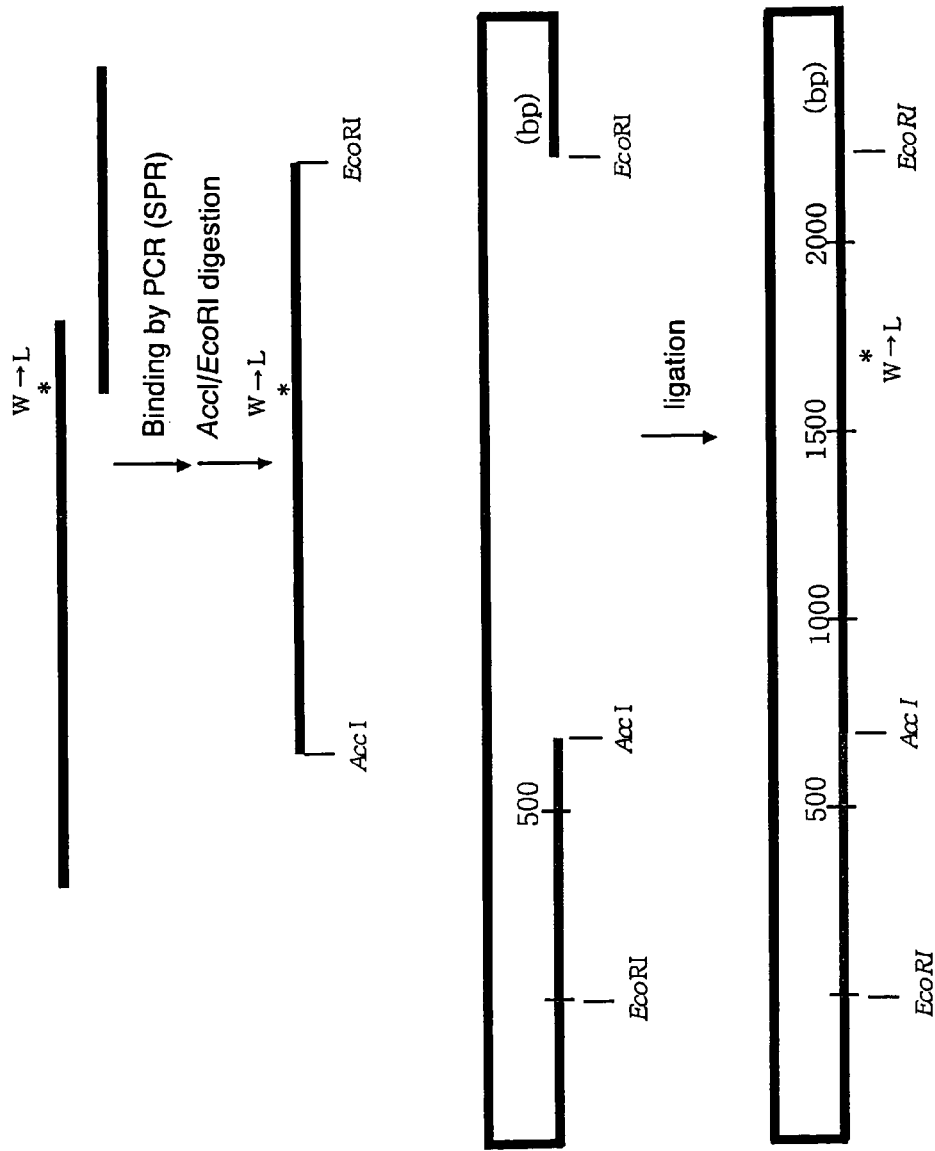
FIG. 26 is continued from FIG. 25 and shows the concept for generating the ALS gene having W548L mutation only.

For example, a mutant ALS gene (hereinafter referred to as "W548L mutant ALS gene") having W548L mutation only was prepared as shown in FIGS. 25 and 26. First, PCR was performed using a sense primer named ALS-Rsp6 (5'-CATCACCAACCACCTCTT-3': SEQ ID NO: 3) and an antisense primer named ALS-RspF (5'-ACACGGACTG-CAGGAATA-3': SEQ ID NO: 4), and using pBluescript II SK+ (FERM BP-7348) retaining the double-point mutant ALS gene as a template, thereby amplifying a DNA fragment having W548L mutation but having no S627I mutation (FIG. 25). Meanwhile, a DNA fragment containing a region encoding serine at position 627 was amplified using a sense primer named ALS-RspE (5'-TTACAAGGCGAAT-AGGGC-3': SEQ ID NO: 5) and a M13R antisense primer (5'-GGAAACAGCTATGACCATG-3': SEQ ID NO: 6) and using pBluescript II SK+ retaining the wild type ALS gene as a template (FIG. 25).

Next, a large DNA fragment was obtained from the two DNA fragments by linking the two DNA fragments using the SPR method (Gene preparation method: Self Polymerase Reaction in which two single-stranded DNAs are bound at the end portions, where sequences correspond to one another, and the DNAs are replicated by DNA polymerase using the DNAs as templates for each other to form a double-stranded DNA) (FIG. 26). The obtained DNA fragment was digested with Acc I and Eco RI, thereby obtaining an Acc I-Eco RI fragment. After pGEX-2T plasmid (pGEX-2T-wALS) containing a wild type ALS gene incorporated therein was digested at Acc I site, partial digestion was performed with Eco RI at 37° C. for 1 min, thereby obtaining a partial fragment of pGEX-2T plasmid (FIG. 26). Then, ligation of Acc I-Eco RI fragment and the partial fragment of pGEX-2T plasmid resulted in a plasmid having W548L mutant ALS gene.

In addition, a mutant ALS gene having only S627I mutation (hereinafter referred to as "S627I mutant ALS gene") could be obtained according to the method by which the above W548L mutant ALS gene was prepared. That is, S627I mutant ALS gene could be obtained in the same manner as in the method employed for the above W548L mutant ALS gene except that ALS-RspE and M13R were used as primers in PCR performed using pBluescript II SK+ (FERM BP-7348) as a template, and ALS-Rsp6 and ALS-RspF were used as primers in PCR performed using pBluescript II SK+ retaining the wild type ALS gene as a template.

A plasmid having W548L mutant ALS gene and a plasmid having S627I mutant ALS gene were separately transformed into *E. coli* strain JM 109. Full sequencing of the ALS gene was performed for the obtained *E. coli* colonies, so that the single-point mutation of W548L mutation and that of S627I mutation could be confirmed.

(2) Herbicide resistance of respective mutant proteins

A plasmid having W548L mutant ALS gene or a plasmid having S627I mutant ALS gene was transformed into *E. coli* strain JM 109. The colonies obtained from transformation were subjected to liquid culture, expression of GST induction protein was induced in the same manner as in Examples 4 and 5, a crude enzyme solution was prepared, and then herbicide sensitivity of ALS was examined in the presence of 1 mM valine.

Figure 27:
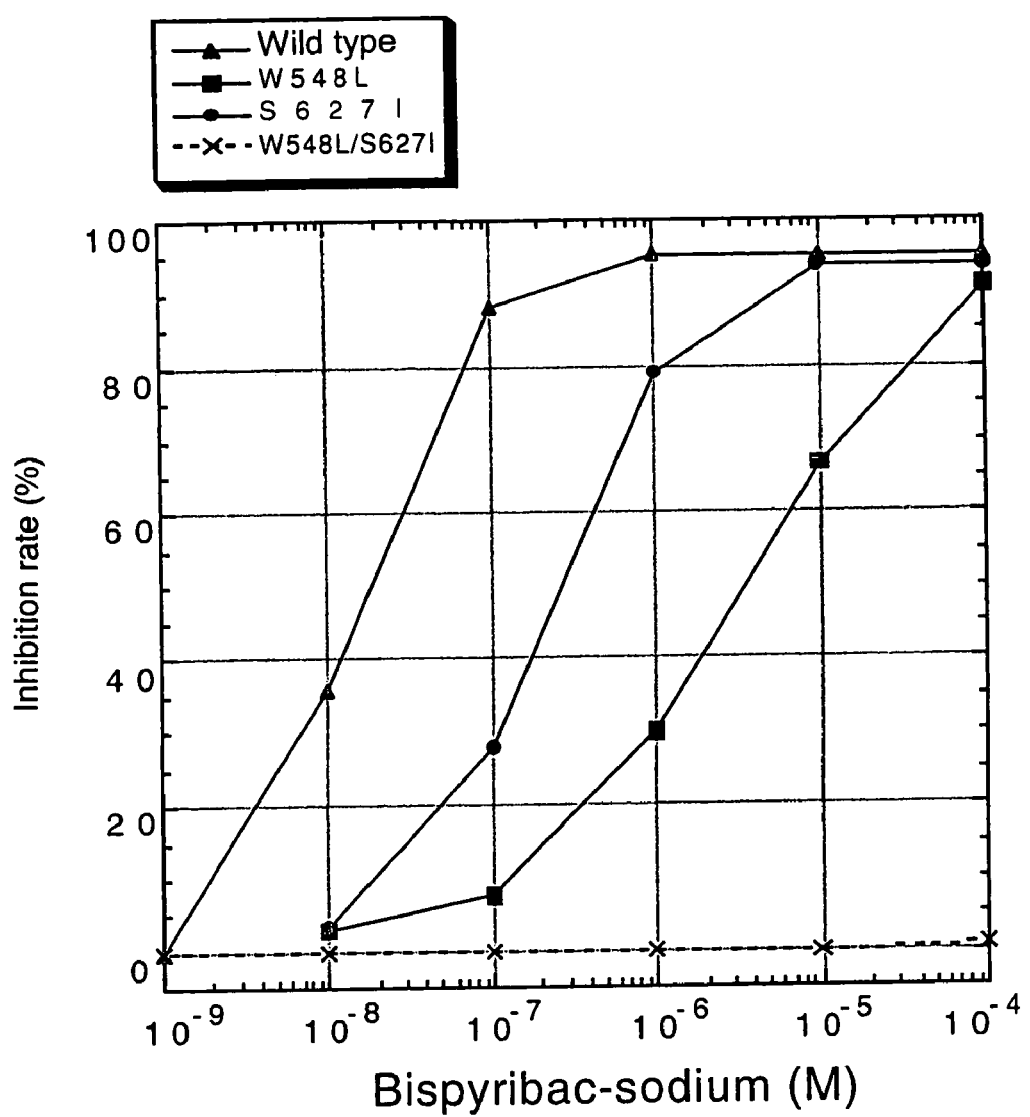
FIG. 27 is a characteristic figure showing sensitivity observed for the crude ALS obtained in Example 6 (2) to bispyribac-sodium.
Figure 28:
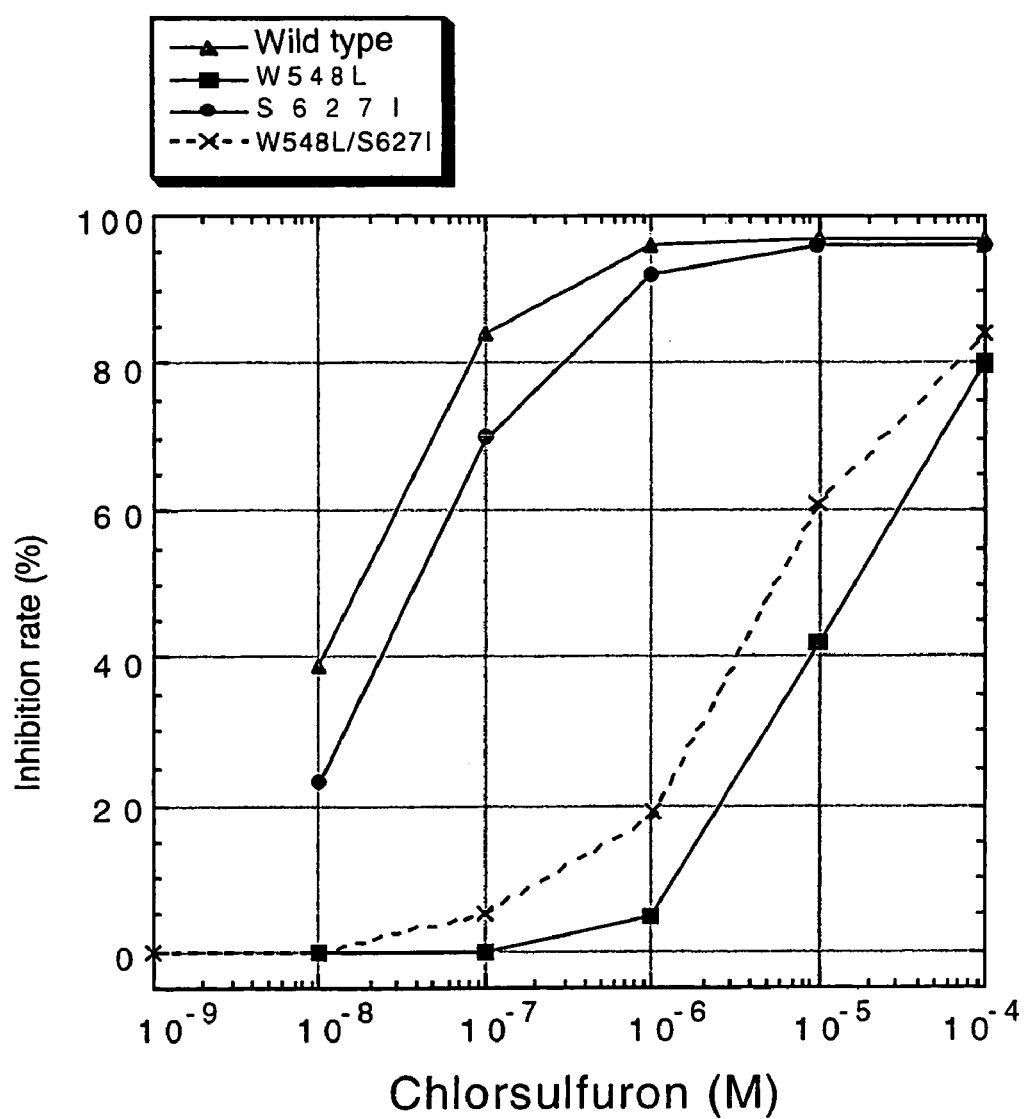
FIG. 28 is a characteristic figure showing sensitivity observed for the crude ALS obtained in Example 6 (2) to chlorsulfuron.
Figure 29:
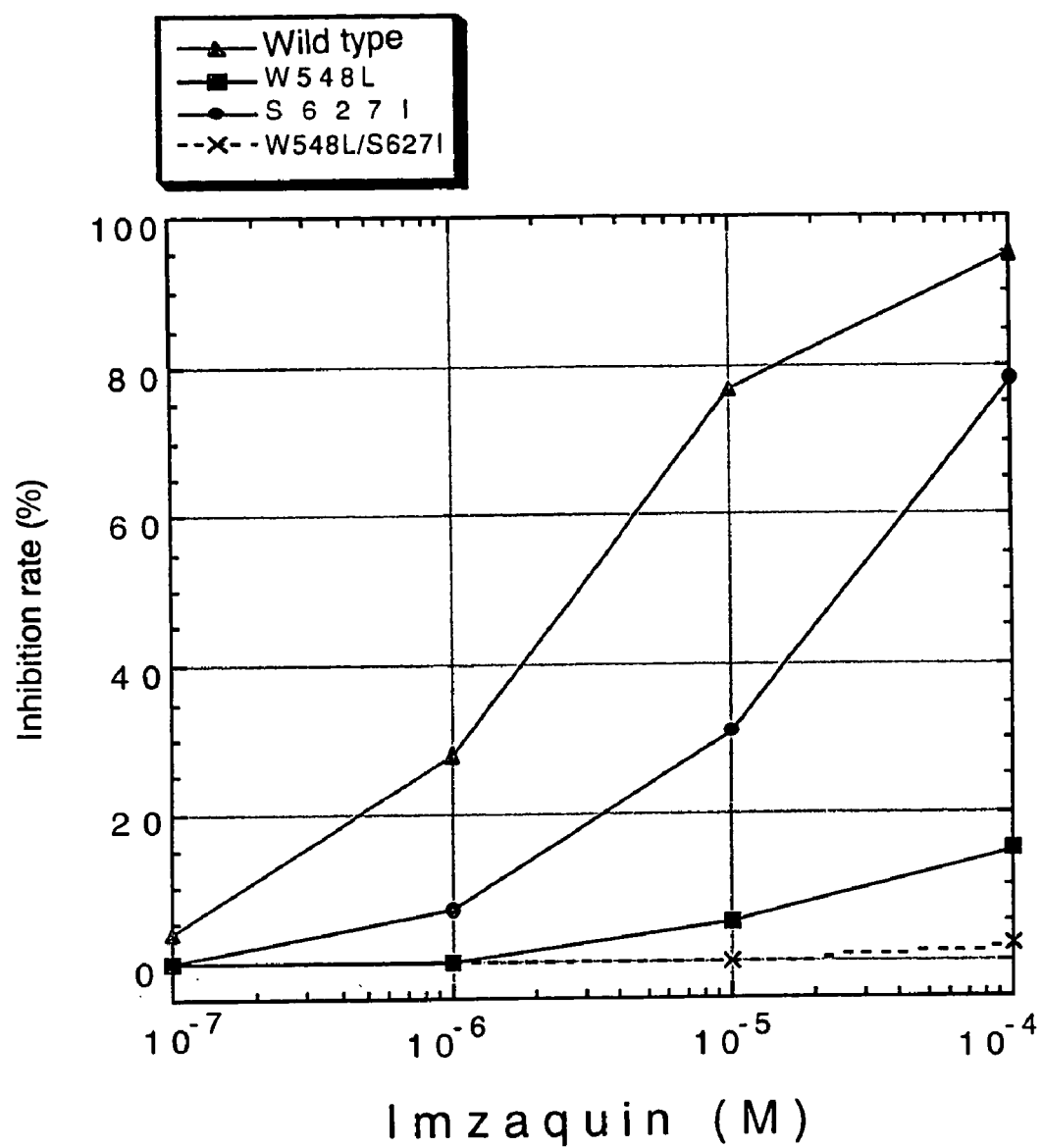
FIG. 29 is a characteristic figure showing sensitivity observed for the crude ALS obtained in Example 6 (2) to imazaquin.

FIG. 27 shows the result of the use of bispyribac-sodium. FIGS. 28 and 29 show the result of the use of chlorsulfuron and imazaquin. As shown in FIG. 27 for bispyribac-sodium, each single-point mutation of W548L mutation and of S627I mutation imparted resistance against bispyribac-sodium, and the degree of resistance was higher in the single-point mutation of only W548L than that in the single-point mutation of only S627I.

However, the degrees of resistance among these single-point mutations were all shown to be several magnitudes lower than those of the double-point mutations shown in Example 5. In other words, coexistence of W548L and S627I mutations resulted in significantly strong resistance to bispyribac-sodium which could not be predicted from the case of either W548L or S627I mutation alone.

When chlorsulfuron was used (FIG. 28), W548L mutation alone imparted resistance to chlorsulfuron, but S627I mutation alone imparted no obvious resistance. In addition, a comparison of the degree of resistance to chlorsulfuron between W548L mutation alone, and W548L mutation and S627I mutation together revealed that they shared the same degree of resistance. Moreover, when imazaquin was used (FIG. 29), results were similar to those for bispyribac-sodium. However in the concentration range employed in this example, increased resistance, being a multiplier effect due to co-existence of two mutations, could not be confirmed.

As described above, a novel S627I mutation which was found this time was shown to drastically enhance bispyribac-sodium resistance due to W548L mutation. In conclusion, ALS gene having W548L and S627I mutations is a gene imparting high resistance specific to bispyribac-sodium.

Example 7

Production of Transformant Plant

A rice plant (Nippon-bare) was transformed with the mutant ALS gene determined in Example 3(4), and then bispyribac-sodium resistance of the transformant rice plant was examined.

(1) Construction of Binary Vector With the Mutant ALS Gene Incorporated Therein

The mutant ALS gene obtained in Example 3(4) was incorporated into a binary vector, pMLH7133 (Mitsuhara et al., Plant Cell Physiol. 37 49–59, 1996), which had been developed for transformation of a rice plant.

Figure 30:
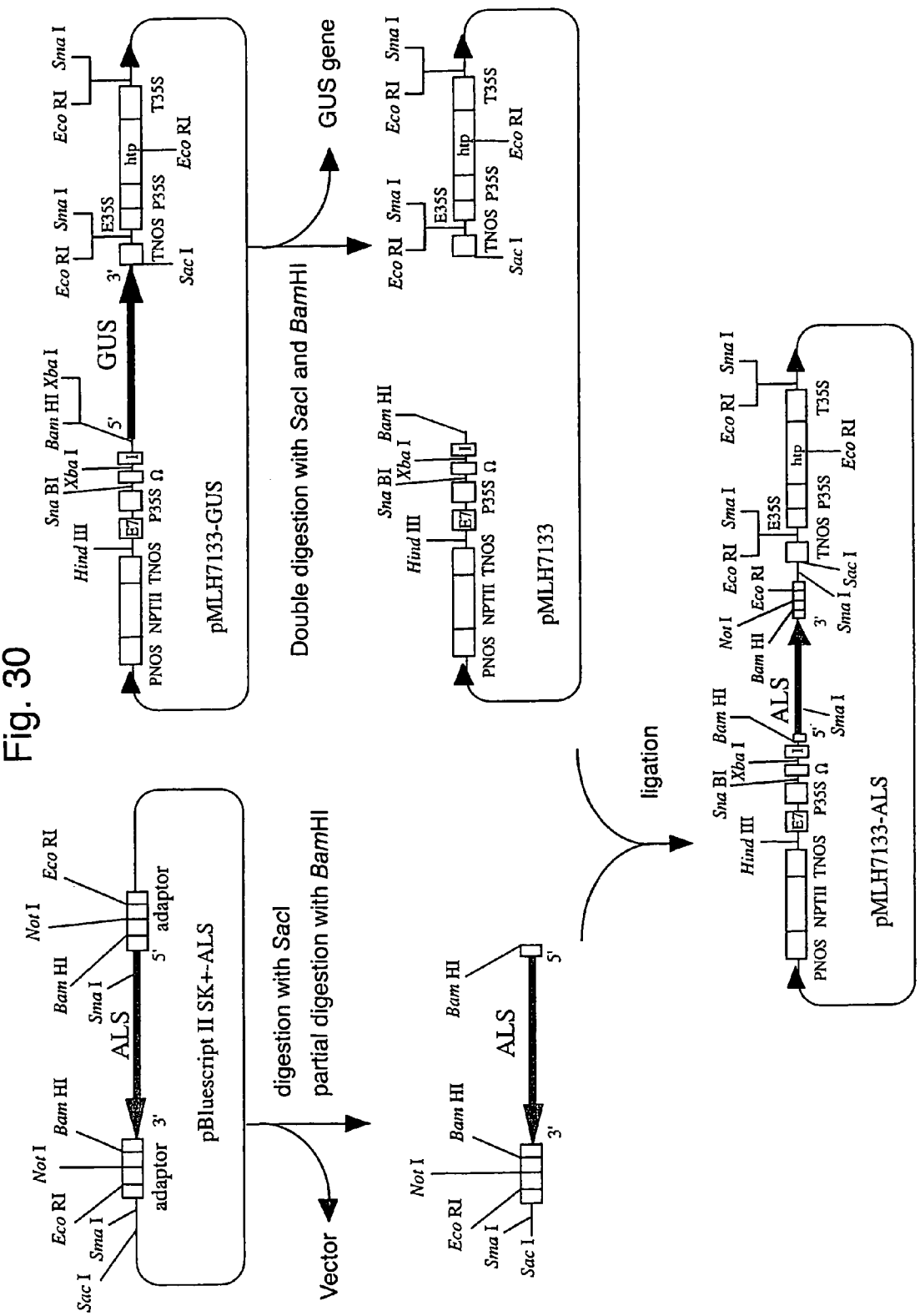
FIG. 30 shows the concept for constructing the binary vector constructed in Example 7.

First as shown in FIG. 30, the mutant ALS gene incorporated in pBluescript II SK+ (FERM BP-7348) was cleaved out using the restriction enzyme cleavage site of a multicloning site and the cleavage site of an adaptor (digestion with Sac I and partial digestion with Bam HI). Then, pMLH7133 was digested with Sac I and Bam HI. GUS region in pMLH7133 was excised and pMLH7133 was linearized. A DNA fragment containing mutant ALS gene and pMLH7133 in the shape of a straight chain were ligated, thereby obtaining pMLH7133-ALS.

Figure 31:
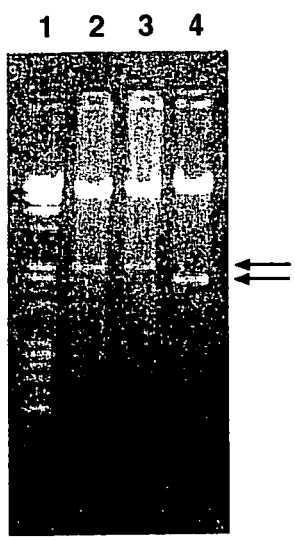
FIG. 31 is a photograph of electrophoresis by which the ALS gene insert was confirmed in the plasmid isolated from the single colony of E. coli (JM109), wherein lane 1 indicates λHind III/100 bp DNA marker, lane 2 indicates a plasmid derived from E. coli that has been transformed with pMLH7133 retaining the mutant ALS gene, lane 3 indicates a plasmid derived from E. coli that has been transformed with pMLH7133 retaining the wild type ALS gene, lane 4 indicates pMLH7133 retaining a GUS gene (control group), and arrows indicate the insert DNA.
Figure 32:
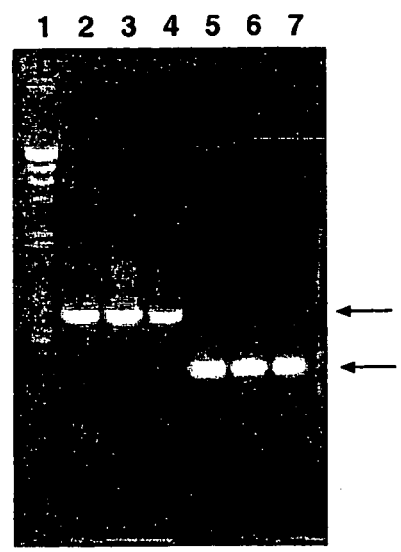
FIG. 32 is a photograph of electrophoresis showing the result of PCR using plasmid DNAs as a template, wherein lane 1 indicates λHind III/100 bp DNA marker, lanes 2 and 5 indicate a pBI 121 plasmid (control group) retaining the wild type ALS gene, lanes 3 and 6 indicate pMLH7133 which is thought to retain the mutant ALS gene, lanes 4 and 7 indicate pMLH 7133 which is thought to retain a wild type ALS gene, and arrows indicate PCR products.
Figure 33:
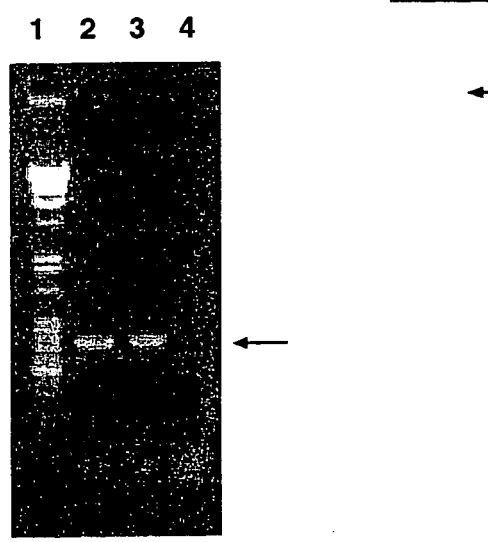
FIG. 33 is a photograph of electrophoresis showing the result of confirming the insertion orientation of ALS gene, wherein lane 1 indicates λHind III/100 bp DNA marker, lane 2 indicates pMLH7133 retaining a mutant ALS gene, lane 3 indicates pMLH7133 retaining a wild type ALS gene, lane 4 indicates pMLH7133 (control group) retaining a GUS gene, and arrows indicate PCR products.

The obtained pMLH7133-ALS was transformed into *E. coli* strain JM105. The resulting single colony was subjected to liquid culture, and then a plasmid was prepared. The presence or absence of the insert was confirmed by digesting the prepared plasmid using Sac I and Bam HI (FIG. 31), so that clones having mutant ALS genes were selected. PCR was performed using plasmids shown to contain the insert as templates and using two sets of primers which allow specific amplification of at least part of the mutant ALS gene. The primer sets used herein were a set of an ALS-Rsp1 sense primer (5'-GCTCTGCTACAACAGAGCACA-3':SEQ ID NO: 7) and a 4-83-3 antisense primer (5'-GCTTTGCCAA-CATACAG-3':SEQ ID NO: 8); and a set of a 3-1-4 sense primer (5'-AGGTGTCACAGTTGTTG-3':SEQ ID NO: 9) and a 3-1-1 antisense primer (5'-GCATCTTCTTGAATG-GCG-3': SEQ ID NO: 10). Thus, specific fragment bands were detected (FIG. 32), suggesting that the mutant ALS gene obtained in Example 3(4) was incorporated into the pMLH7133 vector.

Further, whether or not the mutant ALS gene had been incorporated normally was confirmed by PCR to learn the insertion orientation of the insert and to determine the sequence. The insertion orientation of the insert was confirmed by PCR as described below. pMLH7133-ALS was completely digested with Eco RI, thereby removing TNOS portion and linearizing. PCR was performed using the product as a template and using the above set of ALS-Res1 and 4-83-3 and the set of 3-1-4 and 3-1-1. As a result (F 33), bands for the PCR products were confirmed at positions as predicted, suggesting that the mutant ALS gene was inserted in forward orientation. If the mutant ALS gene is inserted in reverse orientation, PCR product would not be detected since the mutant ALS gene portion is cut out from pMLH7133-ALS by Eco RI digestion and no DNA fragment is amplified.

Meanwhile, determination of the sequence was performed using the prepared pMLH7133-ALS as a template for the linkage region of the 5' side of a mutant ALS gene and pMLH7133. In addition, since pMLH7133-ALS leads to low number of copies in *E. coli*, preparation was performed by the alkali SDS method from a culture solution in a volume 20 fold greater than the standard volume (corresponding to 2 ml of culture solution×20). Therefore, mutant ALS genes were shown that they have been inserted in forward orientation.

(2) Introduction of Binary Vector Into *Agrobacterium*

The binary vector (pMLH7133-ALS) obtained in (1) above was introduced into Agrobacteria as follows. The competent cells of *Agrobacterium tumefaciens* EHA 105 stored at −80° C. were thawed in ice and used. pMLH7133-ALS was added to a solution containing the competent cells of *Agrobacterium tumefaciens* EHA 105, and allowed to stand in ice for 15 min, followed by heat shock at 37° C. for 5 min. Then, the mixture was allowed to stand in ice for 2 min, and 1 ml of a SOC liquid medium was added thereto, followed by gentle shaking at 28° C. for 2 to 4 hours. Next, centrifugation was performed, and most of the supernatant was discarded. The precipitated cells were suspended in the remaining supernatant. The suspension was coated over a LB plate containing 50 ppm each of kanamycin and hygromycin, followed by incubation at 28° C. for 2 to 3 days, thereby obtaining single colonies.

(3) Transformation of Rice Plant with pMLH 7133-ALS-Introduced *Agrobacterium*

A ½ spoonful of the Agrobacteria obtained in (2) was taken with a sterilized micro spatula, and then suspended well in 30 ml of an AAM medium (Falcon tube) supplemented with acetosyringone at a concentration of 10 mg/l as shown in Table 6.

TABLE 6

| $MgSO_4$—$7H_2O$ | 250 | $CaCl_2$—$2H_2O$ | 150 |
|---|---|---|---|
| $NaH_2PO_4$—$2H_2O$ | 150 | KCl | 3000 |
| Fe-EDTA | 40 | $MnSO_4$—$6H_2O$ | 10 |
| $ZnSO_4$—$7H_2O$ | 2 | $CuSO_4$—$5H_2O$ | 0.025 |
| $CoCl_2$—$6H_2O$ | 0.025 | KI | 0.75 |
| $H_3BO$ | 3 | $Na_2MoO_4$—$2H_2O$ | 0.25 |
| Myo-inositol | 100 | Nicotinic acid | 1 |
| Pyridoxine-HCl | 1 | Thiamine-HCl | 10 |
| Casamino acid | 500 | Glycine | 7.5 |
| L-Arginine | 176.7 | L-Glutamine | 900 |
| L-Aspartic acid | 300 | Sucrose | 68.5 |
| Glucose | 36 | | |
| pH | 5.2 | | |

(Numerical figures are shown with mg/l)

Pipetting was performed well with a Pasteur pipette so that no mass of Agrobacteria remained. The obtained suspension was put into a 9 cm Schale.

Calli which had been induced from seeds (Nippon-bare) and pre-cultured in a N6D medium shown in Table 7 were put into a stainless mesh (or a tea strainer). Then the mesh containing the calli was dipped in the suspension of Agrobacteria for 1.5 to 2 min. At this time, the mesh was dipped such that the calli were entirely immersed in the bacterial solution, followed by gentle agitation with a spatula. Subsequently, the stainless mesh was placed on a sterilized filter paper to remove excessive bacterial solution. The thus treated calli were placed on a 2N6AS solid medium (10 mg/l acetosyringone, 16 calli per petri dish) as shown in Table 8, sealed with a surgical tape, and cultured under dark conditions at 28° C. for 2 to 3 days, until the calli were covered with a thin layer of the cells (due to the growth of the cells).

TABLE 7

| CHU powder | 1 pack |
|---|---|
| Myo-inositol | 100 |
| Nicotinic acid | 0.5 |
| Pyridoxine-HCl | 0.5 |
| Thiamine-HCl | 1 |
| 2,4-D | 2 |
| Casamino acid | 300 |
| Glycine | 2 |
| Proline | 2827 |
| Sucrose | 30000 |
| gelrite | 4000 |
| carbenicillin | 500 |
| hygromycin | 50 |
| pH | 5.8 |

(Numerical figures are shown with mg/l)

TABLE 8

| CHU powder | 1 pack |
|---|---|
| Myoinositol | 100 |
| Nicotinic Acid | 0.5 |
| Pyridoxine-HCl | 0.5 |
| Thiamine-HCl | 1 |
| 2,4-D | 2 |
| Casamino acid | 300 |
| Glycine | 2 |
| Sucrose | 30 g |
| Glucose | 10 g |
| gelrite | 4000 |
| acetosyringone | 10 |
| pH | 5.2 |

(Numerical figures are shown with mg/l)

After the calli were coated with a thin layer of the cells as a result of cocultivation for 3 days, the calli were washed to remove the Agrobacteria by the following method. The calli treated as described above were put into a stainless mesh (or a tea strainer), and the mesh containing the calli was dipped in a N6D liquid medium (containing 500 mg/l carbenicillin). Exchanging of the petri dish was continued until the medium was no longer cloudy. Agrobacteria attached to the calli were washed away by this treatment. Then, the mesh was placed on a sterilized filter paper to remove excessive moisture. The calli were placed on a N6D solid medium (containing 500 mg/l carbenicillin and 50 mg/l hygromycin), and then cultured under light conditions at 28° C. for 2 to 3 weeks. In addition, when Agrobacteria proliferated again after the procedure, washing was performed in the same manner and then the calli were placed on a new medium.

Figure 34:
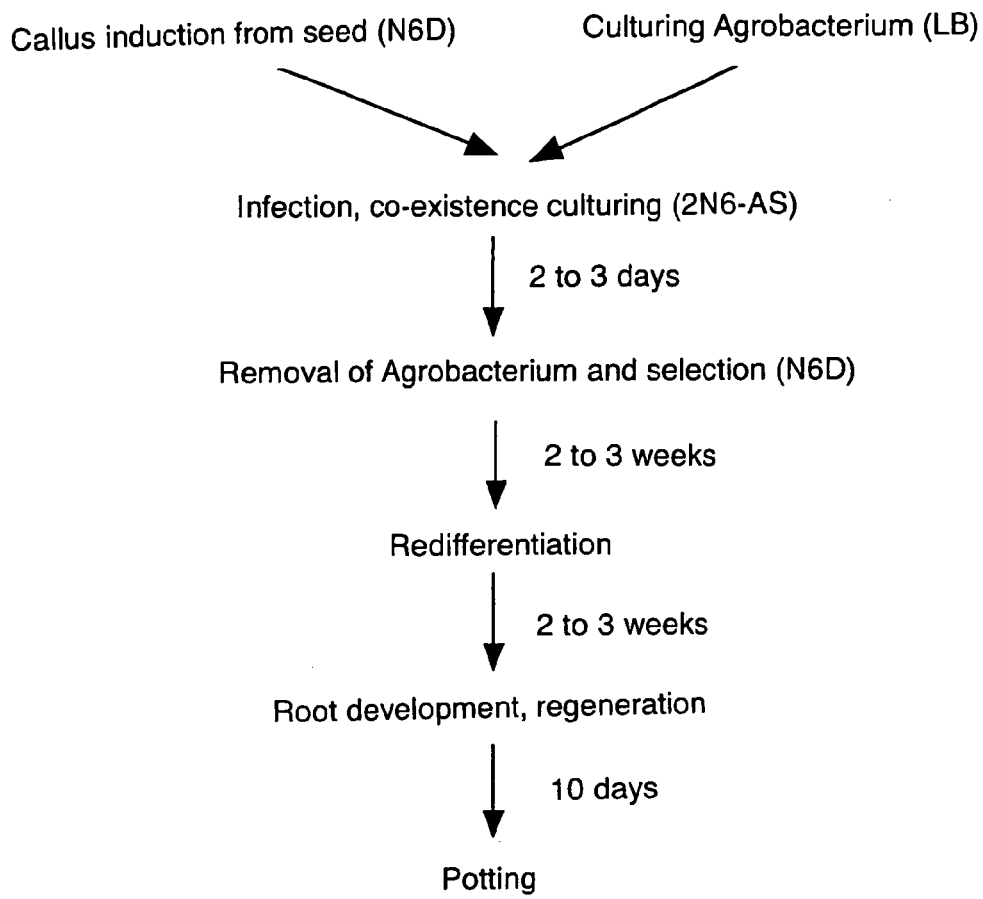
FIG. 34 is a flow chart showing the method for transforming rice plants (Nippon-bare) using Agrobacterium.

After selection by culturing under light conditions at 28° C. for 2 to 3 weeks, the calli were transplanted, 9 calli per petri dish, on redifferentiation media (containing 250 mg/l carbenicillin and 50 mg/l hygromycin) and then cultured under light conditions at 28° C. for 2 to 3 weeks. When portions of leaves, stems and roots differentiated respectively 1 cm or more, the calli were transplanted, 2 to 3 calli per petri dish onto hormone free media (containing 50 mg/l hygromycin). Subsequently when the obtained plant bodies proliferated to spread over the petri dish enough, the plants were potted into culture soil (bon sol) and allowed to acclimate. Upon transplantation, media attached to roots were completely washed away in water. FIG. 34 shows the flow of the above procedures.

Figure 35:
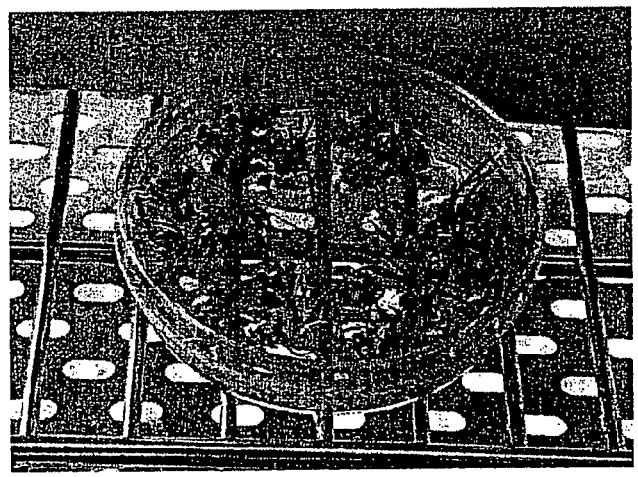
FIG. 35 is a photograph showing rice plants (Nippon-bare) under redifferentiation from calli.
Figure 36:
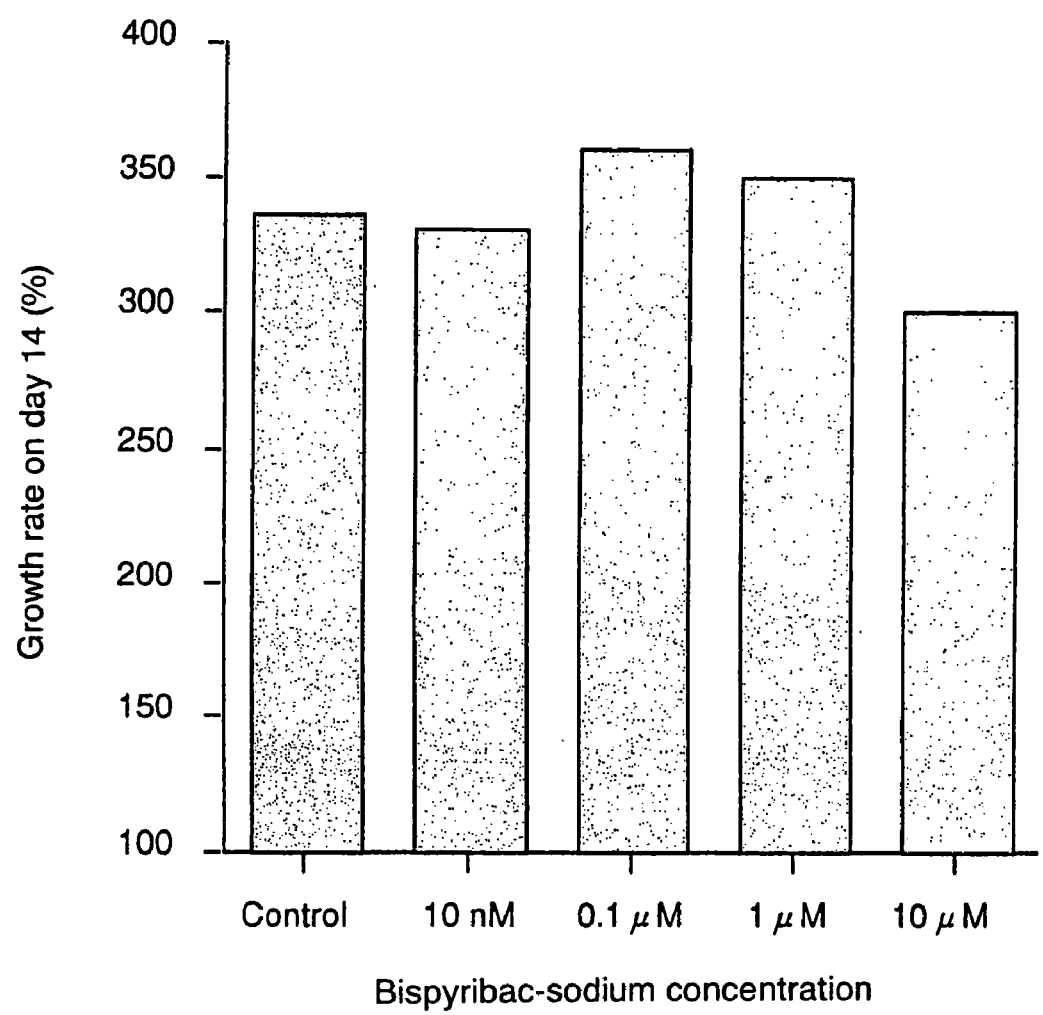
FIG. 36 is a characteristic figure showing bispyribac-sodium sensitivity of the callus of a rice plant (Nippon-bare) transformed with a mutant ALS gene.
Figure 37:
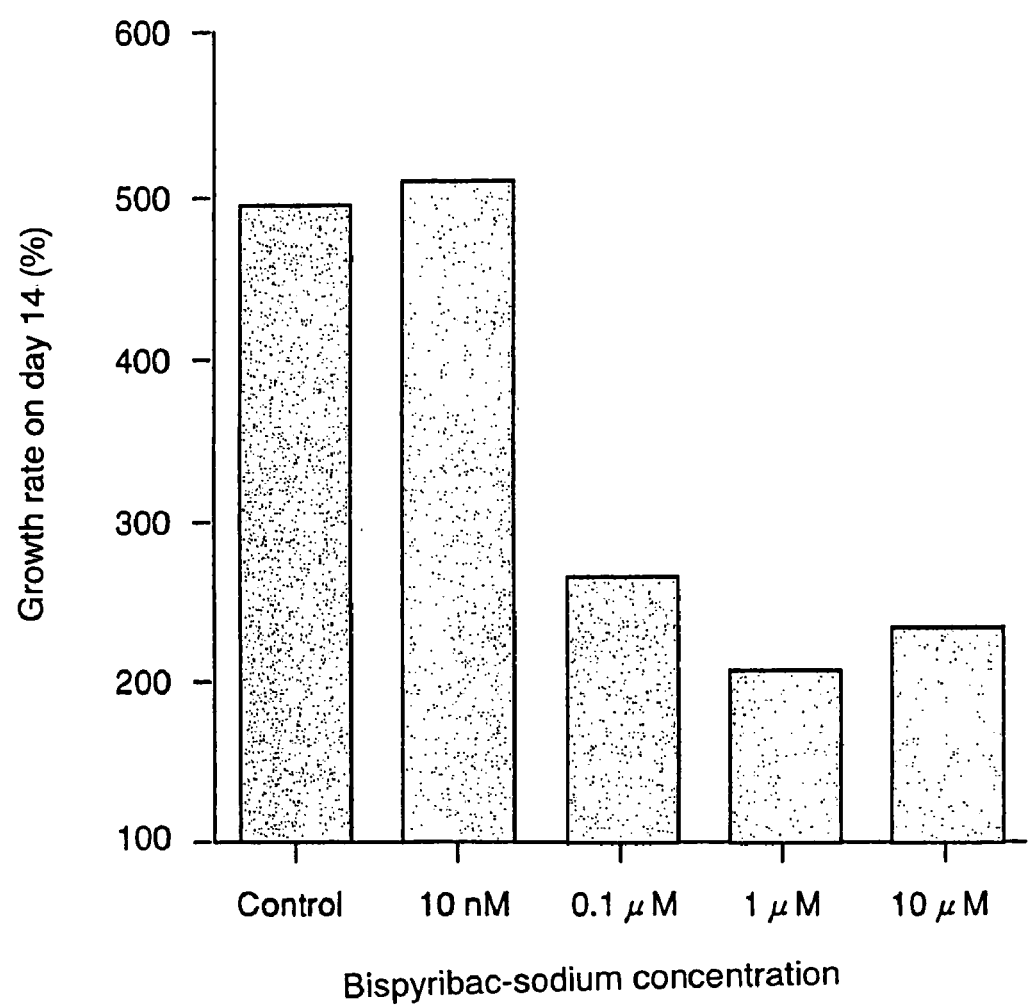
FIG. 37 is a characteristic figure showing bispyribac-sodium sensitivity of the callus of the wild type rice plant (Nippon-bare).

Simultaneously with the above described potting, part of the calli which had not redifferentiated (9 calli) (FIG. 35) was sub-cultured on solid media for production of a bispyribac-sodium resistant callus used in Example 1. The solid media contained 10 µM bispyribac-sodium. Thus, 6 out of 9 calli grew normally. One of the 6 calli that grew normally and showed bispyribac-sodium resistance was subjected to liquid culture, and then the drug sensitivity to bispyribac-sodium was examined in detail. Therefore, as shown in FIG. 36, the callus showed bispyribac-sodium resistance, almost identical to that of bispyribac-sodium resistant Sr line, from which the double-point mutant gene had been derived. Further, as shown in FIG. 37, the callus of the wild type rice plant (Nippon-bare) showed bispyribac-sodium sensitivity. Accordingly, 6 calli grown on a solid medium containing 10 µM bispyribac-sodium were all shown to have strong bispyribac-sodium resistance.

Figure 38:
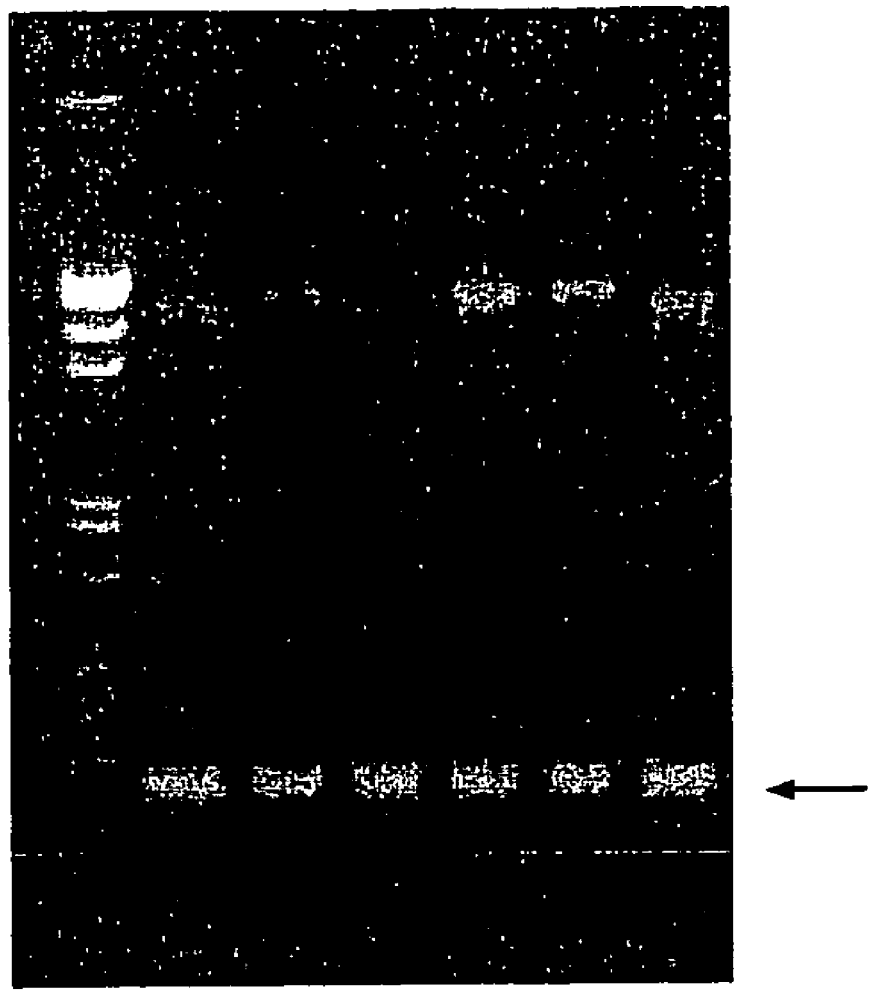
FIG. 38 is a photograph of electrophoresis showing the results of PCR performed using genomic DNA prepared from a transformant callus, wherein lane 1 indicates λHind III/100 bp DNA marker, lanes 2 to 7 show the respective results of PCR using genomic DNAs derived from different calli, and arrow indicates the PCR products.

Genomic DNA was prepared from these bispyribac-sodium resistant calli using a DNeasy Plant Kit (QIAGEN). Then, PCR was performed using the genomic DNA as a template and using a set of a sense primer (3-1-4: SEQ ID NO: 9) and an antisense primer (4-83-3: SEQ ID NO: 8) that flank the double-point mutation portion therebetween. Thus, as shown in FIG. 38, a DNA fragment was amplified as expected. The amplified DNA fragment was purified, and then the nucleotide sequence was examined (a primer (3-1-4: SEQ ID NO: 9) was used to read the sense strand; and a primer (ALS-Rsp2: 5'-AGTCCTGCCATCACCATCCAG-3': SEQ ID NO: 11) was used to read the antisense strand).

Figure 39A:
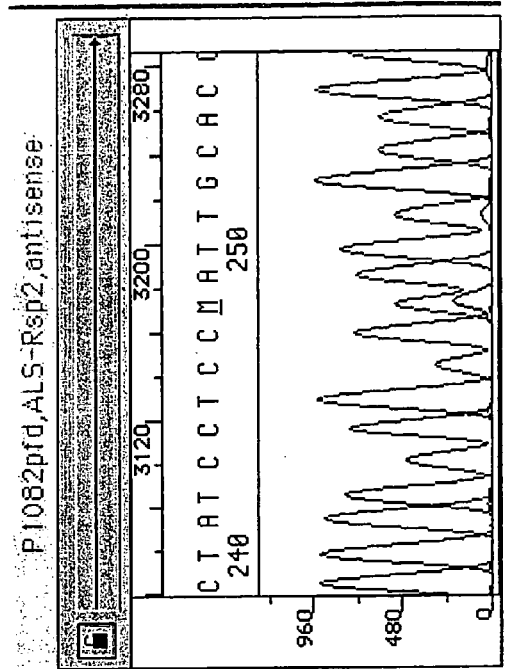
FIG. 39 is a characteristic figure showing the result of sequencing of the PCR product resulting from PCR using the genomic DNA prepared from the transformant callus as a template, wherein A shows the result of analysis of the periphery of an amino acid residue 548 using a sense primer (3-1-4), B shows the result of analysis of the periphery of an amino acid residue 548 using an antisense primer (ALS-Rsp2), C shows the result of analysis of the periphery of an amino acid residue 627 using a sense primer (3-1-4), and D shows the result of analysis of the periphery of an amino acid residue 627 using an antisense primer (ALS-Rsp2).
Figure 39B:
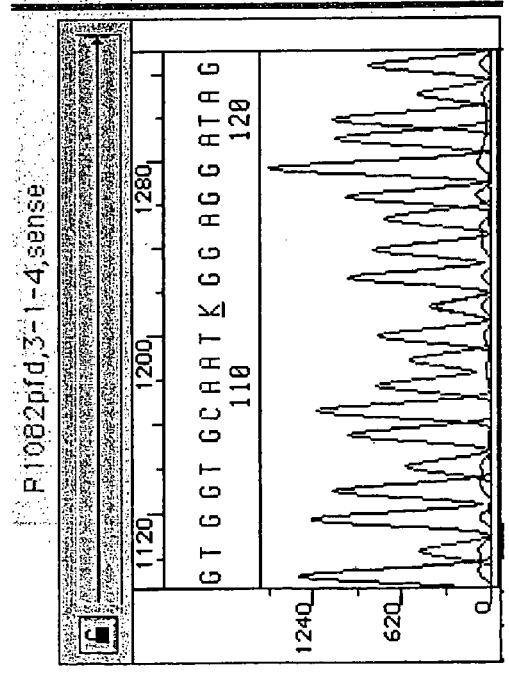
Figure 39C:
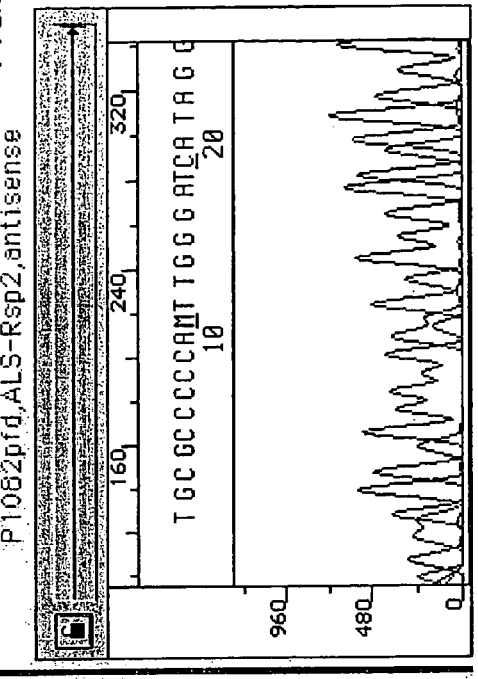
Figure 39D:
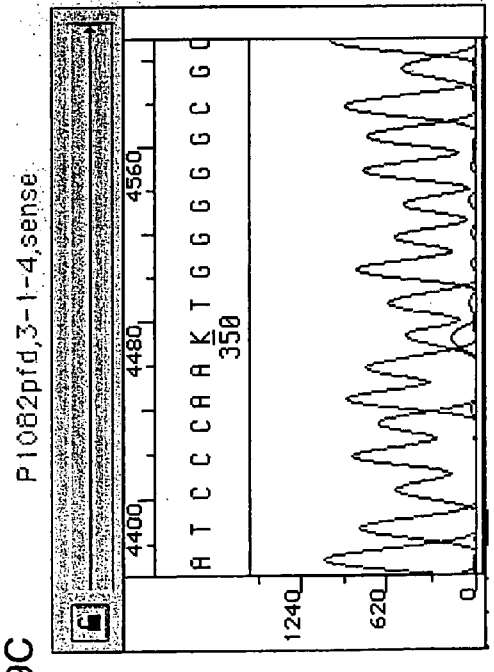

FIGS. 39A and B show the results of analysis of the nucleotide sequence in the vicinity of the nucleotides encoding an amino acid at position 548 of the ALS protein. FIGS. 39C and D show the results of analysis of the nucleotide sequence in the vicinity of the nucleotides encoding an amino acid at position 627 of the ALS protein. As shown in FIGS. 39 A to D, heterologous sequences of wild type and mutant were found for the double-point mutation of these lines. Hence, the mutant ALS gene was shown to be incorporated in the genome. In addition, 3 of 9 calli did not grow well in the presence of 10 µM bispyribac-sodium. However, this was thought to be caused by low expression amount of the double-point mutant ALS gene introduced.

Figure 40:
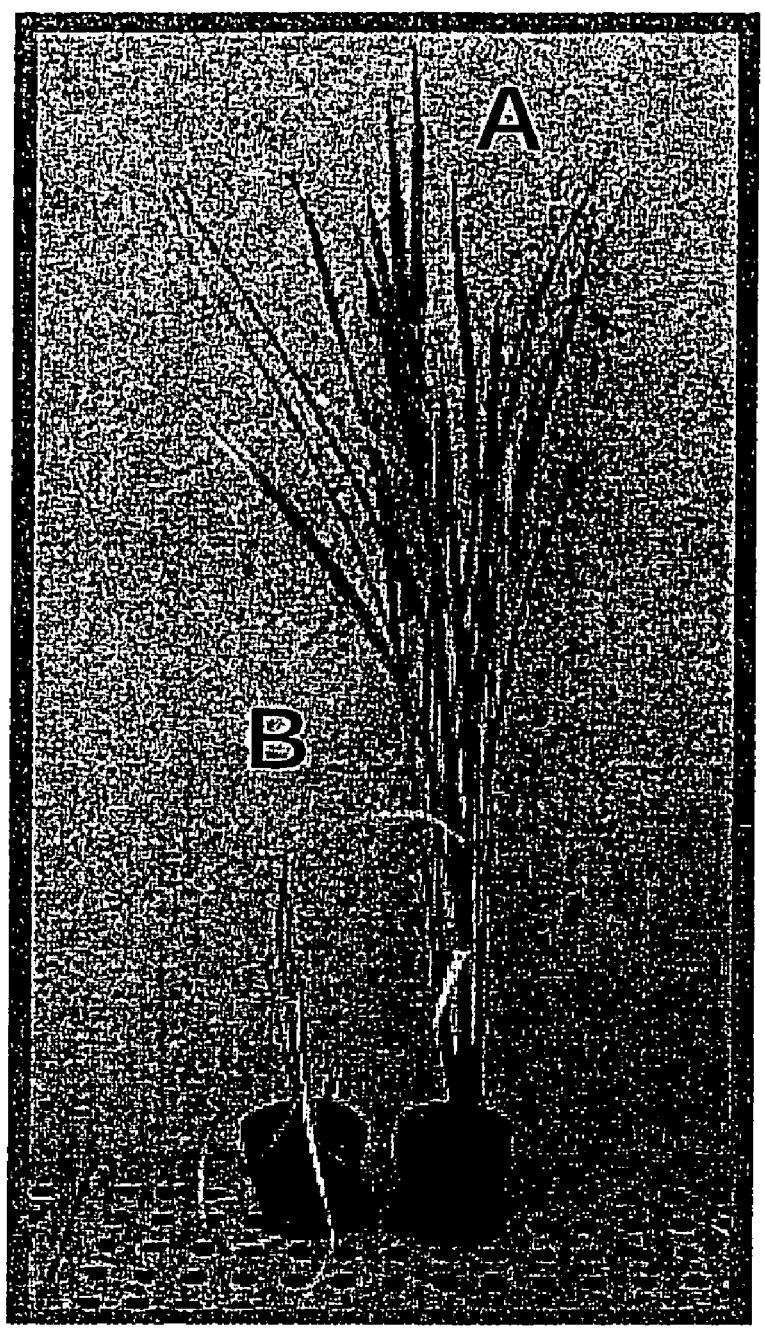
FIG. 40 is a photograph showing the result of measuring bispyribac-sodium sensitivity of a rice plant (Nippon-bare) transformed with the mutant ALS gene, wherein A shows a rice plant transformed with the mutant ALS gene, and B shows a rice plant transformed with the wild type ALS gene.

Of 80 hygromycin resistant transformant rice plants potted, those which grew normally at the leaf stage 5 were 27 plants to which the mutant ALS gene had been introduced and 46 plants to which the wild type ALS gene had been introduced. Plants containing the wild type ALS gene introduced therein tended to grow healthier than those containing the mutant ALS gene therein. At this time, 4 plants containing the mutant ALS gene introduced therein and 5 plants containing the wild type ALS gene introduced therein were appropriately selected, and 1 kg of a.i./ha bispyribac-sodium salt supplemented with 0.2% surfactant K was sprayed over the leaves and stems. The results of a growth survey conducted about 40 days after spraying are shown in FIG. 40. In FIG. 40, the plant length A was about 90 cm.

As shown in FIG. 40, an individual plant containing the mutant ALS gene introduced therein grew almost normally (A), and the plant was shown to have bispyribac-sodium resistance. Genomic DNA was prepared from the bispyribac-sodium resistant transformant rice plant using DNeasy Plant Kit (QIAGEN). Then PCR was performed using the genomic DNA as a template and using a set of a sense primer (3-1-4: SEQ ID NO: 9) and an antisense primer (4-83-3: SEQ ID NO: 8) that flank the double-point mutation portion therebetween. The nucleotide sequence of the resulting DNA fragment was examined in the same manner as in the above callus. Hence, the presence of double-point mutation in the transformant rice plant was confirmed.

All publications, patents and patent applications cited herein are incorporated by reference in their entirety.

EFFECT OF THE INVENTION

As described in detail above, the present invention can provide ALS gene encoding ALS enzyme which has good resistance to all ALS-inhibiting herbicides and shows extremely high level of resistance to PC herbicides.

What is claimed is:

1. An isolated acid comprising a nucleic acid sequence encoding an acetolactate synthase protein in which the amino acid in the position corresponding to position 627 of the wild-type acetolactate synthase of SEQ ID NO:12 is isoleucine, wherein said acetolactate synthase protein has resistance to a pyrimidinyl carboxy herbicide and has acetolactate synthase activity.

2. The isolated nucleic acid according to claim 1, wherein said protein further comprises an additional substitution, wherein the amino acid at the position corresponding to position 548 of the wild-type acetolactate synthase of SEQ ID NO:12 is leucine.

3. The isolated nucleic acid according to claim 1, wherein said nucleic acid encodes SEQ ID NO:12, wherein the amino acid at position 627 is isoleucine.

4. The isolated nucleic acid according to claim 2, wherein said protein consists of the amino acid sequence of SEQ ID NO:1.

5. A recombinant vector comprising a nucleic acid sequence selected from the group consisting of:

(a) a nucleic acid sequence encoding an acetolactate synthase protein in which the amino acid in the position corresponding to position 627 of the wild-type acetolactate synthase of SEQ ID NO:12 is isoleucine, wherein said acetolactate synthase protein has resistance to a pyrimidinyl carboxy herbicide and has acetolactate synthase activity, and (b) a nucleic acid sequence encoding an acetolactate synthase protein in which the amino acid in the position corresponding to position 627 of the wild-type acetolactate synthase of SEQ ID NO:12 is isoleucine and the amino acid at the position corresponding to position 548 of the wild-type acetolactate synthase of SEQ ID NO:12 is leucine, wherein said acetolactate synthase protein has resistance to a pyrimidinyl carboxy herbicide and has acetolactate synthase activity.

6. A transformant which has the recombinant vector of claim 5.

7. A plant which has the isolated nucleic acid of according to any one of claims 1, 2, 3 or 4 and has resistance to a pyrimidinyl carboxy herbicide.

8. A method for rearing the plant of claim 7 which comprises rearing the plant in the presence of a pyrimidinyl carboxy herbicide.

9. A method for selecting a transformant cell having the nucleic acid sequence selected from the group consisting of:

(a) a nucleic acid sequence encoding an acetolactate synthase protein in which the amino acid in the position corresponding to position 627 of the wild-type acetolactate synthase of SEQ ID NO:12 is isoleucine, wherein said acetolactate synthase protein has resistance to a pyrimidinyl carboxy herbicide and has acetolactate synthase activity, and (b) a nucleic acid sequence encoding an acetolactate synthase protein in which the amino acid in the position corresponding to position 627 of the wild-type acetolactate synthase of SEQ ID NO:12 is isoleucine and the amino acid at the position corresponding to position 548 of the wild-type acetolactate synthase of SEQ ID NO:12 is leucine, wherein said acetolactate synthase protein has resistance to a pyrimidinyl carboxy herbicide and has acetolactate synthase activity, said method comprising:

(a) introducing a vector comprising the nucleic said nucleic acid into a host as a selection marker; and (b) culturing the host in the presence of a pyrimidinyl carboxy herbicide.

* * * * *

SEQUENCE LISTING

```
<160> NUMBER OF SEQ ID NOS: 11

<210> SEQ ID NO 1
<211> LENGTH: 644
<212> TYPE: PRT
<213> ORGANISM: Oryza sativa var.Kinmaze

<400> SEQUENCE: 1

Met Ala Thr Thr Ala Ala Ala Ala Ala Ala Ala Leu Ser Ala Ala Ala
 1               5                  10                  15

Thr Ala Lys Thr Gly Arg Lys Asn His Gln Arg His His Val Leu Pro
             20                  25                  30

Ala Arg Gly Arg Val Gly Ala Ala Ala Val Arg Cys Ser Ala Val Ser
         35                  40                  45

Pro Val Thr Pro Pro Ser Pro Ala Pro Pro Ala Thr Pro Leu Arg Pro
     50                  55                  60

Trp Gly Pro Ala Glu Pro Arg Lys Gly Ala Asp Ile Leu Val Glu Ala
 65                  70                  75                  80

Leu Glu Arg Cys Gly Val Ser Asp Val Phe Ala Tyr Pro Gly Gly Ala
                 85                  90                  95
```

```
Ser Met Glu Ile His Gln Ala Leu Thr Arg Ser Pro Val Ile Thr Asn
            100                 105                 110
His Leu Phe Arg His Glu Gln Gly Glu Ala Phe Ala Ala Ser Gly Tyr
            115                 120                 125
Ala Arg Ala Ser Gly Arg Val Gly Val Cys Val Ala Thr Ser Gly Pro
            130                 135                 140
Gly Ala Thr Asn Leu Val Ser Ala Leu Ala Asp Ala Leu Leu Asp Ser
145                 150                 155                 160
Val Pro Met Val Ala Ile Thr Gly Gln Val Pro Arg Arg Met Ile Gly
                165                 170                 175
Thr Asp Ala Phe Gln Glu Thr Pro Ile Val Glu Val Thr Arg Ser Ile
                180                 185                 190
Thr Lys His Asn Tyr Leu Val Leu Asp Val Glu Asp Ile Pro Arg Val
            195                 200                 205
Ile Gln Glu Ala Phe Phe Leu Ala Ser Ser Gly Arg Pro Gly Pro Val
            210                 215                 220
Leu Val Asp Ile Pro Lys Asp Ile Gln Gln Gln Met Ala Val Pro Val
225                 230                 235                 240
Trp Asp Thr Ser Met Asn Leu Pro Gly Tyr Ile Ala Arg Leu Pro Lys
                245                 250                 255
Pro Pro Ala Thr Glu Leu Leu Glu Gln Val Leu Arg Leu Val Gly Glu
                260                 265                 270
Ser Arg Arg Pro Ile Leu Tyr Val Gly Gly Gly Cys Ser Ala Ser Gly
            275                 280                 285
Asp Glu Leu Arg Trp Phe Val Glu Leu Thr Gly Ile Pro Val Thr Thr
            290                 295                 300
Thr Leu Met Gly Leu Gly Asn Phe Pro Ser Asp Asp Pro Leu Ser Leu
305                 310                 315                 320
Arg Met Leu Gly Met His Gly Thr Val Tyr Ala Asn Tyr Ala Val Asp
                325                 330                 335
Lys Ala Asp Leu Leu Leu Ala Phe Gly Val Arg Phe Asp Asp Arg Val
                340                 345                 350
Thr Gly Lys Ile Glu Ala Phe Ala Ser Arg Ala Lys Ile Val His Ile
            355                 360                 365
Asp Ile Asp Pro Ala Glu Ile Gly Lys Asn Lys Gln Pro His Val Ser
            370                 375                 380
Ile Cys Ala Asp Val Lys Leu Ala Leu Gln Gly Leu Asn Ala Leu Leu
385                 390                 395                 400
Gln Gln Ser Thr Thr Lys Thr Ser Ser Asp Phe Ser Ala Trp His Asn
                405                 410                 415
Glu Leu Asp Gln Gln Lys Arg Glu Phe Pro Leu Gly Tyr Lys Thr Phe
                420                 425                 430
Gly Glu Glu Ile Pro Pro Gln Tyr Ala Ile Gln Val Leu Asp Glu Leu
            435                 440                 445
Thr Lys Gly Glu Ala Ile Ile Ala Thr Gly Val Gly Gln His Gln Met
            450                 455                 460
Trp Ala Ala Gln Tyr Tyr Thr Tyr Lys Arg Pro Arg Gln Trp Leu Ser
465                 470                 475                 480
Ser Ala Gly Leu Gly Ala Met Gly Phe Gly Leu Pro Ala Ala Ala Gly
                485                 490                 495
Ala Ser Val Ala Asn Pro Gly Val Thr Val Val Asp Ile Asp Gly Asp
                500                 505                 510
```

-continued

```
Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
        530                 535                 540

Val Val Gln Leu Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
                580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
        610                 615                 620

Ile Pro Ile Gly Gly Ala Phe Lys Asp Met Ile Leu Asp Gly Asp Gly
625                 630                 635                 640

Arg Thr Val Tyr

<210> SEQ ID NO 2
<211> LENGTH: 2279
<212> TYPE: DNA
<213> ORGANISM: Oryza sativa var.Kinmaze

<400> SEQUENCE: 2
ctcgccgccg ccgccgccgc caccacccac catggctacg accgccgcgg ccgcggccgc      60
cgccctgtcc gccgccgcga cggccaagac cggccgtaag aaccaccagc gacaccacgt     120
ccttcccgct cgaggccggg tggggcggc ggcggtcagg tgctcggcgg tgtcccggt      180 caccccgccg tccccggcgc cgccggccac gccgctccgg ccgtgggggc cggccgagcc     240
ccgcaagggc gcggacatcc tcgtggaggc gctggagcgg tgcggcgtca gcgacgtgtt     300
cgcctacccg ggcggcgcgt ccatggagat ccaccaggcg ctgacgcgct ccccggtcat     360
caccaaccac ctcttccgcc acgagcaggg cgaggcgttc gcggcgtccg ggtacgcgcg     420
cgcgtccggc cgcgtcgggg tctgcgtcgc cacctccggc cccggggcaa ccaacctcgt     480
gtccgcgctc gccgacgcgc tgctcgactc cgtcccgatg gtcgccatca cgggccaggt     540
ccccccgccg catgatcggca ccgacgcctt ccaggagacg cccatagtcg aggtcacccg     600
ctccatcacc aagcacaatt accttgtcct tgatgtggag gacatccccc gcgtcataca     660
ggaagccttc ttcctcgcgt cctcgggccg tcctggcccg gtgctggtcg acatccccaa     720
ggacatccag cagcagatgg ccgtgccggt ctgggacacc tcgatgaatc taccagggta     780
catcgcacgc ctgcccaagc cacccgcgac agaattgctt gagcaggtct tgcgtctggt     840
tggcgagtca cggcgcccga ttctctatgt cggtggtggc tgctctgcat ctggtgacga     900
attgcgctgg tttgttgagc tgactggtat cccagttaca accactctga tgggcctcgg     960
caatttcccc agtgacgacc cgttgtccct gcgcatgctt gggatgcatg gcacggtgta    1020
cgcaaattat gccgtggata aggctgacct gttgcttgcg tttggtgtgc ggtttgatga    1080
tcgtgtgaca gggaaaattg aggcttttgc aagcagggcc aagattgtgc acattgacat    1140
tgatccagca gagattggaa agaacaagca accacatgtg tcaatttgcg cagatgttaa    1200
gcttgcttta cagggcttga atgctctgct acaacagagc acaacaaaga caagttctga    1260
ttttagtgca tggcacaatg agttggacca gcagaagagg gagtttcctc tggggtacaa    1320
aacttttggt gaagagatcc caccgcaata tgccattcag gtgctggatg agctgacgaa    1380
```

```
aggtgaggca atcatcgcta ctggtgttgg gcagcaccag atgtgggcgg cacaatatta    1440
cacctacaag cggccacggc agtggctgtc ttcggctggt ctgggcgcaa tgggatttgg    1500
gctgcctgct gcagctggtg cttctgtggc taacccaggt gtcacagttg ttgatattga    1560
tggggatggt agcttcctca tgaacattca ggagctggca ttgatccgca ttgagaacct    1620
ccctgtgaag gtgatggtgt tgaacaacca acatttgggt atggtggtgc aattggagga    1680
taggttttac aaggcgaata gggcgcatac atacttgggc aacccggaat gtgagagcga    1740
gatatatcca gattttgtga ctattgctaa ggggttcaat attcctgcag tccgtgtaac    1800
aaagaagagt gaagtccgtg ccgccatcaa gaagatgctc gagactccag ggccatactt    1860
gttggatatc atcgtcccgc accaggagca tgtgctgcct atgatcccaa ttgggggcgc    1920
attcaaggac atgatcctgg atggtgatgg caggactgtg tattaatcta taatctgtat    1980
gttggcaaag caccagcccg gcctatgttt gacctgaatg acccataaag agtggtatgc    2040
ctatgatgtt tgtatgtgct ctatcaataa ctaaggtgtc aactatgaac catatgctct    2100
tctgttttac ttgtttgatg tgcttggcat ggtaatccta attagcttcc tgctgtctag    2160
gtttgtagtg tgttgttttc tgtaggcata tgcatcacaa gatatcatgt aagtttcttg    2220
tcctacatat caataataag agaataaagt acttctatgt aaaaaaaaaa aaaaaaaa     2279
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 3

```
catcaccaac cacctctt                                                     18
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 4

```
acacggactg caggaata                                                     18
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 5

```
ttacaaggcg aatagggc                                                     18
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 6

```
ggaaacagct atgaccatg                                                    19
```

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 7
gctctgctac aacagagcac a                                              21

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 8
gctttgccaa catacag                                                   17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 9
aggtgtcaca gttgttg                                                   17

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 10
gcatcttctt gaatggcg                                                  18

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 11
agtcctgcca tcaccatcca g                                              21
```